(12) United States Patent
Benning et al.

(10) Patent No.: US 7,226,764 B1
(45) Date of Patent: Jun. 5, 2007

(54) COMPOSITIONS AND METHODS FOR THE SYNTHESIS AND SUBSEQUENT MODIFICATION OF URIDINE-5'-DIPHOSPHOSULFOQUINOVOSE (UDP-SQ)

(75) Inventors: Christoph Benning, East Lansing, MI (US); Sherrie Lea Sanda, Haslett, MI (US); Bin Yu, East Lansing, MI (US)

(73) Assignee: The Board of Trustees Operating Michigan State University, East Lansing, MI (US)

( * ) Notice: Subject to any disclaimer, the term of this patent is extended or adjusted under 35 U.S.C. 154(b) by 0 days.

(21) Appl. No.: 09/709,020

(22) Filed: Nov. 8, 2000

(51) Int. Cl.
| | |
|---|---|
| C12P 7/00 | (2006.01) |
| C12N 9/00 | (2006.01) |
| C12N 9/10 | (2006.01) |
| C12N 1/20 | (2006.01) |
| C12N 15/00 | (2006.01) |
| C12Q 21/04 | (2006.01) |
| C07H 21/04 | (2006.01) |
| C12Q 1/00 | (2006.01) |
| C12Q 1/68 | (2006.01) |
| C12Q 1/48 | (2006.01) |

(52) U.S. Cl. ............. 435/132; 435/183; 435/193; 435/4; 435/6; 435/15; 435/252; 435/320.1; 435/69.1; 435/71.1; 435/440; 536/23.2; 536/23.7

(58) Field of Classification Search ............. 435/95, 435/193, 252.3, 320.1, 189, 183, 252.33, 435/410, 71.1, 132, 186, 4, 6, 15, 69.1, 440; 514/24; 536/23.2, 23.7
See application file for complete search history.

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,774,180 A * | 9/1988 | Toth et al. | 435/69.7 |
| 4,965,188 A | 10/1990 | Mullis et al. | 435/6 |
| 5,106,739 A * | 4/1992 | Comai et al. | 800/294 |
| 5,374,716 A | 12/1994 | Biermann et al. | 536/18.6 |
| 5,504,200 A * | 4/1996 | Hall et al. | 435/252.2 |
| 5,584,807 A | 12/1996 | McCabe | 604/71 |
| 5,876,962 A * | 3/1999 | Bishop et al. | 435/69.1 |
| 6,087,558 A * | 7/2000 | Howard et al. | 800/278 |
| 6,265,638 B1 * | 7/2001 | Bidney et al. | 800/294 |

OTHER PUBLICATIONS

Essigmann et al. Prediction of the active-site structure and NAD+ binding in SQD1. Archives of Biochemistry and Biophysics, vol. 369, No. 1, pp. 30-41. 1999.*

(Continued)

*Primary Examiner*—Tekchand Saidha
*Assistant Examiner*—Yong D. Pak
(74) *Attorney, Agent, or Firm*—Medlen & Carroll, LLP

(57) ABSTRACT

The present invention is directed to compositions and methods related to the synthesis and modification of uridine-5'-diphospho-sulfoquinovose (UDP-SQ). In particular, the methods of the present invention comprise the utilization of recombinant enzymes from *Arabidopsis thaliana*, UDP-glucose, and a sulfur donor to synthesize UDP-SQ, and the subsequent modification of UDP-SQ to form compounds including, but not limited to, 6-sulfo-α-D-quinovosyl diaclyglycerol (SQDG) and alkyl sulfoquinovoside. The compositions and methods of the invention provide a more simple, rapid means of synthesizing UDP-SQ, and the subsequent modification of UDP-SQ to compounds including, but not limited to, SQDG.

24 Claims, 23 Drawing Sheets

Pathway for UDP-SQ Biosynthesis

OTHER PUBLICATIONS

Essigmann et al. (GenEmbl database—Accession # AF022082). 1999.*

Guler et al. A cyanobacterial gene, sqdX, required for biosynthesis of the sulfolipid sulfoquinovosyldiacylglycerol. Journal of Bacteriology, vol. 182, No. 2, pp. 543-545. 1996.*

Guler et al. (GenEmbl database—Accession # U45308 AF155063). 1999.*

Mulichak et al. Crystal structure of SQD1, an enzyme involved in the biosynthesis of the plant sulfolipid headgroup donor UDP-sulfoquinovose. PNAS, vol. 96, No. 23, pp. 13097-13102. 1999.*

Stratagene Catalog. pp. 34-84 and appendix. 1999-2000.*

Bevan et al. GenEmbl database Accession ATF7J8. Jul. 26, 2000.*

Punt et al. Gene, 56 (1987) 117-124.*

McNally et al. Proc. Natl. Acad. Sci. USA, vol. 85, pp. 7270-7273, Oct. 1988.*

Dong et al. Archives of Biochemistry and Biophysics, vol. 327, pp. 254-259, Mar. 1996.*

Yue et al. Nucleic Acids Research, vol. 28, pp. e14, 2000.*

Kovach et al. Gene, vol. 166, pp. 175-176, Dec. 1995.*

SEQ ID No. 1—Sequence Alignment.*

SEQ ID No. 3 Sequence Alignemnt.*

SEQ ID No. 6: Sequence Alignemnt.*

Sequence Alignment—SEQ ID No. 6.*

Bechtold et al., "*In planta Agrobacterium* mediated gene transfer by infiltration of adults *Arabidopsis thaliana* plants," *C.R. Acad. Sci. Paris*, 316:1194-1199 (1993).

Becker, D., "Binary vectors which allow the exchange of plant selectable markers and reporter genes," *Nucleic Acids Res.* 18:203 (1990).

Benning C. "Biosynthesis and Function of the Sulfolipid Sulfoquinovosyl Diacylglycerol," *Annu Rev. Plant Physiol. Plant Mol. Biol.*, 49:53-75 (1998).

Bennings et al., "The sulfolipid sulfoquinovosyldiacylglycerol is not required for photosynthetic electron transport in *Rhodobacter sphaeroides* but enhances growth under phosphate limitation," *Proc. Natl. Acad. Sci. (USA)*, 90:1561-65 (1993).

Benning et al., "Accumulation of a Novel Glycolipid and a Betaine Lipid in Cells of *Rhodobacter sphacroides* Grown under Phosphate Limitation," *Arch. Biochem. & Biophys.*, 317:103-111 (1995).

Benning C & Somerville CR, "Isolation and Genetic Complementation of a Sulfolipid-Deficient Mutant of *Rhodobacter sphaeroides*," *J. Bacteriol.*, 174(7):2352-2360 (1992).

Benson, A.A., "The Plant Sulfolipid," *Adv. Lipid Res.* 1:387-94 (1963).

Black et al, "Analysis of a Het- mutation in *Anabaena* sp. PCC7120 implicates a secondary metabolite in the regulation of heterocyst spacing," *J. Bacteriol.*, 174:2282-2292 (1994).

Browse et al., "Fluxes through the prokaryotic and eukaryotic pathways of lipid synthesis in the '16:3' plant *Arabidopsis thaliana*," *J. Biochem.*, 235:25-31 (1986).

Chen L & Li H, "A mutant deficient in the plastid lipid DGD is defective in protein import into chloroplasts," *The Plant J.*, 16(1):33-39 (1998).

Clough, S. and Bent, A., "Floral dip: a simplified method for *Agrobacterium*-mediated transformation of *Arabidopsis thaliana*," *Plant J.*, 16: 735-43 (1998).

Dörmann et al., "Isolation and Characterization of an *Arabidopsis* Mutant Deficient in the Thylakoid Lipid Digalactosyl Diacylglycerol," *The Plant Cell*, 7:1801-10 (1995).

Dörmann et al., "*Arabidopsis* Galactolipid Biosynthesis and Lipid Trafficking Mediated by DGD1," *Science*, 284:2181-2184 (1999).

Essigman et al., "Phosphate Availability Affects the Thylakoid Lipid Composition and Expression of SQD1, a Gene Required for Sulfolipid Biosynthesis in *Arabidopsis thaliana*," *Proc. Natl. Acad. Sci. USA*, 95:1950-955 (1998).

Essigmann et al., "Prediction of the Active-Site Structure and NAD Binding in SQD1, a Protein Essential for Sulfolipid Biosynthesis in *Arabidopsis*," *Arch. Biochem. & Biophys.*, 369(1):30-41 (1999).

Gordon-Kamm et al., "Transformation of Maize Cells and Regeneration of Fertile Transgenic Plants," *Plant Cell*, 2:603-618 (1990).

Güler et al., "A Cyanobacterial Gene, sqdX, Required for the Biosynthesis of the Sulfolipid Sulfoquinovosyldiacylglycerol," *J. Bacteriol.*, 182(2):543-45 (2000).

Güler et al., "A Null Mutant of *Synechococcus* sp. PCC7942 Deficient in the Sulfolipid Sulfoquinovosyl Diacylglycerol," *J. Biol. Chem.*, 271(13):7501-7507 (1996).

Gustafson et al., "AIDS-Antiviral Sulfolipids From Cyanobacteria (Blue-Green Algae)," *J. Nail Cancer Inst.*, 81:1254-258 (1989).

Hanashima et al., "Structural determination of sulfoquinovosyldiacylglycerol by chiral syntheses," *Tetrahedron Letters*, 41:4403-4407 (2000).

Heinz et al., "Synthesis of different nucleoside 5'-diphospho-sulfoquinovoses and their use for studies on sulfolipid biosynthesis in chloroplasts," *Eur. J. Biochem.*, 184:445-453 (1989).

Logemann et al., "Improved Method for the Isolation of RNA from Plant Tissues," *Anal. Biochem.*, 163:16-20 (1987).

Miyano, M. & Benson, A.A., "The Plant Sulfolipid VII, Synthesis of 6-sulfo-α-D-quinovopyranosyl-(1→1')-glycerol and Radiochemical Synthesis of Sulfolipids," *J. Am. Chem. Soc.*, 84:59-62 (1962).

Mulichak et al., "Crystal structure of SQD1, an enzyme involved in the biosynthesis of the plant sulfolipid headgroup donror—UDP-sulfoquinovose," *Proc. Nail. Acad. Sci. (USA)*, 96(23):13097-13102 (1999).

Newman et al., "Genes Galore: A Summary of Methods for Accessing Results from Large-Scale Partial Sequencing of Anonymous *Arabidopsis* cDNA Clones," *Plant Physiol.*, 106:1241-1255 (1994).

Ohta et al., "Studies on a novel DNA polymerase inhibitor group, synthetic sulfoquinovosylacylglycerols: inhibitory action on cell proliferation," *Mutation Rsch.*, 467:139-152 (2000).

Ohta et al., "Sulfoquinovosyldiacylglycerol, KM043, a new potent inhibitor of eukaryotic DNA polymerases and HIV-reverse transcriptase type 1 from a marine red alga, *Gigartina tenella*," *Chem. Pharm. Bull.*, 46(4):684-86 (1998) [Abstract Only].

Ohta et al., "Action of a New Mammalian DNA Polymerase Inhibitor Sulfoquinovosyl diacylglycerol." *Biol. Pharm. Bull.*, 22(2):111-16 (1999).

Prentki, P. and Krisch, H.M., "In vitro insertional mutagenesis with a selectable DNA fragment," *Gene*, 29:303-313 (1984).

Rossak et al., "Accumulation of UDP-sulfoquinovose in a Sulfolipid-deficient Mutant of *Rhodobacter sphaeroides*," *J. Biol. Chem.*, 270(43):25792-25797 (1995).

Roy A.B & Hewlins MJE, "An improved preparation of cyclohexylammonium allyl and D-glyccr-1'-yl 6-deoxy-6-C-sulfonato-α-D glucopyranosides," *Carbohydrate Rsch.*, 310:173-176 (1998).

Roy, A.B. & Hewlins, J.E., "Sulfoquinovose and its aldonic acid: their preparation and oxidation to 2-sulfoncetaldehyde by periodate," *Carbohydrate Res.*, 302:113-17 (1997).

Sambrook, et al., Molecular Cloning: A Laboratory Manual, 2nd ed., Cold Springs Harbor Laboratory Press, New York, pp. 16.7-16.8 (1989).

Sandra et al., "Enzymatic Action of SQD1—A protein involved in Sulfolipid Headgroup Biosynthesis," Abstract & Poster, presented at the annual meeting for the American Society for Plant Physiologists, Jul. 15, 2000.

Shirahashi et al., "Isolation and Identification of Anti-tumor-Promoting Principles from the Fresh-Water Cyanobacterium *Phormidium tenue*," *Chem. Pharm. Bull.*, 41(9):1664-66 (1993).

Wolk et al., "Construction of shuttle vectors capable of conjugative transfer from *Escherichia coli* to nitrogen-fixing filamentous cyanobacteria," *Proc. Natl. Acad. Sci. USA*, 81:1561-565 (1984).

* cited by examiner pQE-30

Eco RI/RBS — ATG AGAGGATCG — 6xHis — RGS·His epitope

BamHI SphI SacI KpnI SmaI XmaI SalI PstI HindIII

—GGATCCGCATGCGAGCTCGGTACCCCGGGTCGACCTGCAGCCAAGCTT AATTAGCTGAG — $t_0$ (SEQ ID NO:22)

pQE-31

Eco RI/RBS — ATG AGAGGATCT — 6xHis — RGS·His epitope

BamHI SphI SacI KpnI SmaI XmaI SalI PstI HindIII

AC GGATCCGCATGCGAGCTCGGTACCCCGGGTCGACCTGCAGCCAAGCTT AATTAGCTGAG — $t_0$ (SEQ ID NO:23)

pQE-32

Eco RI/RBS — ATG AGAGGATCT — 6xHis — RGS·His epitope

BamHI SphI SacI KpnI SmaI XmaI SalI PstI HindIII

G GGATCCGCATGCGAGCTCGGTACCCCGGGTCGACCTGCAGCCAAGCTT AATTAGCTGAG — $t_0$ (SEQ ID NO:24)

FIG. 3 CONTINUED

```
SQDX       1                                                                                         a
        2-61    tgcgcatcgc  tctctttacc  gagacgttcc  tcccccaaagt  ggatggcatc  gtcacgcggc
       62-121   ttcggcacac  ggtcgatcac  ctgcagcgtc  ttggccacac   cgtcatggtt  ttttgccccg
      122-181   acggcgggct  ccgcgagcac  aaggggctc   gagtctatgg   ggttaaaggc  tttccgctac
      182-241   cgctctatcc  cgagctgaag  ctagctttc   cgttgccgaa   agtggaaaa   gccttggagc
      242-301   ggttccggcc  cgacctgatc  cacgtggtca  atccggctgt   gttggggttg  ggcggcatct
      302-361   actatgccaa  ggcgctaaat  gtgccactcg  tggcgtccta   tcacacccat  ttgccgaaat
      362-421   acctttgagca ttacggggctg gggtcttgg   aggggtgct    ctgggaattg  ctgaagctgg
      422-481   cgcataacca  agcagcgatc  aacctctgta  cttcaaccgc   gatggtgcag  gagctgacag
      482-541   atcacgcat   tgagcactgt  tgcctctggc  agcgaggagt   ggataccgag  acctttcggc
      542-601   cagacttggc  tactgctgcg  atgcgcgatc  gcctcagtgg   cggtaagccc  actgcgccct
      602-661   tgttgctcta  cgtcggacgc  ctctcagccg  agaagcaaat   cgatcgcctg  cgacccattt
      662-721   tggatgccaa  tcctgaggct  tgcttggcct  tggtcggcga   tgcccgaac   cgggccgaac
      722-781   tagagcaatt  gttgctggc   acccagacgc  agttcattgg   ttgtcttttcc ctatctgcat  ggggaacagc
      782-841   taggggcggc  ctacgcttct  gctgacgctt  gctgacgcgt   ttgtccggt   cgtggcggcc  gaaacccctcg
      842-901   gtctagtctt  gctggaagcc  atgcagcagg  gttgtccgg    gttgttcct   gttcgatcct  aattccggtg
      902-961   gcattccga   tattgtcagc  gacggcatta  atggtttcct   tggctaaccc  gagatgaac
      962-1021  aagggggcgat cgctgcgatt  cagcgcttgt  tggctaaccc   ggagctggaa  cgcagccacg
     1022-1081  gccaagcggc  tcgtcaagaa  gccgaacgct  ggagctggaa   cgcagccacg  cgccaactcc
     1082-1134  aggactacta  ctgcgaggtg  ttggcagatg  gttgcttacc   cttagcggcc  tga
```

FIG. 10

```
AtSQDX-1
   1-57             ctacacg ttaccttccg gtactggaaa cagtcgttta atcaaccaat tgattggtcc
  58-117  caaaacatga actttctttt tcctccagaa ccaaatcgct gcactgtact gttcattgcg
 118-177  tatcttttgtc gttgctgctc tccaatcata tttctcttg tcttctcttc ccgcttttcc
 178-237  aatgatctct cttgtttcac ggtcgtgcag taagttctc agttttgtca cgcaatcttc
 238-297  aacatctcca gggttgaaca aaaatccggt ttttcccctcc tgatgaaaac atcagaatca
 298-357  gaaaaccaca agctcaatat aggttgaccc ataagaacaa tcaatgcaag atcattttgt
 358-417  gtaccagtct atgattgaat aaagtttcag ttcggttaca gctcgcttat aagaaaattg
 418-477  gcagaaattg ttttttcaac catttcggtt cggttgatat gctcatcaat atggtttggc
 478-537  agttaattgt aattcagata attcactgac ctgatcttca gggattatat cagggattcc
 538-597  accggcacgg gccgcgacga caggaagtcc tgaagacatt gcttcaagaa ccacaaggcc
 598-657  aagtgtctcc gactctgatg gcatcacaaa cacatctcca cgctggcatt cttgcgtaag acttctcaag
 658-717  ttcatcgcct tgtaacgttc cagtgaagtc cgctggcatt ccggtaaaca aatgttgttg actctcaag
 718-777  atccctctctt taagaaaacg aaacagataa acaaaattac aatgttgttg actagaaatc
 778-837  ttcagataac aatatggcca atctttaaca aaactagtac ttgtatggtc catctccaat
 838-897  gaaagcaatc cgagcttcag gtaatttgtc cattacactg cacacaaatt tctcaatatc
 898-957  aaaattcgat acaccactta aaagaagtga gtccagttta tacaaaattc taacctcttt
 958-1017 aaaagctcca aactctttttc tacgccaatg cgacctacat gaatcactag tggctttcct
1018-1077 ggttcgccat tactgttaat tacaaaatat gattagcgtg gaaagtatca
1078-1137 ttgttttttaa tgcatataaa agaaacgtat attctattct tgcctcagtc ttatacgcat
1138-1197 ttcttgagaa cggaaacggg gattgaagct ttctgaatcg acaccctat tccaaagtcg
1198-1257 aagttgatta gcttcaatat atgaaaaaaa gaagaagaaa atgtaagttt tgaacaatca
1258-1317 tagcttgt acaaaaatgt cttcttcac ctgcagttgc accagctgct
1318-1377 ataagatctt ttccaatggc agcagaagga actaatgtaa gatcagccgc tctgtgaagg
1378-1437 aaccctgata aaagcatatt caagtttagt ttcatattat acatcacaat aaaccagaaa
```

FIG. 11

```
1438-1497   aagaagaagg aaattttgac atttgaaaag cgggtttttac atacttatta tagaccacat
1498-1557   tggttttacc accaactaa aagtgtatct tgggatgtat ctgcacatca acacaagctt
1558-1617   aatcttagac aaaattttt ttataacaac attgtgaaat gaggcagaaa aagtactta
1618-1677   cacagggacg tgtgtgtggt aagacattac tattggtaca gatagcattt ttgctattgc
1678-1737   cagagcacca aagacctaaa aatttagtc agggaaaaaa gagagtcaag ttctggattc
1738-1797   tctccagttc actggtcttg ctaatgtttt agtaatgtga attcttgagg gatttaccat
1798-1857   aactccggga gatgaagcgt gtataatgtc aggcttaaac cgtgcaattt cagagatgat
1858-1917   tcttggacta agcgcaagcg agagtggaac cttttggtaa taaggacaag ggaagctaca
1918-1977   gaagagaaga agaaattagc gatattacca aatagagaac atccagtgag taaactaaat
1978-2037   ggtgctacct tctttgatcca atgactctgg ctccataaaa atccttcagga acaccttcat
2038-2097   gtgtcgtcac gactataacc tatgaagcaa aaaagttatt aaaaaaaaaa aaaaaggaac
2098-2157   agttaacact tgtcaagtaa ttctaattct gaaacagtt acttatgagc tgactgaaaa
2158-2217   gatacttaag ttgaagaatg agatagtaaa agaagaaacc tcgtctccca tttcacggag
2218-2277   gtatctaatg aaattctgga atctgttttt gtagccggat acatagctgc aacaaaatca
2278-2337   aagagagaat cacttccaat aataacatga catataataa aagctttttgg tcaatggatc
2338-2397   ggtgattccg agaatcttgg gatattcaca actaaaatct gacaactttg actcaaacaa
2398-2457   atcctgaatg taattggttt taacgatcta ctatataatt tgctaaattg gtggtgtagc
2458-2517   aaattcatac attagcgagt atctcttcat aaaataaatg taacgatcaa atcgaaagaa
2518-2577   aaaaacatta caggaaaaag tcaaccaagg aaaaaaatga gtgaagaaga tttcacaga
2578-2637   gacatttcgt cgaacacaaa acaagcaatt cctaggctta gagagcgact cttacgcaaa
2638-2697   gggagaaggc tcaacacaaga gagcaattct ttctctgact gagtaatag caggatcgag
2698-2757   aagcggcgca tcaatctccg attcgtcatc ttgtaatcac tccacagaag cggagcttgc tcatatcgtt
2758-2817   ggacccagaa acagcttcct ttgtaatcac tccacagaag cggagcttgc tttcttgct
2818-2877   aatgggtaat ctccggtgac caaacgaaag agggaatga agaacaaaag aagagacct
2878-2937   gggaggagaa caagaggttg cagagaagaa agaacaagtg ttagtcgtgc taggaagcaa
2938-2979   atgaggaggt atagagagat ttatagaaga aagagtcgtc at
```

FIG. 11 CONTINUED

```
AtSQDX-2
   1-50                  tcatatttg aaaaagcact tcttcttctt cttcttcttc ttcttcttct
  51-110   tcttcttccc atcaaaaagt gctagtggca agaccgcgca tattccagta acaaagttta
 111-170   aattcaaaac tatggaacac aatttgtccc atgttttgtt gcctgaatta aacgaccata
 171-230   tcacttggtt cggccacttc atctcggata cgcacaagcg gttgtcaagg ttgtaaaaga
 231-290   cgattttgta aggatctaca ttggcaaagg gagcttaca gacgacttga aaagtttcgg
 291-350   tgtgaagatt gaaaggtaaa actttggttt ctttgcactc ggtgaaccaa taaagcgacc
 351-410   catctagata cacaggtgcg gggtaagcag caatccgata aggagcagcg agagtgacat
 411-470   acctccaagc attggtacta aagtcgaaaa cttcgcatgt agtagcgttt tttaggccta
 471-530   tttctgcaga gttgtataac caaacgggct tgtatgtgcc cctgaatttg tctttaccga
 531-590   atccaagcat aaagaatttg cgtttaagct atctcgtaag atctccatga tcgatcatga
 591-650   gttttgata atcgcaaaga cgttgataac gtagtaacc agtggtcggg ttgaccacat
 651-710   aaccggattt gtcgtgattg ggaagaggcc acaactacta gtgaaacta tgtgaaccta
 711-770   agtacagtac gttatcctt taaagacaa cgagaccgtc gaacgttgat gatgaaccca
 771-830   actgcaatgt tcttaaagat tcccaaggag tagggatctt ggtttataac aatacagaca
 831-890   ccatcagaac atctggatct tctatggtcg cctgattgct gacgatgttt atggtgagga
 891-950   ttatttat taaaaagata aatatcattt tgttggaatt caactaaaat tgtatacatt
 951-1010  taactttaga tatgtaaggg tcgcatatgt atttgattac ggaaaacaaa atctaaaaga
1011-1070  cactttcca ataataaag aaataaagat gttgagtctt attgctatga gtatatgact
1071-1130  aaatttctga tcattaatac aaagaaaaag cctctcataa actaattaag ggtaaataca
1131-1190  cgtaaacatc tccgcagcat actctttaca gccaaagcca cttttactcgc
1191-1250  tccttcagcc acagcaacct ccataaccgc ctctccgcca atctctccgc
1251-1310  aaacccaaac tcatcattca cgtcaaagct tccacatttg gcgcaaacat
1311-1370  cactgttta ccactcaaca tcgcttcat cttgcgtacc tagatgccat
1371-1430  cgttgattc acgaacaaat cgatcccgtt tcaagacctt gtggtctaag ttgggtttag
1431-1490  agatcccaaa atggaaactt tttcccctaa gtagaaaccc ttgagctcat ttgggtttag
```

FIG. 12

```
1491-1550  tccagctact acgaggtaaa catttgaata cgtttggatt attttcgcga aagcttcgaa
1551-1610  gagcaatgga tgtcctttgt ctttgactaa tctcccagca gctcctaaaa caatcgctga
1611-1670  tgagttttct ggtaaccctA attttgacct aaacagagta cgtagcttct tgtctgatgt
1671-1730  gaatccgttc tcgtcgactc cattgaggat cacatgaacc ctttttctcag ggatttggta
1731-1790  aacgtctctt agcatttctc cgcagctatc gctgatagcg atgtggtgag cgtagttgtg
1791-1850  gaagaatctg atttcgtcca gtatcttggg aagcacggca ccgtatagac ttgcattgaa
1851-1910  gccttgtgat cttggttcgt ctggtttacg gatcaggtct tggtaaatac ttgattgtaa
1911-1970  gctctctaac gcaatgccgt gccagatac agcgaggttt ggaacctccc gggcgatcca
1971-2030  gtgaggtaaa gcaacacttt cagagtgaac cgcatcgaaa ggttctttct tgttttcttc
2031-2090  ttggtaaagc tcccatgcct tgttgtaccg ccattttccg gctccgcgt cgccgtgaga
2091-2150  atggattata gggtaaatga tttggtcgga aacaggggg atttgttgg tttcaggggA
2151-2210  ttggtctaag ggagaggtga aaacgtggac acggtgtcca cggcgagcta agccggtgta
2211-2270  tagagtgaag gcgtggcgtt ccatgccgcc aggattggga cccgtgggcc atttccggga
2271-2330  gaaacagcg agttttagtg tttttgggagg agggttggtt aaggagaaat caaggcggtt
2331-2390  ccaggcaaat tgggcggttt ggaggtcgcc agaccacggt ggctggtttg tgtcagagga
2391-2450  ggaggaggag actgcagcgg tggaggagga gcaagtggag gtgcggagga gaaagagagc
2451-2510  cggtatggta aagaggacgg tgaagaagag gaaagtacaa agctaaaaat gagaattagg
2511-2537  tttcttgagt ttggtttgtg aagccat
```

FIG. 12 CONTINUED

```
AtSQDX-3
     1-7                                                                                           ttaaggt
     8-67   ctcatgcatt tgaccagaac atcgacgaat cgcttgtaca tatgttgctt catgtacatt
    68-127  ttctcaacca ttttgcgtcc ttcactcccc aatcgtagcc tctcgtctgg attcctaagt
   128-187  agatacaaga gattatgagc taattctttg ttaccggatc tcccattga gtgaagtaga
   188-247  ccagtcatgt tgtgttgaac catctctttg gttcctcctg catctgttcc caccactgca
   248-307  agtccataag ccattgcttc gattgtcact ctaccaaatg tttcaccaac tccctgtaaa
   308-367  aaatcaaggt tcaaaataaa taaaccgaaa aaaatcgaaa tggtcaaacc gaaatcaaaa
   368-427  cctacatttt gaacaaaaac tttatttgat tgttttatcc aaaaccaaac tgaaatcaat
   428-487  cacaaattgg tttatttgat tcagtaattc aagttcctat aaaactgata aaaactaaacc
   488-547  aaaacctaac tgtaaactac tttctagtgg aaaactgcat atgcatcaaa taatgttttt
   548-607  gaggtgtgag gaggattacc tgggagtttg taacgtagac atctgctgca gagtataatg
   608-667  aagcaacacg ggttgttgca ggagtccaca ttaccgactt agataagttt ccgctgtttg
   668-727  acaagaagct taacatctct ttaacgtatc caactttgtt gctctttgaa cccacggatc
   728-787  ctaaaagaac tttaagttct tgcttctctc ttcttaagcc attgtcaagt gtgagagaaa
   788-847  cacttttcat ctgtcgtgat gaacctctta aacgatgttt gctggagaga ctaacctttt
   848-907  ctttcctaat gatcccctttg tgattccttt gagattcttg tcctctctca gaaagagcca
   908-967  aggcaataga ttcaaggaga agaagttgtc cctttgttgg gttatgctg ctaagagaca
   968-1027 tcacaagcat atctgaatct gttattccta actctgttct cactgattcg cgtaatattt
  1028-1087 gtctcttcac ccctcatttc tctggtgaaa gtgttggtgt gttgagtgaa gaaggaatcc
  1088-1147 ccgctacaaa agctaactca tcattaacag atagtggaac aatcactggt tgtgatctaa
  1148-1207 gctttatatg ctccctccg caccatgtta accattgtct gctctgtgat tcagatataaga
  1208-1267 aaatcagcat tttcactcgg tcaagaactg gtttcgctcg atcaaagtat tctcgtcgat
  1268-1327 tctccattat ccaccaagct atttgacttc caccagctg atgatgattc atgtattgat
```

FIG. 13

```
1328-1387   ctgcgagaaa aggaaaaaaa aaaagtaatt aagatatgct ttcctctgat tgtaaattag
1388-1447   tagtctaaaa actgcataat gaattcttac ctatccatga ggtacacact gctgatcctg
1448-1507   cgatgatcaa atctgctttc atggcagtct tgaagctgag ttctccttg  tcttcaacaa
1508-1567   ctttgatcct tctcctactg tctcctgca  tcaatccacc tctcctgcta agaactactg
1568-1627   cagagactgt tgcaccacag ctcaaaagct ctgaagccag ctccatcata gaaattggag
1628-1687   caccagtcat tgatagctcg tggaaaagca ggacgaatct cctgaccaa  acaaggcgtt
1688-1747   taaaatctga tttcctgtcg caagtcccag atcttctatg cggctccat  tcaagaactt
1748-1807   tatcctctag tgatccaaag ggaccaagaa gcttaccata agtagcattt gtcaatggaa
1808-1867   gttgtggatc ttgctcatca tccaaatcct tagtctcaag tacctcttta atcaccttct
1868-1927   gcttaacacg gatcttacta cgagaagtcc ggacagtttt tctcgtcttc tgcttggaac
1928-1987   tcaagctccg tcgagaaacc ccatcatctt tcttgatcag actaacatcc gtcctcttat
1988-2047   tcgaaccagc atcatcttta taaccaaagc ctcagaattc ctttctcggt ctgcctccaa
2048-2107   caacatccag tcctttaatc ttctccatat ataactcatc cctagactga acataaaatc
2108-2167   accgtaaaaa ctcaactttg ctttcattat catgtgccca caaccggcta ctacgaaacc
2168-2227   caagatacgt ccaaagcgta atcaaaagca gccaataaac taccggagt  cctaccagaa
2228-2287   actgaaacgc tcctcctcca ccatgacctc tacgcggagt cctaccagaa tacactctag
2288-2347   gtgtacccct tggagtagac ctccctgaca gtgaagactt aacacttgtc tgtctcagcg
2348-2369   gcgataaccg aatctcctcc at
```

FIG. 13 CONTINUED

SQD1

```
   1 gtcgaccac gcgtccgctc atctctcatc gttccgggag aagagaagag agacccatcc
  61 ctcacttcaa agttcaaagt ctcgaaggat cttctccaac tctctctaaa caagattcca
 121 aattttcaaa ggtgaatttg tttgatagaa tcaagaacaa acctttaaaa tgcgcatct
 181 actttcagct tcatgccctt cagttatctc acttagcagc agcagcagca agaattcagt
 241 taagccgttt gtttcagggc agacctttctt caatgctcag cttctttcaa gatcttctct
 301 caaaggactt ctcttccaag agaagaaacc gagaaaaagc tgcgttttca gagcaactgc
 361 tgtacctata acccaacaag caccacccga aacatctacc aataactcat cctctaaacc
 421 aaagcgtgtt atggtcattg gtggagatgg ttattgcggt tgggctactg ctctccactt
 481 gtccaagaag aattacgaag tttgcattgt tgacaacctt gtaagacgtc ttttcgacca
 541 ccagcttgga cttgagtcat tgactcctat tgcctccatt catgaccgaa tcagccgatg
 601 gaaggctttg acagggaaat caattgagtt gtacgttggt gatatctgtg atttcgaatt
 661 cttagctgag tctttcaagt cttttgagcc ggattcagtt gtccactttg gggaacagag
 721 atccgctcct tactcgatga cagagcagtc cagagcagtt tatacacagc acaacaatgt
 781 gattggact ctcaacgttc tctttgctat aaaagagttt ggagaggagt gtcatcttgt
 841 aaaacttggg acgatgggtg agtatggaac tccaaatatt gacatcgagg aagttatat
 901 aaccataacc cacaacgta gaactgacac gttgccatac cccaagcaag ctagctcctt
 961 ttatcatctt agcaaagttc atgattcgca caccattgct tttacttgca aggcttgggg
1021 tattagagcc actgatctca accaaggagt tgtttatgga gtgaagactg atgagacaga
1081 gatgcatgag gaactccgta accgactgga ttacgatgct gtgttttgta cagcacttaa
1141 ccggttctgt gtgcaagctg ctgttggtca cccacttaca gtttatggta aaggtggtca
1201 gacgagaggc tacctcgata taagagacac ggttcaatgt gttgagatcg ctatagcaaa
1261 cccggcaaaa gctggtgagt tccggtcett caaccaattt acagaacagt tttcagtcaa
1321 tgaactggct tcactcgtca ctaaagcggg ttcaaagctt ggctagacg tgaaaaagat
1381 gacggtgcct aacccgagag tggaggcaga agaacattac tacaacgcaa agcacactaa
```

FIG. 14

```
1441 gctgatggaa cttggacttg agcctcacta tctatctgac tcacttcttg attcgttgct
1501 caactttgct gttcagttta aagatcgtgt ggacacgaaa caaatcatgc ctagtgtttc
1561 ctggaagaag attggcgtca agactaagtc catgaccaca agtgcag accaatatta
1621 cacataagga gagattatga aagagatgat gtgttgtttg gtatcttcaa acttcatttc
1681 tgcaaaagac ttgctaggct taagaggttt tgtccatatt acattgtgca ggttctttaa
1741 tgttagatct taatttcgat gaaaaaaaaa aaaaaaaaaa aaaaaaaaag ggcggccgc
```

FIG. 14 CONTINUED

```
SQDB
1-25        atggtttctg
26-85       ttgttgacaa  cctcgttcgc  cgcaagacag  acgtggaatt  ggggttcag   ggggttcag
86-145      cgatcgcgac  gattgaacgc  cggttgaagg  catgcaaga   aacgggcggg  cagccgatta
146-205     gctttgtcaa  tctcgactta  gcggctgatt  acgatcgcct  ctgtgcacta  ctgctagaaa
206-265     cgcagccgga  tgcgatcgtg  catttttgccg  aacagcgcgc  cgccccctat  tcaatgaaga
266-325     gtgcatggca  taagcgcttc  acggtcaata  acaacgtcaa  cgcaccac    aatctgctct
326-385     gcgcctgtgt  ggatgtcgc   ctcaagtccc  acattgtcca  cttgggcacc  atgggcgtct
386-445     atggatacgg  tagccatcgc  ggggctacga  tttgaagaga  ctacttagaa  gtggaagtcg
446-505     tccagcggga  tggccaacgc  tttgaagaga  agattcttca  ccccgttgat  ccgggtagcg
506-565     tctatcacat  gaccagacg   ctggatcaat  tgttgttcta  ctactacaac  aagaacgaca
566-625     acatccaagt  caccgaccct  caccagggta  ttgtctgggg  cacgaacacc  gatcactgta
626-685     atctccaccc  ggatctgacc  aatcggttcg  actacgacgg  tgattacggc  acagtcttga
686-745     accgcttctt  gatgcaggcg  gcgatcggct  atccccttgac  tgtgcatggc  gttggtggcc
746-805     aaacccgagc  cttcatccac  attcgcgact  cagtgcgctg  cgtccaactg  gcgatcgaaa
806-865     atccgccagc  agccaatgaa  aaagtccgca  tctttaacca  gatgacgaa   acctaccaag
866-925     tcaaggattt  ggcagagaaa  gtggcggcat  tgaccggtgc  tgaaatcgcc  tacctgccca
926-985     atccacgcaa  ggaagccctt  gagaacgact  tgattgtcga  caaccgctgc  ttgattgatt
986-1045    taggcctcaa  tccgaccacc  ttgacaatg   gcctgatgag  cgaagtggta  gaaattgcgc
1046-1105   agaagtttgc  cgatcgctgc  gatcgcgcca  aaattccctg  cgtttctgcc  tggacccgta
1106-1165   atcaagctga  agctctcagc  gctcctgaaa  ccgctctgcg  ctaa
```

FIG. 15

MAHLLSASCPSVISLSSSSSKNSVKPFVSGQTFFNAQLLSRSSLKGLLFQEKKPRKSC
VFRATAVPITQQAPPETSTNNSSSKPKRVMVIGGDGYCGWATALHLSKKNYEVCIVDN
LVRRLFDHQLGLESLTPIASIHDRISRWKALTGKSIELYVGDICDFEFLAESFKSFEP
DSVVHFGEQRSAPYSMIDRSRAVYTQHNNVIGTLNVLFAIKEFGEECHLVKLGTMGEY
GTPNIDIEEGYITITHNGRTDTLPYPKQASSFYHLSKVHDSHNIAFTCKAWGIRATDL
NQGVVYGVKTDETEMHEELRNRLDYDAVFGTALNRFCVQAAVGHPLTVYGKGGQTRGY
LDIRDTVQCVEIAIANPAKAGEFRVFNQFTEQFSVNELASLVTKAGSKLGLDVKKMTV
PNPRVEAEEHYYNAKHTKLMELGLEPHYLSDSLLDSLLNFAVQFKDRVDTKQIMPSVS
WKKIGVKTKSMTT

FIG. 16

MRIALFTETFLPKVDGIVTRLRHTVDHLQRLGHTVMVFCPDGGLREHKGARVYGVKGF
PLPLYPELKLAFPLPKVGKALERFRPDLIHVVNPAVLGLGGIYYAKALNVPLVASYHT
HLPKYLEHYGLGVLEGVLWELLKLAHNQAAINLCTSTAMVQELTDHGIEHCCLWQRGV
DTETFRPDLATAAMRDRLSGGKPTAPLLLYVGRLSAEKQIDRLRPILDANPEACLALV
GDGPHRAELEQLFAGTQTQFIGYLHGEQLGAAYASADAFVFPSRTETLGLVLLEAMAA
GCPVVAANSGGIPDIVSDGINGFLFDPEDEQGAIAIQRLLANPAEREILRQAARQEA
ERWSWNAATRQLQDYYCEVLADGCLPLAA

FIG. 17

MKILVLGGDGFCGWPCALNLAAAGHAVTIIVDNLVRRKTDVELGVQSLTPIATIERRLK
AWQETGGQPISFVNLDLAADYDRLCALLETQPDAIVHFAEQRAAPYSMKSAWHKRFT
VNNNVNATHNLLCACVDVGLKSHIVHLGTMGVYGYGSHRGATIPEGYLEVEVVQRDGQ
RFEEKILHPVDPGSVYHMTKTLDQLLFYYNKNDNIQVTDLHQGIVWGTNTDHCNLHP
DLTNRFDYDGDYGTVLNRFLMQAAIGYPLTVHGVGGQTRAFIHIRDSVRCVQLAIENP
PAANEKVRIFNQMTETYQVKDLAEKVAALTGAEIAYLPNPRKEALENDLIVDNRCLID
LGLNPTTLDNGLMSEVVEIAQKFADRCDRAKIPCVSAWTRNQAEALSAPETALR

FIG. 18

COMPOSITIONS AND METHODS FOR THE SYNTHESIS AND SUBSEQUENT MODIFICATION OF URIDINE-5'-DIPHOSPHOSULFOQUINOVOSE (UDP-SQ)

FIELD OF THE INVENTION

The present invention relates to compositions and methods for the synthesis and subsequent modification of uridine-5'-diphosphosulfoquinovose (UDP-SQ). The methods of the present invention comprise the utilization of recombinant enzymes from *Arabidopsis thaliana*, UDP-glucose, and a sulfur donor to synthesize UDP-SQ, and the subsequent modification of UDP-SQ to form compounds including, but not limited to, 6-sulfo-α-D-quinovosyl diaclyglycerol (SQDG) and alkyl sulfoquinovoside.

BACKGROUND

Uridine-5'-diphosphosulfoquinovose (UDP-SQ) is a unique sugar nucleotide which carries a negative charge at its sulfonate group. UDP-SQ is believed to react with sugar nucleotide-dependent glycosyltransferases and donate its sulfonate group to other substrates in order to form valuable compounds including, but not limited to, 6-sulfo-α-D-quinovosyl diacyglycerol (SQDG). UDP-SQ is thought to be the direct precursor of SQDG, to which it donates its unique sulfonic acid head group, sulfoquinovose. However, there is not a simple, rapid method of synthesizing UDP-SQ, or an efficient method for subsequent modification of UDP-SQ to compounds including, but not limited to, SQDG and alkyl sulfoquinovoside.

SQDG is an abundant sulfur-containing non-phosphorous glycerolipid that is specifically associated with photosynthetic (thylakoid) membranes of higher plants, mosses, ferns, algae, and most photosynthetic bacteria. SQDG is universally associated with oxygenic photosynthesis and is an important component of the biological sulfur cycle.

SQDG has also been shown to be a potent inhibitor of several mammalian DNA polymerases and Human Immunodeficiency Virus Reverse Transcriptase 1 (HIV-RT1), and as such, is valuable as an anti-viral compound. (Ohta et al., "Sulfoquinovosyldiacylglycerol, KM043, a new potent inhibitor of eukaryotic DNA polymerases and HIV-reverse transcriptase type 1 from a marine red alga, *Gigartina tenella*," *Chem. Pharm. Bull.*, 46(4): 684-86 (1998)). Moreover, SQDG has also been demonstrated to be valuable due to its anti-tumor promoting properties and its ability to enhance the cytocidal effects of anti-cancer chemotherapy agents. (Shirahashi et al., "Isolation and Identification of Anti-tumor-Promoting Principles from the Fresh-Water Cyanobacterium *Phormidium tenue*," *Chem. Pharm. Bull.*, 41(9): 1664-66 (1993)). Furthermore, SQDG is commonly thought to have excellent detergent properties. (Benson, A. A., "The Plant Sulfolipid," *Adv. Lipid Res.*, 1: 387-94 (1963)). Thus, a method of producing UDP-SQ, and its subsequent modification to compounds including, but not limited to, SQDG, is desirable.

Traditionally, UDP-SQ has been synthesized through a series of chemical reactions. (Heinz et al., "Synthesis of different nucleoside 5'-diphospho-sulfoquinovoses and their use for studies on sulfolipid biosynthesis in chloroplasts," *Eur. J. Biochem.*, 184: 445-453 (1989)). However, this chemical production is highly involved, results in low yields of UDP-SQ, and requires several days to complete. (Id.) Moreover, previous studies of SQDG required time-consuming isolation and purification of the anionic sulfolipid from photosynthetic organisms. (Ohta et al., "Action of a New Mammalian DNA Polymerase Inhibitor, Sulfoquinovosyl diacylglycerol," *Biol. Pharm. Bull.*, 22(2): 111-16 (1999); Gustafson et al., "AIDS-Antiviral Sulfolipids From Cyanobacteria (Blue-Green Algae)," *J. Natl. Cancer Inst.*, 81: 1254-258 (1989)). Thus, what is needed is a more simple, rapid method of synthesizing UDP-SQ, and for the subsequent modification of UDP-SQ to compounds including, but not limited to, SQDG.

SUMMARY OF THE INVENTION

The present invention relates to methods for the synthesis and subsequent modification of uridine-5'-diphosphosulfoquinovose (UDP-SQ). The methods of the present invention comprise the utilization of recombinant enzymes from *Arabidopsis thaliana*, UDP-glucose, and a sulfur donor to synthesize UDP-SQ. Unlike the current methods for the synthesis of UDP-SQ, the synthesis methods of the present invention are simple and rapid. Indeed, the production of UDP-SQ by the methods of the present invention can be completed in less than an hour.

In one embodiment, the present invention contemplates a method for synthesizing UDP-SQ comprising: a) providing: i) uridine-5'-diphosphoglucose (UDP-Glc); ii) a sulfur donor; and iii) a peptide capable of catalyzing the conversion of UDP-Glc to uridine-5'-diphosphosulfoquinovose (UDP-SQ); and b) reacting said UDP-Glc with said first peptide and said sulfur donor under such conditions that UDP-SQ is generated.

It is not intended that the present invention be limited by any specific first peptide capable of catalyzing the conversion of UDP-Glc and a sulfur donor to UDP-SQ. In one embodiment, said first peptide is SQD1, a gene product encoded by the nucleic acid sequence set forth in SEQ ID NO: 6.

It is not intended that the present invention be limited by the use of any specific sulfur donor. In one embodiment, the sulfur donor is selected from a group comprising sulfate, sulfite, sulfide, thiosulfate, sulfoglutathione, adenosine 5'-phosphosulfate (APS), and 3'-phosphoadenosine-5'-phosphosulfate (PAPS). In a preferred embodiment, the sulfur donor is sulfite.

It is not intended that the present invention be limited by the use of any specific method to express or produce a peptide capable of catalyzing the conversion of UDP-Glc and a sulfur donor to UDP-SQ. In one embodiment, the present invention contemplates the cloning of the sqd1 gene cDNA into the group of protein expression vectors such as pQE-9, pQE-16, pQE-31, pQE-32, pQE-40, pQE-60, pQE-70, pQE-80, pQE-81, pQE-82, or pQE-100. In another embodiment, the present invention contemplates the cloning of the sqd1 gene cDNA into the protein expression vector, pQE-30. (See FIG. 3).

The methods of the present invention are conveniently carried out in a reaction vessel or container. It is not intended that the present invention be limited to any particular reaction vessel. A variety of containers can be used, including but not limited to tubes, flasks and other glassware.

In an alternative embodiment, the invention contemplates the transformation of plant cells or tissues such that the sqd1 gene product is expressed. In one embodiment, the present invention contemplates the cloning of the sqd1 gene cDNA (SEQ ID NO: 6) into a binary vector for introduction into *Agrobacterium tumefaciens*, and the subsequent generation of transgenic plant cells via Agrobacterial transformation.

It is not intended that the present invention be limited by the use of any specific method to purify a recombinant peptide capable of catalyzing the conversion of UDP-Glc to UDP-SQ. In one embodiment, the present invention contemplates purification of the peptide by use of 6 His-tag incorporated into the protein expression vector that allows protein affinity purification over a nickel-nitriloacetic acid (Ni-NTA) agarose resin-based chromatography column.

It is not intended that the present invention be limited by the use of any specific method for the detection of UDP-SQ synthesis. The present invention contemplates a variety of method, or assay, formats. In one embodiment, an enzyme assay is provided to measure the conversion of UDP-glucose to UDP-SQ as a reflection of the activity of SQD1. In another embodiment, a coupled adenosine 5'-phosphosulfate (APS)/SQD1 assay is contemplated.

The present invention relates to methods for the subsequent modification of uridine-5-diphosphosulfoquinovose (UDP-SQ) to synthesize compounds including, but not limited to, 6-sulfo-α-D-quinovosyl diacylglycerol (SQDG). Unlike the current methods for the synthesis of UDP-SQ, the synthesis methods of the present invention are rapid and simple.

In one embodiment, the present invention contemplates a method for synthesizing UDP-SQ comprising: a) providing: i) uridine-5'-diphosphoglucose (UDP-Glc); ii) a sulfur donor; iii) a first peptide capable of catalyzing the conversion of UDP-Glc to uridine-5'-diphosphosulfoquinovose (UDP-SQ); and iv) a second peptide capable of transferring sulfoquinovose from UDP-SQ onto diacylglycerol; b) reacting said UDP-Glc with said first peptide and said sulfur donor under such conditions that UDP-SQ is generated; and c) treating said UDP-SQ with said second peptide under conditions such that sulfoquinovose diacylglycerol is generated.

It is not intended that the present invention be limited by the use of any specific second peptide capable of transferring sulfoquinovose from UDP-SQ onto diacylglycerol. In one embodiment, said second peptide is a gene product of the nucleic acid sequence set forth in SEQ ID NO: 1 derived from a Cyanobacteria species. In another embodiment, said second peptide is a gene product derived from *Arabidopsis thaliana* and encoded by a nucleic acid sequence selected from the group SEQ ID NO: 3, SEQ ID NO: 4, and SEQ ID NO: 5.

It is not intended that the present invention be limited by the use of any specific method to express or produce a peptide capable of transferring sulfoquinovose from UDP-SQ onto diacylglycerol. In one embodiment, the present invention contemplates the cloning of the sqdX gene into the group of protein expression vectors comprising pQE-9, pQE-16, pQE-31, pQE-32, pQE-40, pQE-60, pQE-70, pQE-80, pQE-81, pQE-82, pQE-100. In another embodiment, the present invention contemplates the cloning of the sqdX gene into the protein expression vector, pQE-30. (See FIG. 3). In a further embodiment, the sqdX gene is cloned into the protein expression vector pACYC184.

In an alternative embodiment, the invention contemplates the transformation of plant cells or tissues such that the sqdX gene product is expressed. In one embodiment, the present invention contemplates the cloning of the sqdX gene cDNA (SEQ ID NO: 1) into a binary vector for introduction into *Agrobacterium tumefaciens*, and the subsequent generation of transgenic plant cells via Agrobacterial transformation. In another embodiment, said gene product is encoded by a nucleic acid sequence selected from the group SEQ ID NO: 3, SEQ ID NO: 4, and SEQ ID NO: 5.

It is not intended that the present invention be limited by the use of any specific method to purify a recombinant peptide capable of transferring sulfoquinovose from UDP-SQ onto diacylglycerol. In one embodiment, the present invention contemplates purification of the peptide by use of 6 His-tag incorporated into the protein expression vector that allows protein affinity purification over a nickel-nitriloacetic acid (Ni-NTA) agarose resin-based chromatography column.

It is not intended that the present invention be limited by the use of any specific method for the detection of SQDG synthesis. The present invention contemplates a variety of assay formats. In one embodiment, the synthesis of SQDG is visualized with iodine vapor and identified by co-chromatography with an *Arabidopsis thaliana* leaf lipid extract known to contain SQDG. In another embodiment, production of SQDG is verified by quantitative analysis wherein reaction products are isolated from the TLC plates and used to prepare fatty acid methyl esters. The methyl esters are quantified by gas chromatography using myristic acid as the internal standard.

It is not intended that the invention be limited to the independent expression of a peptide capable of catalyzing the conversion of UDP-Glc and a sulfur donor to UDP-SQ in a single host organism or plant. Moreover, it is also not intended that the invention be limited to the independent expression of a second peptide capable of transferring sulfoquinovose from UDP-SQ onto diacylglycerol in a single host organism or plant. In one embodiment, the invention contemplates the co-expression of both of the peptides described above in a single host organism. In an alternative embodiment, the invention contemplates the transformation of plant cells or tissues such that both peptides are co-expressed.

The present invention contemplates a method for the modification of UDP-SQ comprising: a) providing: i) uridine-5'-diphosphoglucose; ii) a sulfur donor; iii) a peptide capable of catalyzing the conversion of uridine-5'-diphosphoglucose to uridine-5'-diphosphosulfoquinovose; iv) an acid catalyst; v) a short-chain alcohol; and vi) a long-chain alcohol; b) reacting said uridine-5'-diphosphoglucose with said peptide and said sulfur donor under such conditions that uridine-5'-diphosphosulfoquinovose is generated; c) reacting said uridine-5'-diphosphosulfoquinovose with said short-chain alcohol and said acid catalyst under such conditions that a short-chain alkyl sulfoquinovoside is generated; and d) treating said short-chain alkyl sulfoquinovoside with said long-chain alcohol under such conditions that a long-chain alkyl sulfoquinovoside is generated.

In contrast to current methods for the production of alkyl sulfoquinovoside-like compounds, the method of the present invention produces a group of substances consisting of a glycosidic unit sulfonated at the C-6 position and acetalized at the C-1 position with an alcohol. Moreover, the alkyl sulfoquinovosides produced by the present invention, unlike other anionic surface-active agents, can be obtained from renewable natural resources and are biodegradable.

It is not intended that the invention be limited by the short-chain alcohol chosen for the method. In one embodiment, the short-chain alcohol is selected from the group methanol, ethanol, propanol, pentanol, hexanol, heptanol, octanol, nonanol, including isomers thereof. In another embodiment, the short-chain alcohol is butanol.

It is not intended that the invention be limited by the acid catalyst chosen for the method. In one embodiment, the acid catalyst is selected from the group comprising $H_2SO_4$, HCl, $H_3PO_4$, $BF_3$, ortho-toluenesulfonic acid, meta-toluenesulfonic acid, alkylbenzenesulfonic acid, secondary alkylsulfonic acid, sulfonic resin, alkylsulfate, alkylbenzenesulfonate, alkyl-sulfonate, and sulfosuccinic acid. In another embodiment, the acid catalyst is para-toluenesulfonic acid.

It is not intended that the invention be limited by the long-chain alcohol chosen for the method. In one embodiment, the long-chain alcohol is a fatty alcohol selected from the group of n-dodecyl alcohol, n-tetradecyl alcohol, n-octadecyl alcohol, n-octyl alcohol, n-decyl alcohol, undecyl alcohol, and tridecyl alcohol. In another embodiment, the long-chain alcohol is a technical mixture of about 3 parts by weight lauryl alcohol and 1 part by weight myristyl alcohol. In another embodiment, the long-chain alcohol is a branched-chain primary alcohol including, but not limited to, oxoalcohol. In another embodiment, the long-chain alcohol is n-hexadecyl alcohol.

It is not intended that the invention be limited by the alkyl sulfoquinovoside produced by the method. The present invention contemplates the production of a variety of alkyl sulfoquinovosides and mixtures thereof. In one embodiment, the alkyl sulfoquinovosides produced are comprised of a mixture of short and long-chain alkyl sulfoquinovosides. In another embodiment, alkyl oligosulfoquinovosides are produced. In another embodiment, alkyl polysulfoquinovosides are produced. In a further embodiment, alkyl monosulfoquinovosides are produced.

The present invention also relates to compositions utilized in the biosynthesis of UDP-SQ and its subsequent modification to compounds including, but not limited to, SQDG and alkyl sulfoquinovoside. In one embodiment, the composition is a substantially pure nucleotide sequence comprising at least a portion of SEQ ID NO: 1, SEQ ID NO: 3, SEQ ID NO: 4, or SEQ ID NO: 5. In another embodiment, the composition comprises RNA transcribed from at least a portion of SEQ ID NO: 1, SEQ ID NO: 3, SEQ ID NO: 4, or SEQ ID NO: 5. In another embodiment, the composition comprises protein translated from the RNA transcribed from at least a portion of SEQ ID NO: 1, SEQ ID NO: 3, SEQ ID NO: 4, or SEQ ID NO: 5. In another embodiment, the composition comprises antibodies produced from the translated protein. In a further embodiment, the composition comprises expression constructs comprising at least a portion of SEQ ID NO: 1, SEQ ID NO: 3, SEQ ID NO: 4, or SEQ ID NO: 5. In another embodiment, the composition comprises transgenic plant cells or tissues comprising at least a portion of SEQ ID NO: 1, SEQ ID NO: 3, SEQ ID NO: 4, or SEQ ID NO: 5.

DESCRIPTION OF THE DRAWINGS

FIG. 10 shows the nucleic acid sequence of the Cyanobacterial sqdX gene (SEQ ID NO: 1) (submitted to GenBank data base and assigned accession number U45308, nucleotide numbers 1800-2933). The start and stop codons are highlighted for emphasis.

FIG. 11 shows the genomic nucleic acid sequence of Arabidopsis thaliana containing the AtSQDX-1 gene (SEQ ID NO: 3) (submitted to GenBank data base and assigned accession number AL137189, nucleotide numbers 82324-85302).

FIG. 12 shows the genomic nucleic acid sequence of Arabidopsis thaliana containing the AtSQDX-2 gene (SEQ ID NO: 4) (submitted to GenBank data base and assigned accession number AL021768, nucleotide numbers 1691-4227).

FIG. 13 shows the genomic nucleic acid sequence of Arabidopsis thaliana containing the AtSQDX-3 gene (SEQ ID NO: 5) (submitted to GenBank data base and assigned accession number AC008016, nucleotide numbers 114774-117142).

FIG. 14 shows the nucleic acid sequence of the *Arabidopsis thaliana* SQD1 gene cDNA (SEQ ID NO: 6) (submitted to GenBank data base and assigned accession number AF022082). The start and stop codons are highlighted for emphasis.

FIG. 15 shows the nucleic acid sequence of the Cyanobacterial sqdB gene (SEQ ID NO: 8) (submitted to GenBank data base and assigned accession number U45308, nucleotide numbers 576-1784). The start and stop codons are highlighted for emphasis.

FIG. 16 shows the amino acid sequence of the *Arabidopsis thaliana* SQD1 gene cDNA product (SEQ ID NO: 7) (submitted to GenBank data base and assigned accession number AF022082).

FIG. 17 shows the amino acid sequence of the Cyanobacterial sqdX gene product (SEQ ID NO: 2) (submitted to GenBank data base and assigned accession number U45308).

FIG. 18 shows the amino acid sequence of the Cyanobacterial sqdB gene product (SEQ ID NO: 9) (submitted to GenBank data base and assigned accession number U45308).

DEFINITIONS

Figure 1:
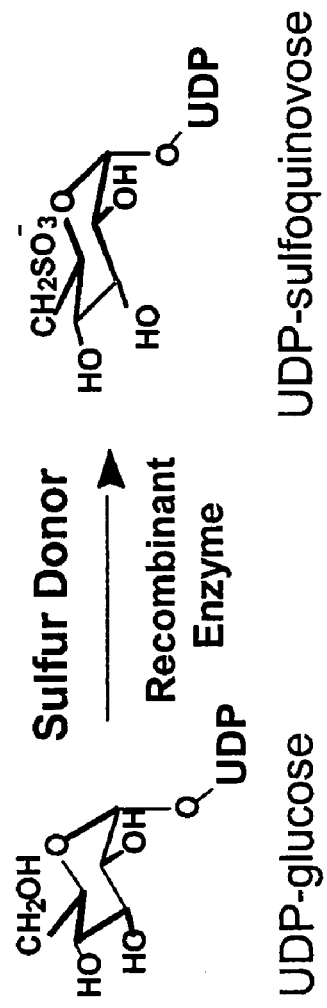
FIG. 1 schematically shows the biochemical pathway for UDP-SQ biosynthesis.

To facilitate understanding of the invention, a number of terms are defined below.

"Associated peptide" as used herein refers to peptides that are bound directly or indirectly to other peptides. Associated peptides that are bound indirectly may have one or more other peptides bound between the two associated peptides. Peptides may be bound via peptide bonds, covalent bonds and non-covalent bonds.

"In operable combination," "in operable order" and "operably linked" as used herein refer to the linkage of nucleic acid sequences in such a manner that a nucleic acid molecule capable of directing the transcription of a given gene and/or the synthe-sis of a desired protein molecule is produced. The term also refers to the linkage of amino acid sequences in such a manner so that a functional protein is produced.

"Expression construct," "expression vector" and "plasmid" as used herein, refer to one or more recombinant DNA or RNA sequences containing a desired coding sequence operably linked to sequences necessary for the expression of the coding sequence in a cell or host organism (e.g., mammal). The sequence may be single or double stranded.

"Reporter construct," "reporter gene" and "reporter protein" as used herein, refer to DNA or amino acid sequences, as appropriate, that, when expressed in a host cell or organism, may be detected, measured or quantitated.

As used herein, the term "purified" or "to purify" refers to the removal of one or more (undesired) components from a sample. For example, where recombinant polypeptides are expressed in bacterial host cells, the polypeptides are purified by the removal of host cell proteins thereby increasing the percent of recombinant polypeptides in the sample.

As used herein, the term "partially purified" refers to the removal of contaminants of a sample to the extent that the substance of interest is recognizable by techniques known to those skilled in the art (e.g., by staining, blotting, etc.) as accounting for a measurable amount (e.g., picograms, nanograms, micrograms, etc.) in the mixture.

As used herein, the term "substantially purified" refers to molecules, (e.g., nucleic or amino acid sequences) that are removed from their natural environment, isolated or separated, and are at least 60% free, preferably 75% free and more preferably 90% free from other components with which they are naturally associated.

As used herein, when a solution passes through the solid support matrix, it comprises the "flow through." Material that does not bind, if present, passes with the solution through the matrix into the flow through. To eliminate all non-specific binding, the matrix is "washed" with one or more wash solutions which, after passing through the matrix, comprise one or more "effluents." "Eluent" is a chemical solution capable of dissociating material bound to the matrix (if any); this dissociated material passes through the matrix and comprises an "eluate."

"Antibody" as used herein, refers to defined as a glycoprotein produced by B cells and plasma cells that binds with high specificity to an antigen (usually, but not always, a peptide) or a structurally similar antigen, that generated its production. Antibodies may be produced by any of the known methodologies and may be either polyclonal or monoclonal.

"Staining," as used herein, refers to any number of processes known to those in the field (typically utilizing dyes) that are used to visualize a specific component(s) and/or feature(s) of a cell or cells.

"Alcohol," as used herein, refers to compounds that have hydroxyl functional groups bonded to saturated, $sp^3$-hybridized carbon atoms. The term "short-chain alcohol," as used herein, refers to alcohols that contain less than 10 carbon atoms. Examples of such short-chain alcohols comprise methanol, ethanol, propanol, butanol, pentanol, hexanol, heptanol, octanol, nonanol, including isomers thereof. The term "long-chain alcohol," as used herein, refers to fatty alcohols, in particular, the higher aliphatic, primary alcohols containing from 10 to 18 carbon atoms, preferably saturated and preferably straight-chain alcohol of the type obtainable by the industrial hydrogenation of native fatty acids. Typical representatives of the higher aliphatic alcohols for example the compounds n-dodecyl alcohol, n-tetradecyl alcohol, n-hexadecyl alcohol, n-octadecyl alcohol, n-octyl alcohol, n-decyl alcohol, undecyl alcohol, tridecyl alcohol.

"Sulfur donor," as used herein, refers to any sulfur-based compound that is capable of providing a sulfonic acid group in the formation of uridine-5-diphospho sulfoquinovose (UDP-SQ). Examples of such sulfur donors comprise sulfate, sulfite, sulfide, thiosulfate, sulfoglutathione, adenosine 5'-phosphosulfate (APS), and 3'-phosphoadenosine-5'-phosphosulfate (PAPS).

"Acid catalyst," as used herein, refers to any acidic compounds including the so-called Lewis acids, which catalyze the acetalization reaction between fatty alcohol and a sugar molecule. Examples of acids used for this purpose in industrial processes comprise mineral acids such as $H_2SO_4$, HCl, $H_3PO_4$ or $BF_3$, or sulfonic acids or their salts. Examples of sulfonic acids comprise ortho-, meta- and para-toluenesulfonic acids, alkylbenzenesulfonic acids, secondary alkyl-sulfonic acids, sulfonic resins, alkylsulfates, alkylbenzenesulfonates, alkyl-sulfonates and sulfosuccinic acid.

"Alkyl sulfoquinovoside," as used herein, refers to a group of substances consisting of a glycosidic unit sulfonated at the C-6 position and acetalized at the C-1 position with an alcohol. In the context of the invention, alkyl sulfoquinovosides are understood to be the reaction products of UDP-sulfoquinovose and fatty alcohols. In its broadest sense, the term "alkyl" in alkyl sulfoquinovosides is intended to encompass the residue of an aliphatic C8-C18 alcohol, obtainable from natural fats, i.e. saturated and unsaturated residues and also mixtures thereof, including those having different chain lengths. The terms alkyl oligosulfoquinovosides, alkyl polysulfoquinovosides apply to alkylated sulfoquinovosides of the type in which one alkyl residue in the form of the acetal is attached to more than one sulfoquinovoside residue, i.e. to a polysulfoquinovoside or oligosulfoquinovoside residue; these terms are regarded as synonymous with one another. Accordingly, alkyl monosulfoquinovoside is the acetal of a monosulfoquinovoside. Since the reaction products of the sugars and the fatty alcohols are generally mixtures, the term alkyl sulfoquinovoside is intended to encompass both alkyl monosulfoquinovosides and also alkyl poly(oligo) sulfoquinovosides.

"Nucleic acid sequence," "nucleotide sequence," and "polynucleotide sequence" as used herein refer to an oligonucleotide or polynucleotide, and fragments or portions thereof, and to DNA or RNA of genomic or synthetic origin which may be single-, or double-stranded, and represent the sense or antisense strand.

As used herein, the terms "oligonucleotides" and "oligomers" refer to a nucleic acid sequence of at least about 10 nucleotides and as many as about 100 nucleotides, preferably about 15 to 30 nucleotides, and more preferably about 20-25 nucleotides, which can be used as a probe or amplimer.

The term "nucleotide sequence of interest" refers to any nucleotide sequence, the manipulation of which may be deemed desirable for any reason, by one of ordinary skill in the art. Such nucleotide sequences include, but are not limited to, coding sequences of structural genes (e.g., enzyme-encoding genes, reporter genes, selection marker genes, oncogenes, drug resistance genes, growth factors, etc.), and of non-coding regulatory sequences that do not encode an mRNA or protein product (e.g., promoter sequence, enhancer sequence, polyadenylation sequence, termination sequence, etc.).

"Amino acid sequence," "polypeptide sequence," "peptide sequence," and "peptide" are used interchangeably herein to refer to a sequence of amino acids.

The term "portion" when used in reference to a nucleotide sequence refers to fragments of that nucleotide sequence. The fragments may range in size from 5 nucleotide residues to the entire nucleotide sequence minus one nucleic acid residue. The term "portion" when used in reference to an amino acid sequence refers to fragments of the amino acid sequence. The fragments may range in size from 3 amino acids to the entire amino acid sequence minus one amino acid residue.

An oligonucleotide sequence which is a "homolog" of a first nucleotide sequence is defined herein as an oligonucleotide sequence which exhibits greater than or equal to 50% identity, and more preferably greater than or equal to 70% identity, to the first nucleotide sequence when sequences having a length of 10 bp or larger are compared.

DNA molecules are said to have "5'ends" and "3'ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5'end" if its 5' phosphate is not linked to the 3' oxygen of a mononucleotide pentose ring. An end of an oligonucleotide is referred to as the "3'end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects that transcription proceeds in a 5' to 3' direction along the DNA strand. The promoter and enhancer elements which direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "cloning" as used herein, refers to the process of isolating a nucleotide sequence from a nucleotide library, cell or organism for replication by recombinant techniques.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed using a recombinant DNA molecule.

As used herein, the terms "vector" and "vehicle" are used interchangeably in reference to nucleic acid molecules that transfer DNA segment(s) from one cell to another.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'," is complementary to the sequence "5'-ACTG-3'." Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands may have significant effects on the efficiency and strength of hybridization between nucleic acid strands. This may be of particular importance in amplification reactions, as well as detection methods which depend upon binding between nucleic acids.

The terms "homology" and "homologous" as used herein in reference to nucleotide sequences refer to a degree of complementarity with other nucleotide sequences. There may be partial homology or complete homology (i.e., identity). A nucleotide sequence which is partially complementary (i.e., "substantially homologous") to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

As used herein the term "stringency" is used in reference to the conditions of temperature, ionic strength, and the presence of other compounds such as organic solvents, under which nucleic acid hybridizations are conducted. "Stringency" typically occurs in a range from about $T_m°$ C. to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" the nucleotide sequence of SEQ ID NO:1, SEQ ID NO:3, SEQ ID NO:4, SEQ ID NO: 5, and SEQ ID NO:6, or portions thereof, will hybridize to its exact complement and closely related sequences.

Low stringency conditions comprise conditions equivalent to binding or hybridization at 68° C. in a solution consisting of 5× SSPE (43.8 g/l NaCl, 6.9 g/l $Na_2PO_4.H_2O$ and 1.85 g/l EDTA, pH adjusted to 7.4 with NaOH), 0.1% SDS, 5× Denhardt's reagent (50× Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 2.0× SSPE, 0.1% SDS at room temperature when a probe of about 100 to about 1000 nucleotides in length is employed.

It is well known in the art that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, conditions which promote hybridization under conditions of high stringency (e.g., increasing the temperature of the hybridization and/or wash steps, the use of formamide in the hybridization solution, etc.) are well known in the art. High stringency conditions, when used in reference to nucleic acid hybridization, comprise conditions equivalent to binding or hybridization at 68° C. in a solution consisting of 5× SSPE, 1% SDS, 5× Denhardt's reagent and 100 µg/ml denatured salmon sperm DNA followed by washing in a solution comprising 0.1× SSPE and 0.1% SDS at 68° C. when a probe of about 100 to about 1000 nucleotides in length is employed.

When used in reference to a double-stranded nucleic acid sequence such as a cDNA or genomic clone, the term "substantially homologous" refers to any probe which can hybridize either partially or completely to either or both strands of the double-stranded nucleic acid sequence under conditions of low stringency as described above.

When used in reference to a single-stranded nucleic acid sequence, the term "substantially homologous" refers to any probe which can hybridize to the single-stranded nucleic acid sequence under conditions of low stringency as described above.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an anti-parallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH (fluorescent in situ hybridization)).

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m 81.5+0.41$(% G+C), when a nucleic acid is in aqueous solution at 1 M NaCl (see e.g., Anderson and Young, Quantitative Filter Hybridization, in Nucleic Acid Hybridization [1985]). Other references include more sophisticated computations which take structural as well as sequence characteristics into account for the calculation of $T_m$.

"Amplification" is defined herein as the production of additional copies of a nucleic acid sequence and is generally carried out using polymerase chain reaction technologies well known in the art (see, e.g., Dieffenbach and Dveksler, *PCR Primer, a Laboratory Manual*, Cold Spring Harbor Press, Plainview N.Y. [1995]). As used herein, the term "polymerase chain reaction" ("PCR") refers to the methods of U.S. Pat. Nos. 4,683,195, 4,683,202, and 4,965,188, all of which are hereby incorporated by reference, which describe a method for increasing the concentration of a segment of a target sequence in a mixture of genomic DNA without cloning or purification. The length of the amplified segment of the desired target sequence is determined by the relative positions of two oligonucleotide primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or DATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

The terms "reverse transcription polymerase chain reaction" and "RT-PCR" refer to a method for reverse transcription of an RNA sequence to generate a mixture of cDNA sequences, followed by increasing the concentration of a desired segment of the transcribed cDNA sequences in the mixture without cloning or purification. Typically, RNA is reverse transcribed using a single primer (e.g., an oligo-dT primer) prior to PCR amplification of the desired segment of the transcribed DNA using two primers.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and of an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double- or single-stranded DNA at or near a specific nucleotide sequence.

As used herein, the term "an oligonucleotide having a nucleotide sequence encoding a gene" means a nucleic acid sequence comprising the coding region of a gene, i.e. the nucleic acid sequence which encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers, promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers, splice junctions, intervening sequences, polyadenylation signals, etc. or a combination of both endogenous and exogenous control elements.

The term "promoter," "promoter element," or "promoter sequence" as used herein, refers to a DNA sequence which when placed at the 5' end of (i.e., precedes) an oligonucleotide sequence is capable of controlling the transcription of the oligonucleotide sequence into mRNA. A promoter is typically located 5' (i.e., upstream) of an oligonucleotide sequence whose transcription into mRNA it controls, and provides a site for specific binding by RNA polymerase and for initiation of transcription.

As used herein, the terms "nucleic acid molecule encoding," "nucleotide encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term "isolated" when used in relation to a nucleic acid, as in "an isolated oligonucleotide" refers to a nucleic acid sequence that is separated from at least one contaminant nucleic acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a polypeptide of interest includes, by way of example, such nucleic acid in cells ordinarily expressing the polypeptide of interest where the nucleic acid is in a chromosomal or extrachromosomal location different from that of natural cells, or is otherwise flanked by a different nucleic acid sequence than that found in nature. The isolated nucleic acid or oligonucleotide may be present in single-stranded or double-stranded form. Isolated nucleic acid can be readily identified (if desired) by a variety of techniques (e.g., hybridization, dot blotting, etc.). When an isolated nucleic acid or oligonucleotide is to be utilized to express a protein, the oligonucleotide will contain at a minimum the sense or coding strand (i.e., the oligonucleotide may be single-stranded). Alternatively, it may contain both the sense and anti-sense strands (i.e., the oligonucleotide may be double-stranded).

As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, post-transcriptional cleavage and polyadenylation.

The term "transgenic" when used in reference to a cell refers to a cell which contains a transgene, or whose genome has been altered by the introduction of a transgene. The term "transgenic" when used in reference to a tissue or to a plant refers to a tissue or plant, respectively, which comprises one or more cells that contain a transgene, or whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods described herein.

The term "transgene" as used herein refers to any nucleic acid sequence which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "foreign gene" refers to any nucleic acid (e.g., gene sequence) which is introduced into the genome of a cell by experimental manipulations and may include gene sequences found in that cell so long as the introduced gene contains some modification (e.g., a point mutation, the presence of a selectable marker gene, etc.) relative to the naturally-occurring gene.

The term "transformation" as used herein refers to the introduction of a transgene into a cell. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (e.g., $\beta$-glucuronidase) encoded by the transgene (e.g., the uid A gene) as demonstrated herein [e.g., histochemical assay of GUS enzyme activity by staining with X-gluc which gives a blue precipitate in the presence of the GUS enzyme; and a chemiluminescent assay of GUS enzyme activity using the GUS-Light kit (Tropix)]. The term "transient transformant" refers to a cell which has transiently incorporated one or more transgenes. In contrast, the term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Alternatively, stable transformation of a cell may also be detected by the polymerase chain reaction of genomic DNA of the cell to amplify transgene sequences. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene.

A "transformed cell" is a cell or cell line that has acquired the ability to grow in cell culture for many multiple generations, the ability to grow in soft agar and the ability to not have cell growth inhibited by cell-to-cell contact. In this regard, transformation refers to the introduction of foreign genetic material into a cell or organism. Transformation may be accomplished by any method known which permits the successful introduction of nucleic acids into cells and which results in the expression of the introduced nucleic acid. "Transformation" methods include, but are not limited to, such methods as microinjection, electroporation, and DNA particle "bombardment." Transformation may be accomplished through use of any expression vector. For example, the use of *Agrobacterium tumefaciens* to introduce foreign nucleic acid into plant cells is contemplated. Additionally, transformation refers to cells that have been transformed naturally, usually through genetic mutation.

The term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens*, (which typically causes crown gall in infected plants), and *Agrobacterium* rhizogens (which causes hairy root disease in infected host plants). Infection of a plant cell with *Agrobacterium* generally results in the production of opines (e.g., nopaline, agropine, octopine, etc.) by the infected cell. Thus, *Agrobacterium* strains which cause production of nopaline (e.g.' strain LBA4301, C58, A208) are referred to as "nopaline-type" *Agrobacteria; Agrobacterium* strains which cause production of octopine (e.g.' strain LBA4404, Ach5, B6) are referred to as "octopine-type" *Agrobacteria*; and Agrobacterium strains which cause production of agropine (e.g., strain EHA105, EHA101, A281) are referred to as "agropine-type" *Agrobacteria*.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are herein incorporated by reference), and are commercially available (e.g., the helium gas-driven microprojectile accelerator (PDS-1000/He) (BioRad).

The term "microwounding" when made in reference to plant tissue refers to the introduction of microscopic wounds in that tissue. Microwounding may be achieved by, for example, particle bombardment as described herein.

The term "plant" as used herein refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including, but not limited to, roots, shoots, leaves, pollen, seeds, tumor tissue and various types of cells in culture (e.g., single cells, protoplasts, embryos, callus, protocorm-like bodies, etc.). Plant tissue may be in planta, in organ culture, tissue culture, or cell culture.

The term "embryonic cell" as used herein in reference to a plant cell refers to one or more plant cells (whether differentiated or un-differentiated) which are capable of differentiation into a plant tissue or plant. Embryonic cells include, without limitation, protoplasts such as those derived from the genera *Fragaria, Lotus, Medicago, Onobrychis, Trifolium*, Trigonella, *Vigna*, Citrus, *Linum*, Geranium, *Manihot, Daucus, Arabidopsis, Brassica, Raphanus*, Sinapis, Atropa, *Capsicum*, Hyoscyamus, *Lycopersicon, Nicotiana, Solanum*, Petunia, Digitalis, Majorana, Ciohorium, *Helianthus, Lactuca, Bromus*, Asparagus, Antirrhinum, Hererocallis, Nemesia, Pelargonium, *Panicum, Pennisetum*, Ranunculus, Senecio, Salpiglossis, *Cucumis*, Browaalia, Glycine, *Lolium, Zea, Triticum, Sorghum*, and *Datura*. Also included are embryos (such as those from sorghum, maize, banana), embryonic meristems (such as those from soybean), embryogenic callus (such as from sugarcane), protocorm-like bodies (such as from pineapple), and embryogenic cells as exemplified by those from garlic. The ability of an embryonic cell to differentiate into a plant is determined using methods known in the art. For example, differentiation of pineapple protocorm-like bodies into shoots may be accomplished by culturing the protocorm-like body on agar-solidified hormone-free modified Murashige & Skoog (MS) medium or on agar-solidified PM2 medium (U.S. Pat. No. 6,091,003 incorporated by reference). Differentiation into pineapple roots may be accomplished by culture of protocorm-like bodies in liquid modified MS medium containing 1 mg/L NAA.

The term "conjugation" as used herein refers to the process in which genetic material is transferred from one microorganism to another involving a physical connection or union between the two cells. This process is commonly known to occur in bacteria, protozoa, and certain algae and fungi.

DETAILED DESCRIPTION OF THE INVENTION

The present invention relates to methods for the synthesis and subsequent modification of uridine-5'-diphospho sulfoquinovose (UDP-SQ).

1. Method for Biosynthesis of Uridine-5'-diphospho Sulfoquinovose (UDP-SQ)

The methods of the present invention comprise the utilization of recombinant enzymes from *Arabidopsis thaliana*, UDP-glucose, and a sulfur donor to synthesize UDP-SQ. Although the present invention is not limited by any specific reaction mechanism, in one embodiment, the production of UDP-SQ from a reaction mixture comprising UDP-glucose, *Arabidopsis thaliana* recombinant SQD1 enzyme protein, and sulfite is contemplated (See FIG. 1).

Biosynthesis of Uridine-5'-diphosphosulfoquinovose (UDP-SQ)

*Arabidopsis thaliana* recombinant SQD1 enzyme protein catalyzes the formation of the sulfonic acid precursor, UDP-SQ, from UDP-glucose and a sulfur donor. In one embodiment, the UDP-SQ production reaction is carried out in a buffer comprising purified SQD1 protein, $Na_2SO_3$, radiolabeled UDP-glucose, and Tris for 40 minutes at 37° C. The reaction mixture is then heat denatured to inactivate the recombinant enzyme, and centrifuged at 10,000×g for 5 minutes. The production of UDP-SQ as a reflection of SQD1 activity is detected as described below.

The biosynthesis of UDP-SQ as contemplated by the present invention is not limited to any specific pH value. In one embodiment, the pH is between 7.0 and 9.5. In a preferred embodiment, the pH of the reaction is 7.5.

Although the present invention is not limited to employing any specific sulfur donor, in one embodiment, the sulfur donor is selected from the group comprising sulfate, sulfide, thiosulfate, sulfoglutathione, adenosine 5'-phosphosulfate (APS), and 3'-phosphoadenosine-5'-phosphosulfate (PAPS). In a preferred embodiment, the sulfur donor is sulfite. (See also, Example 1).

Detection of uridine-5'-diphosphosulfoquinovose (UDP-SQ) produced by the method of the present invention The present invention is not limited by any specific means of detecting UDP-SQ as the end product of the method of biosynthesis described above. In one embodiment, the means for detecting the production of UDP-SQ comprises using high performance liquid chromatography (HPLC) is as follows. For example, the heat denatured reaction mixture is subjected to analysis by HPLC (Waters Corp., Milford, Mass.) employing a Beckman (Fullerton, Calif.) Ultrasphere ODS column (4.6 mm×25 cm, particle size 5 µM) kept at 42° C. Substrates and products are separated by applying a linear gradient of 30 mM $KH_2PO_4$, 2 mM tetrabutylammonium hydroxide (Fisher Scientific, Fair Lawn, N.J.), adjusted to pH 6.0 with KOH, to HPLC grade acetonitrile (EM Science, Gibbstown, N.J.) with a flow rate of 1 ml per minute over 45 minutes. In the HPLC system described above, the major compound produced by the reaction co-chromatographed with authentic UDP-SQ, indicating that this compound was UDP-SQ, and that the purified SQD1 catalyzed the synthesis of the UDP-SQ produced in the assay Production of *Arabidopsis thaliana* Recombinant SQD1 Enzyme Protein Essingman et al., "Phosphate Availability Affects the Thylakoid Lipid Composition and Expression of SQD1, a Gene Required for Sulfolipid Biosynthesis in *Arabidopsis thaliana*," Proc. Natl. Acad. Sci. USA, 95: 1950-955 (1998) discloses the production of *A. thaliana* recombinant SQD1 protein in *Escherichia coli* using a PCR-based strategy, and speculates that SQD1 is involved in the biosynthesis of UDP-SQ from UDP-Glucose.

The present invention is not limited by any particular method for the production of the recombinant SQD1 enzyme used in the production of UDP-SQ. In one embodiment, a means for the production of *Arabidopsis thaliana* recombinant SQD1 enzyme protein, having the amino acid/nucleic acid sequence noted in SEQ ID NO:5, is as follows.

In order to isolate *A. thaliana* genes encoding enzymes involved in the head group biosynthesis of thylakoid membranes, the dbEST database of expressed sequence tags was searched with the predicted amino acid sequence of the bacterial sqdB genes using TBLASTN. Through said search, a partial rice cDNA (EST D46477) was found that encodes a putative protein with high sequence similarity to the bacterial sqdB gene product. (See FIG. 18: SEQ ID NO: 9). A fragment of the partial rice cDNA was used as a probe to screen a *A. thaliana* PRL2 cDNA library by heterologous DNA hybridization. Although the present invention is not limited by any specific hybridization conditions or membranes, in one embodiment, Hybond N+ (Amersham) membranes were used, and hybridization was performed at 53° C. in sodium phosphate buffer (pH 7.2) containing SDS, EDTA, and BSA. After hybridization, the membrane was washed twice for 20 minutes in a SSPE, SDS solution at 53° C. Several cDNA clones were isolated, including one with an insert of 1,799 base-pairs, which was sequenced (GenBank accession No. AF022082)(See FIG. 14: SEQ ID NO: 6). The corresponding locus of *A. thaliana* was designated SQD1 and the plasmid containing the cDNA with the 1,799 bp insert was designated pSQD1. (See also, Example 2.a.).

Figure 3:
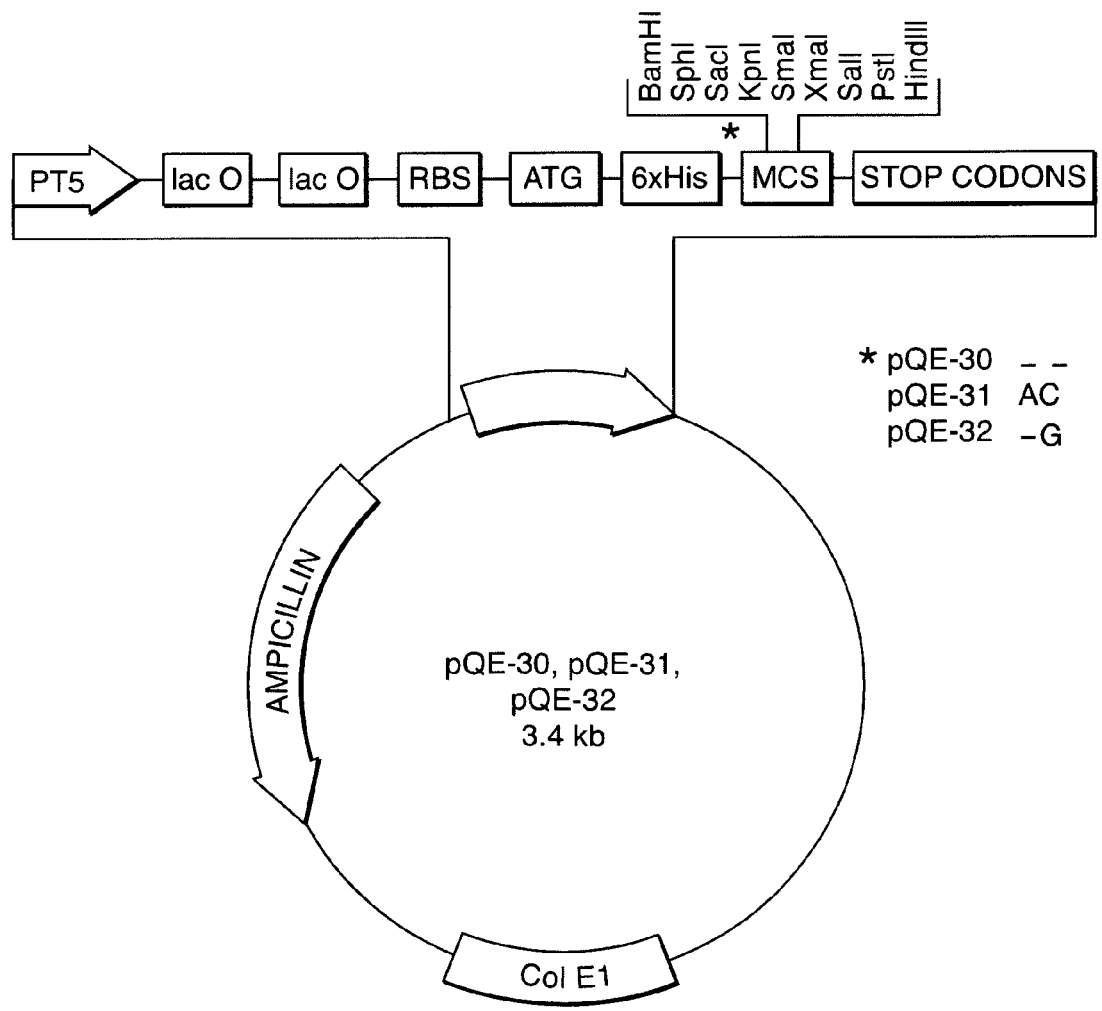
FIG. 3 schematically shows the vector maps, including restriction endonuclease recognition sites, of the protein expression vectors pQE-30, pQE-31 and pQE-32. The nucleotide sequence for the polylinker region of pQE-30 is provided in SEQ ID NO: 22. The nucleotide sequence for the polylinker region of pQE-31 is provided in SEQ ID NO: 23. The nucleotide sequence for the polylinker region of pQE-32 is provided in SEQ ID NO: 24.
Figure 6:
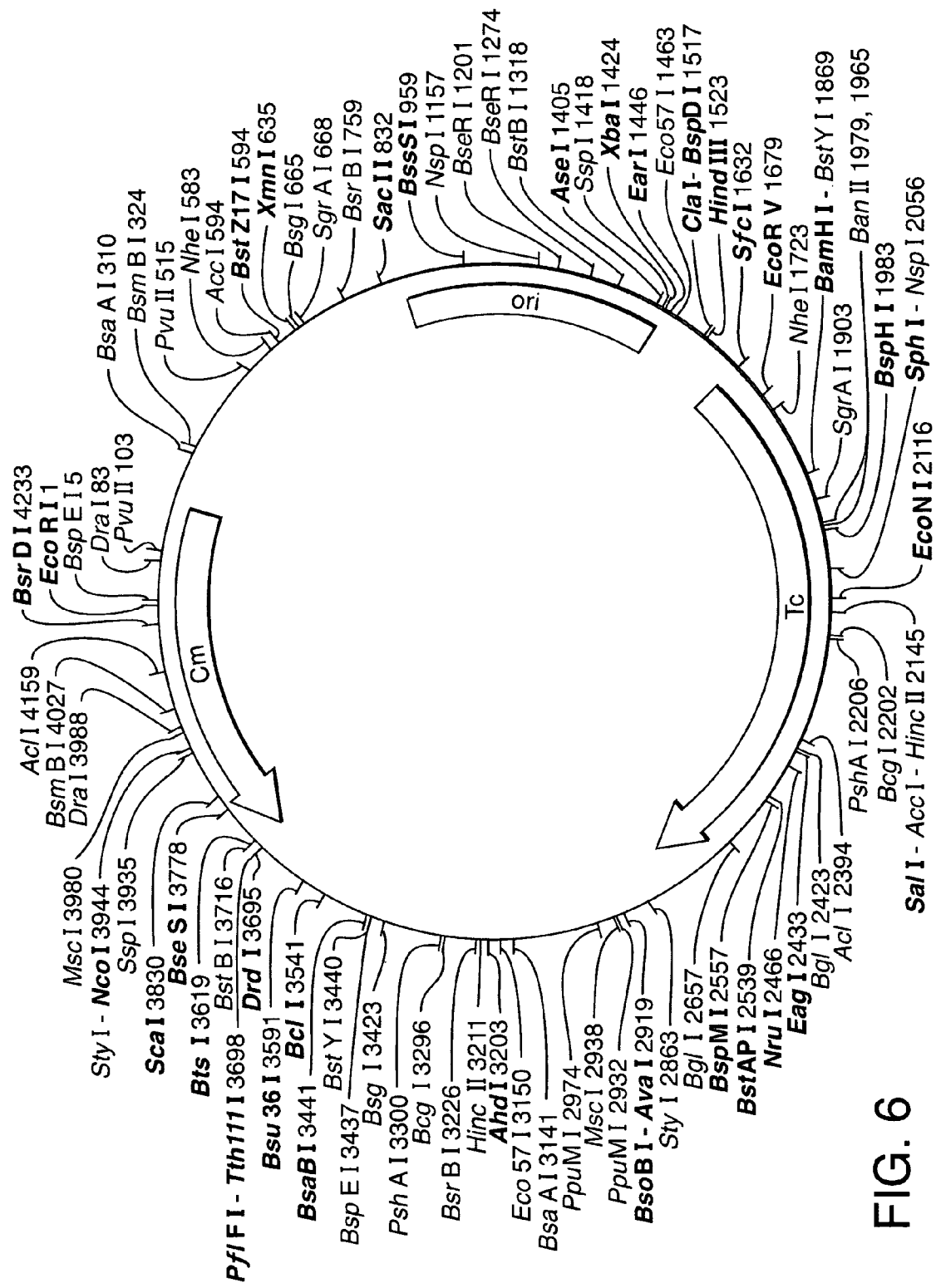
FIG. 6 schematically shows the vector map, including restriction endonuclease recognition sites, of the protein expression vector pACYC184. This plasmid is a small, low copy-number E. coli cloning vector that is 4,244 base pairs in length and carries tetracyclin (base numbers 1580-2770) and chloramphenicol-resistance (base numbers 219-3804) genes. The map shows the location of sites for restriction enzymes that cleave the molecule once or twice; unique sites are shown in bold type. The coordinates refer to the position 5' base in each recognition sequence. Nucleotide number 1 of the vector is the first "G" of the unique EcoR1 site, "GAATTC." The map also shows the relative positions of the antibiotic resistance genes and the origin of DNA replication (ORI) at base numbers 845-847.

The present invention is not limited to any specific means of expressing recombinant SQD1 protein. In one embodiment, in order to express recombinant SQD1 protein in *Escherichia coli*, a fragment of pSQD1 was cloned into the His-tag expression vector, pQE-30 (QIAGEN, Inc., Valencia, Calif.: Cat.# 32149)(See FIG. 3) using a PCR-based strategy. The present invention is not limited to the use of any specific protein expression vector or system. In one embodiment, the protein expression vector is selected from the group comprising pQE-9, pQE-16, pQE-31, pQE-32, pQE-40, pQE-60, pQE-70, pQE-80, pQE-81, pQE-82, pQE-100 (all available from QIAGEN, Inc., Valencia, Calif.). In another embodiment, the protein expression vector is pACYC184 (New England Biolabs, Beverly, Mass.: Cat.# E4152S). (See FIG. 6). In a preferred embodiment, the protein expression vector is pQE-30. (See FIG. 3).

Figure 4:
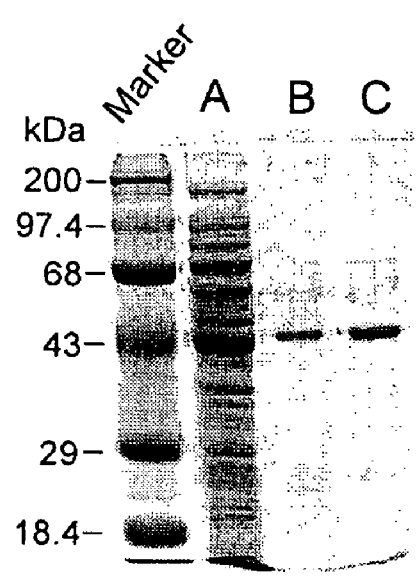
FIG. 4 is a photograph of a sodiumdodecylsulfate polyacrylamide gel electrophroresis (SDS-PAGE) gel showing results of the purification of recombinant SQD1. SDS-PAGE analysis of (A) crude E. coli cell culture extract expressing SQD1 protein and Ni-NTA column purification of (B) SQD1 and (C) Thr145Ala mutant. (4 µg of each).

The present invention is not limited to any specific means of purifying recombinant SQD1 protein. In one embodiment, the resulting plasmid construct, PSQD1-TP, allowed the expression of the recombinant SQD1 protein in *E. Coli* and the purification of the protein due to the selective binding of the six N-terminal histidine residues of the plasmid construct to nickel nitriloacetic acid (Ni-NTA) agarose resin following the manufacturer's instructions. (QIAGEN, Inc., Valencia, Calif.: Cat.# 30210). The recombinant protein was eluted and stored in a buffer comprising glycerol, NaCl, and $NaH_2PO_4$ (pH 7.5) at −20° C. The SQD1 protein was estimated to be approximately 95% pure by SDS-PAGE gel analysis. (See FIG. 4).

Assay for Measuring SQD1 Activity

The present invention is not limited to any specific means of measuring the activity of recombinant SQD1 protein produced by the invention. In one embodiment, an enzyme assay was developed to measure the conversion of UDP-glucose to UDP-SQ as a reflection of SQD1 activity. Basic activity assays were carried out at 37° C. in a reaction mixture containing purified SQD1 protein, $Na_2SO_3$, radiolabeled UDP-glucose, and Tris (pH 7.5) in a total volume of 100 µl for 40 minutes. The reaction mixture was incubated for 10 minutes, heat denatured, centrifuged, and analyzed by HPLC. Substrates and products were separated by applying a linear gradient of $KH_2PO_4$, tetrabutylammonium hydroxide (Fisher Scientific, Fair Lawn, N.J.), adjusted to pH 6.0 with KOH, to HPLC grade acetonitrile (EM Science, Gibbstown, N.J.).

Incubation of the SQD1 protein with labeled UDP-glucose as described above resulted in the formation of two compounds with unique retention times as compared to UDP-glucose as analyzed by HPLC. In the HPLC system described above, one compound co-chromatographed with authentic UDP-SQ, indicating that this compound was UDP-SQ, and that the purified SQD1 catalyzed the synthesis of the UDP-SQ produced in the assay. (See also, Examples 1 & 2.b.).

2. The Biosynthesis of 6-sulfo-α-D-quinovosyl diaclyglycerol (SQDG)

Figure 5:
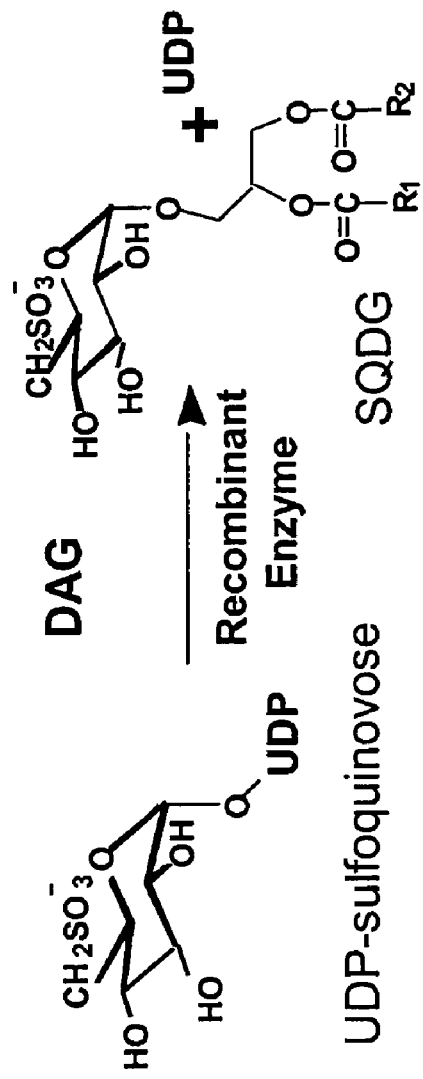
FIG. 5 schematically shows the biochemical pathway for SQDG biosynthesis involving the transfer of sulfoquinovose onto Diacylglycerol (DAG).

The methods of the present invention further comprise the subsequent modification of UDP-SQ to form compounds including, but not limited to, 6-sulfo-α-D-quinovosyl diaclyglycerol (SQDG). Although the present invention is not limited by any specific reaction mechanism, in one embodiment, the production of SQDG from a reaction mixture comprising UDP-SQ, diacylglycerol, and a recombinant peptide capable of transferring sulfoquinovose from UDP-SQ onto diacylglycerol, is contemplated as follows. (See FIG. 5).

In one embodiment, SQDG is produced in a reaction containing means by reacting 100 µM UDP-SQ, 100 µM diacylglycerol, and 10 µg of a substantially purified peptide that is a gene product encoded by the nucleic acid sequence set forth in SEQ ID NO: 1, in a 100 µl reaction volume at 37° C. for 40 minutes. In another embodiment, said peptide is a gene product encoded by the nucleic acid sequence set forth in SEQ ID NO: 3. In another embodiment, said peptide is a gene product encoded by the nucleic acid sequence set forth in SEQ ID NO: 4. In a further embodiment, said peptide is a gene product encoded by the nucleic acid sequence set forth in SEQ ID NO: 5.

Figure 9:
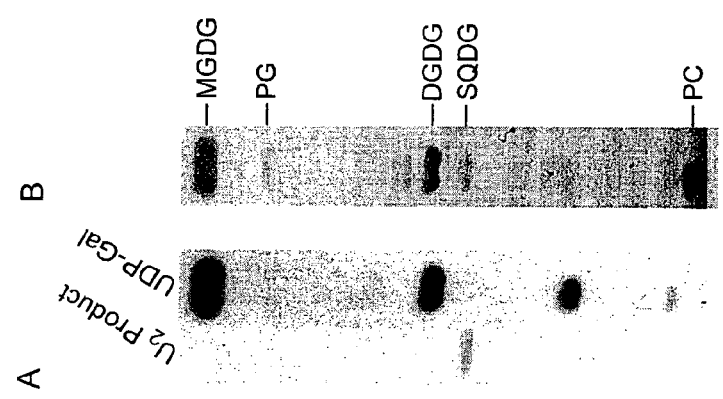
FIG. 9 shows TLC results of an assay of sulfolipid synthase associated with thylakoid membranes which specifically converts UDP-SQ and diacylglycerol to SQDG. (A) Thin-layer chromatography of lipids following the incubation of spinach thylakoid membranes with labeled reaction product U2 or, for control purposes, $^{14}$C-labeled UDP-Gal the substrate for galactolipid biosynthesis. Lipids were visualized by autoradiography. (B) Iodine staining of the U2 lane. DGDG (digalactosyldiacylglycerol); MGDG (monogalactosyldiacylglycerol); PC, (phosphatidylcholine); PG (phosphatidylglycerol); SQDG (sulfoquinovosyldiacylgycerol).

The present invention is not limited by a specific means for verifying the production of SQDG by the method described above. In one embodiment, the production of SQDG is verified by the following means. Aliquots of the above reaction are analyzed by thin layer chromatography (TLC) on activated ammonium sulfate impregnated silica gel TLC plates with a solvent system containing acetone-toluene-water (91:30:8, vol/vol/vol). Products of the above reaction are then visualized with iodine vapor and identified by co-chromatography with an *Arabidopsis thaliana* leaf lipid extract known to contain SQDG. (See FIG. 9). In another embodiment, production of SQDG is verified by quantitative analysis wherein reaction products are isolated from the TLC plates and used to prepare fatty acid methyl esters. The methyl esters are quantified by gas chromatography using myristic acid as the internal standard as described below.

Detection of SQDG Production by Thin Layer Chromatography (TLC)

Randomly chosen colonies from a mutagenized population of *R. sphaeroides* cells known to produce the lipid, SQDG, are streaked as small patches (0.5 by 0.5 cm) on fresh Z-broth plates. Lipids are isolated from these patches by collecting cells onto the wide end of a flat toothpick and swirling the material in 75 µl of chloroform-methanol (1:1, vol/vol) contained in polypropylene microcentrifuge tubes. Following the addition of 25 µl of 1 N KCl-0.2 M $H_3PO_4$, the tubes are vortexed and centrifuged to separate the organic and aqueous phases. A 10 µl aliquot is withdrawn from the lipid-containing lower phase and directly spotted onto an activated ammonium sulfate-impregnated silica gel thin layer chromatography (TLC) plate. For this purpose, Baker Si250 silica plates with a preadsorbent layer are prepared by soaking in 0.15 M ammonium sulfate for 30 seconds followed by air drying to complete dryness. Immediately prior to use, the plates are activated for 2.5 h at 120° C. Activation of ammonium sulfate-treated plates at 120° C. produces sulfuric acid, which protonates phosphatidylglycerol, making it less polar. An acetone-benzene-water mixture (91:30:8, vol/vol/vol) is employed as the solvent system. Lipids were visualized by spraying the plates with 50% sulfuric acid followed by heating at 160° C. for 10 to 15 min to char the lipids.

Quantitative Lipid Analysis to Verify the Production of SQDG

For each strain, three 50-ml cultures were grown in Sistrom's medium aerobically with shaking at 32° C. in the dark. The cells are centrifuged, suspended in 0.5 ml of water, and extracted by vortexing with 4 ml of chloroform-methanol (1:1, vol/vol). Addition of 1.3 ml of 1 M KC1-0.2 M $H_3PO_4$, vortexing, and centrifugation results in phase partitioning of the lipids into the lower chloroform phase. The chloroform phase is removed and concentrated to 0.2 ml by evaporation under a stream of $N_2$. The sample is split, and the material is spotted onto activated (30 min at 110° C.) silica TLC plates (Si250; Baker). The plates are developed in two dimensions, first with chloroform-methanol-water (65:25:4, vol/vol/vol) and then with chloroform-acetone-methanol-acetic acid-water (50:20:10:10:5, by volume).

Lipids are visualized with iodine vapor, and after desorption of iodine, the spots were individually scraped into 8-ml screw-cap tubes. To the samples, 5 µg of myristic acid methyl ester in 0.1 ml of hexane was added as an internal standard, since only negligible amounts of endogenous myristic acid were found in the bacterial lipids. Fatty acid methyl esters are prepared by addition of 1 ml of anhydrous 1 N methanolic HCl (Supelco) followed by incubation at 80° C. for 1 h. Following the addition of 1 ml of 0.95% (wt/vol) KCl, the fatty acid methyl esters were extracted into 1 ml of hexane and then dried to a volume of 0.1 ml.

Samples (2 µl each) are injected onto a gas chromatograph (Varian 2000) which was equipped with a 2.4-m column (2-mm inner diameter) packed with 3% SP-2310 and 2% SP-2300 on 100/120 Chromosorb WAW (Supelco). The carrier gas ($N_2$) flow rate was adjusted to 20 ml/min, and the column temperature was set for 2 min at 180° C., increasing to 200° C. over 10 min, and 4 min at 200° C. The fatty acid methyl esters were detected by a flame ionization detector, and the data were integrated by a Spectra Physics integrator. To calculate the relative amounts of the eight polar lipids included in the analysis, the amount of fatty acids contained in each lipid was calculated. The validity of calculation was based on the assumption that each of the lipids, including the unidentified lipids, contained two fatty acids per molecule and that the different lipids had a similar fatty acid composition.

Production and Purification of a Recombinant Peptide Capable of Transferring Sulfoquinovose from UDP-SQ onto Diacylglycerol a. Cyanobacterial Peptide The invention is not limited to a specific means for the expression of a recombinant peptide capable of transferring sulfoquinovose from UDP-SQ onto diacylglycerol. In one embodiment, a means for the production of a substantially purified peptide encoded by the nucleic acid sequence as set forth in SEQ ID NO: 1, is as follows.

In one embodiment, in order to express recombinant SQDX protein in *Escherichia coli*, a 1,133 base-pair fragment of pSYB (See Example 4) containing nucleotide numbers 1800-2933 of SEQ ID NO: 1 (GenBank Accession No. AF155063) was cloned into the His-tag expression vector, pQE-30 (QIAGEN, Inc., Valencia, Calif.: Cat.# 32149) using a PCR-based strategy. For this purpose, a forward primer having the nucleotide sequence 5'-TTT GGA TCC CGC ATC GCT CTC TTT-3' (SEQ ID NO: 12), and a reverse primer having the nucleotide sequence 5'-ATA AGC TTC GAG CTC AGG CCG CT-3' (SEQ ID NO: 13), were used such that BamHI and HindIII sites were provided for cloning into pQE-30. The forward primer amplifies the beginning of the gene with the omission of the Met start site (ATG) and immediately starts at the second amino acid (See FIG. 17: SEQ ID NO: 2). The reverse primer includes the stop codon of the sqdX gene in the resulting PCR product.

The present invention is not limited to the use of any specific protein expression vector or system. In one embodiment, the protein expression vector is selected from the group comprising pQE-9, pQE-16, pQE-31, pQE-32, pQE-40, pQE-60, pQE-70, pQE-80, pQE-81, pQE-82, pQE-100 (all available from QIAGEN, Inc., Valencia, Calif.). In another embodiment, the protein expression vector is pACYC184 (New England Biolabs, Beverly, Mass.: Cat.# E4152S). (See FIG. 6). In a preferred embodiment, the protein expression vector is pQE-30. (See FIG. 3).

The present invention is not limited to any specific means of purifying recombinant SQDX protein. In one embodiment, the resulting plasmid construct allowed the expression of the recombinant SQDX protein in *E. coli* and the purification of the protein due to the selective binding of the six N-terminal histidine residues of the plasmid construct to Ni-NTA agarose following the manufacturer's instructions. (QIAGEN, Inc., Valencia, Calif.: Cat.# 30210). The recombinant protein was eluted with 200 mM imidazole, which was subsequently removed by use of a Millipore Ultrafree 4 concentrator (Millipore, Inc., Bedford, Mass.). The protein was stored in 20% glycerol, 300 mM NaCl, and 25 mM $NaH_2PO_4$ (pH 7.5) at −20° C.

b. *Arabidopsis* Peptide—Cyanobacteria sqdX Gene Homologs

In another embodiment, the production of a substantially purified, recombinant *Arabidopsis thaliana* peptide capable of transferring sulfoquinovose from UDP-SQ onto diacylglycerol is contemplated. In one embodiment, a means for the production of sqdX gene homologs of *Arabidopsis thaliana* encoded by the nucleic acid sequences as set forth in SEQ ID NO: 3, SEQ ID NO: 4, and SEQ ID NO: 5 is described. A BLAST comparison of the Cyanobacterial sqdX gene to genomic sequence of *Arabidopsis thaliana* revealed several potential homologs. In one embodiment, AtSQDX-1, a homolog having 37% amino acid identity with the Cyanobacterial sqdX gene and a nucleic acid sequence as set forth in SEQ ID NO: 3 is contemplated. In another embodiment, AtSQDX-2, a homolog having 29% amino acid identity with the cyanobacterial sqdX gene is and a nucleic acid sequence as set forth in SEQ ID NO: 4 is contemplated. In a further embodiment, AtSQDX-3, a homolog having 32% amino acid identity with the Cyanobacterial sqdX gene and a nucleic acid sequence as set forth in SEQ ID NO: 5 is contemplated.

Although the present invention is not limited to the expression of any specific *Arabidopsis thaliana* sqdX homolog, in one embodiment, AtSQDX-1 is cloned and expressed as follows.

Total RNA from leaves of two-week old *Arabidopsis* wild-type plants is isolated according to Logemann et al., "Improved Method for the Isolation of RNA from Plant Tissues," *Anal. Biochem.*, 163: 16-20 (1987), as described below. In one embodiment, the *Arabidopsis* leaves are phosphate deprived to enrich for SQDX sequences. The isolated total RNA is then enriched for Poly A+ mRNA using the Oligotex mRNA Mini Kit (QIAGEN Cat. No. 70022) following the manufacturer's instructions as described below. The mRNA is subjected to cDNA biosynthesis using the ProSTAR HF Single-Tube RT-PCR System (Stratagene, LaJolla, Calif.: Cat. No. 600164) following the manufacturer's instructions (as described below) in order to produce a cDNA containing the open reading frame of AtSQDX-1. Primers based on the available genomic sequence of AtSQDX-1 (SEQ ID NO: 3)(GenBank Accession No. AL137189) are designed to allow in-frame cloning into the protein expression vector, pQE-30.

In one embodiment, in order to express recombinant AtSQDX-1 protein in *Escherichia coli*, a 1,410 base-pair fragment of pSYB comprising at least a portion of the nucleic acid sequence set forth in SEQ ID NO: 3 (GenBank Accession No. CAB69850) was cloned into the His-tag expression vector, pQE-30 (QIAGEN, Inc., Valencia, Calif.: Cat.# 32149) using a PCR-based strategy. For this purpose, a forward primer having the nucleotide sequence 5'-CGG GAT CCA TGA CGA CTC TTT CTT CTA TA-3' (SEQ ID NO: 14), and a reverse primer having the nucleotide sequence 5'-AAG GAT CCC TAC ACG TTA CCT TCC GGT A-3' (SEQ ID NO: 15), were used such that a BamHI site was provided for cloning into pQE-30.

The present invention is not limited with respect to any specific primers used to generate an *Arabidopsis thaliana* sqdX homolog. In another embodiment, the forward primer, 5'-AAG GAT CCA TGG CTT CAC AAA CCA AAC T-3' (SEQ ID NO: 16), and the reverse primer, 5'-GCG GAT CCT CAT ATT TTG AAA AAG CAC T-3' (SEQ ID NO: 17), produce the cDNA for the AtSQDX-2 gene. In a further embodiment, the forward primer, 5'-AGG GTA CCA TGG AGG GAT TCG GTT ATC-3' (SEQ ID NO: 18), and the reverse primer, 5'-GCG GTA CCT TAA GGT CTA TGC ATT TGA C-3' (SEQ ID NO: 19), produce the cDNA for the AtSQDX-3 gene.

The present invention is not limited to the cloning of any specific nucleotide sequence into a protein expression vector to produce a recombinant *A. thaliana* peptide capable of transferring sulfoquinovose from UDP-SQ onto diacylglycerol. In one embodiment, a fragment of the AtSQDX-2 gene comprising at least a portion of the nucleic acid sequence as set forth in SEQ ID NO: 4 is cloned into pQE-30. In another embodiment, a fragment of the AtSQDX-3 gene comprising at least a portion of the nucleic acid sequence as set forth in SEQ ID NO: 5 is cloned into pQE-30.

The present invention is not limited to the use of any specific protein expression vector or system. In one embodiment, the protein expression vector is selected from the group pQE-9, pQE-16, pQE-31, pQE-32, pQE-40, pQE-60, pQE-70, pQE-80, pQE-81, pQE-82, pQE-100 (all available from QIAGEN, Inc., Valencia, Calif.). In another embodiment, the protein expression vector is pACYC184. (See FIG. 6). In a preferred embodiment, the protein expression vector is pQE-30. (See FIG. 3).

The present invention is not limited to any specifc means of purifying a recombinant *Arabidopsis thaliana* peptide capable of transferring sulfoquinovose from UDP-SQ onto diacylglycerol recombinant protein. In one embodiment, the resulting plasmid construct allowed the expression of the recombinant AtSQDX-1 protein in *E. coli* and the purification of the protein due to the selective binding of the six N-terminal histidine residues of the plasmid construct to Ni-NTA agarose resin following the manufacturer's instructions. (QIAGEN, Inc., Valencia, Calif.: Cat.# 30210). The recombinant protein was eluted with 200 mM imidazole, which was subsequently removed by use of a Millipore Ultrafree 4 concentrator (Millipore, Inc., Bedford, Mass.). The protein was stored in 20% glycerol, 300 mM NaCl, and 25 mM $NaH_2PO_4$ (pH 7.5) at $-20°$ C.

In another embodiment, purification of a AtSQDX-2 gene product capable of transferring sulfoquinovose from UDP-SQ onto diacylglycerol is contemplated. In a further embodiment, purification of a AtSQDX-3 gene product is contemplated.

Isolation of Total RNA from *Arabidopsis thaliana* Tissues

It is not intended that the invention be limited by any specific method to isolate total RNA from *A. thaliana* tissues. In one embodiment, total RNA is isolated from said tissues by guanidine hydrochloride extraction as follows. Said tissues are frozen in liquid nitrogen and homogenized to a fine powder using a Waring blender. For small amounts of tissue (less than 0.5 g), a rotating pin in a 1.5-ml Eppendorf tube is used to homogenize the tissue. The extract is homogenized further at room temperature by the addition of 2 volumes of a guanidine buffer comprising 8 M guanidine hydrochloride, 20 mM MES (4-morpholineethansulfonic acid), 20 mM EDTA, and 50 mM 2-mercaptoethanol at pH 7.0.

The guanidine hydrochloride extract is centrifuged in a precooled (4° C.) centrifuge for 10 minutes at 10,000 rpm. Subsequently the RNA-containing supernatant is filtered through one layer of cheesecloth to get rid of floating particles. At least 0.2-1.0 vol of phenol/chloroform/IAA is added to extract proteins. After extraction the mixture is centrifuged for 45 minutes at 10,000 rpm at room temperature to separate the phases. The RNA-containing aqueous phase is collected and mixed with precooled 0.7 volumes of ethanol and 0.2 volumes of 1 M acetic acid for precipitating the RNA and leaving DNA and residual proteins in the supernatant. An overnight incubation at $-20°$ C., or a 1 hour incubation at $-70°$ C., is recommended.

The precipitated RNA is pelleted at 10,000 rpm for 10 min and washed twice with sterile 3 M sodium acetate at pH 5.2 at room temperature. Low-molecular-weight RNAs and contaminating polysaccharides dissolve, whereas intact RNA stays as a pellet after centrifugation for 5 minutes at 10,000 rpm. The salt is removed by a final wash with 70% ethanol and the RNA pellet is subsequently dissolved in sterile water and stored at 20° C. until needed.

Poly A+ mRNA Isolation from *Arabidopsis thaliana* Total RNA

The present invention is not limited to any specific means of isolating Poly A+mRNA from the total RNA of *Arabidopsis thaliana* leaves. In one embodiment, Poly A+ mRNA was isolated from *A. thaliana* leaf total RNA with the Oligotex mRNA Mini Kit (QIAGEN Cat. No. 70022) following the manufacturer's instructions as follows.

The Oligotex Suspension is heated to 37° C. in a heating block, mixed by vortexing, and placed at room temperature. A sample containing 0.25 mg of *A. thaliana* leaf total RNA is pipetted into an RNase-free 1.5-ml microcentrifuge tube, and the volume of the reaction is adjusted to 0.25 ml with RNase-free water. A volume of 0.25 ml of Buffer OBB and 0.015 ml of Oligotex Suspension are added to the reaction. The contents are mixed thoroughly by pipetting. The sample incubated for 3 minutes at 70° C. in a water bath or heating block in order to disrupt secondary structure of the RNA. The sample is removed from the heating block, and placed at room temperature (20° to 30° C.) for 10 minutes to allow hybridization between the oligo dT30 of the Oligotex particle and the poly-A tail of the mRNA. The Oligotex:mRNA complex is pelleted by centrifugation for 2 minutes at maximum speed (14,000-18,000×g), and the supernatant is removed by pipetting.

The Oligotex:mRNA pellet is resuspended in 400 µl Buffer OW2 by vortexing, and pipetted onto a small spin column supplied with the kit. The spin column is centrifuged for 1 minute at maximum speed (14,000-18,000×g). The spin column is transferred to a new RNase-free 1.5-ml microcentrifuge tube, and 400 µl of Buffer OW2 is applied to the column. The spin column is centrifuged for 1 minute at maximum speed and the flow-through fraction is discarded.

The spin column is transferred to another 1.5-ml microcentrifuge tube. A volume of 20-100 µl hot (70° C.) Buffer OEB is pipetted onto the column. The resin is resuspended by pipetting up and down three or four times to allow elution of the mRNA, and centrifuged for 1 minute at maximum speed to pellet the suspension. The flow-through fraction, which contains the Poly A+ mRNA isolated, is stored at −20° C. until used.

Biosynthesis of *Arabidopsis thaliana* cDNA

Although the present invention is not limited to any specific method for the biosynthesis of *Arabidopsis thaliana* cDNA, in one embodiment, said cDNA was biosynthesized using the ProSTAR HF Single-Tube RT-PCR System (Stratagene, LaJolla, Calif.: Cat. No. 600164) as follows.

Control and experimental reactions are prepared by adding the following components to separate sterile 0.5-ml microcentrifuge tubes in order:

Control Reaction 40.5 µl of RNase-free water (not DEPC-treated water)

5.0 µl of 10× HF RT-PCR buffer 1.0 µl of control primer set (200 ng/µl)

1.0 µl of dNTP mix (40 mM)

1.0 µl of control mRNA

Experimental Reaction 39.5 µl of RNase-free water (not DEPC-treated water)

5.0 µl of 10× HF RT-PCR buffer 1.0 µl of forward primer (100 ng)

1.0 µl of reverse primer (100 ng)

1.0 µl of dNTP mix (40 mM)

1.0 µl (0.1-10 ng) of isolated Poly A+ mRNA.

Just before use, 0.5 µl of StrataScript RT (20 U/µl) is diluted to a 8.0 pl final volume with 6.7 µl of RNase-free water and 0.8 µl of 10× HF RT-PCR buffer. A volume of 1.0 µl of the diluted StrataScript RT is added to each reaction. A volume of 0.5 µl of TaqPlus Precision DNA polymerase mixture is then added to each reaction. The reaction is vortexed gently without creating bubbles. Both the control and experimental reactions a placed in a GeneAmp PCR System 9600 thermal cycler (Applied Biosystems, Foster City, Calif.: Cat.# N801-0001). The reaction is then subjected to the following thermal-cycling program to both synthesize first-strand cDNA from the mRNA template and to amplify the cDNA via PCR: 1 cycle at 42° C. for 30 minutes; 1 cycle at 95° C. for 1 minute; 40 cycles comprised of 95° C. for 30 seconds, 60° C. for 30 seconds, and 68° C. for 2 minutes; and 1 cycle at 68° C. for 10 minutes.

Upon completion of the thermal-cycling program, the RT-PCR products are analyzed by 1.0% (w/v) agarose gel electrophoresis. RT-PCR amplification of the control reaction, which contains the control mRNA and the control primer set, yields a 500 base pair product. The reaction products will be readily visible by UV transillumination of the ethidium bromide-stained agarose gel. The products containing the cDNA produced by the above reaction are stored at −20° C. until needed.

Co-Expression of *Arabidopsis thaliana* Recombinant Peptides

It is not intended that the invention be limited to the independent expression of a peptide capable of catalyzing the conversion of UDP-Glc and a sulfur donor to UDP-SQ in a single host organism or plant. Moreover, it is also not intended that the invention be limited to the independent expression of a second peptide capable of transferring sulfoquinovose from UDP-SQ onto diacylglycerol in a single host organism or plant. In one embodiment, the invention contemplates the co-expression of both of the peptides described above in a single host organism or plant. In one embodiment, co-expression of the peptides SQD1 and SQDX (for example, in separate protein expression vectors) in *E. coli*, such that the sulfolipid biosynthetic pathway is reconstituted, is contemplated as follows.

In order to express two proteins in *E. coli*, two compatible plasmids with the ability to express proteins, one for SQD1 and one for SQDX, are utilized. Each plasmid must have a different antibiotic resistance in order to select for transformants with the correct combination of plasmids. The plasmid pQE-30 provides ampicillin resistance, whereas the plasmid, pACYC184, provides chloramphenicol resistance. The SQD1 coding region, along with the protein expression cassette of pQE-30, is removed from this plasmid using the restriction enzymes Xho I and Pvu II, and ligated into the pACYC184 plasmid (New England Biolabs, Beverly, Mass.: Cat.# E4152S) (See FIG. 6) cut with Sal I and EcoR V. The M15 cell line (QIAGEN, Inc., Valencia, Calif.) is transformed with a pQE-30/SQDX protein expression construct (as described above). The SQD1/pACYC184 expression construct is transformed into the M15 cell line containing the pQE-30/SQDX expression vector. Upon induction of expression with 1-5 mM isopropyl-β-D-thiogalactoside (IPTG)(Amersham Pharmacia Biotech, Piscataway, N.J.: Cat.# 27-3054-03), both proteins are expressed.

The present invention is not limited to the use of any specific protein expression vector to produce co-expression of the two recombinant peptides. In one embodiment, the protein expression vector is selected from the group comprising pBK-CMV (Stratagene, LaJolla, Calif.: Cat.# 212209), pGEX-6P-1 (Amersham Pharmacia Biotech, Piscataway, N.J.: Cat.# 27-4597-01), or pUC19 (New England Biolabs, Beverly, Mass.: Cat.# N3041S).

Expression of *Arabidopsis thaliana* Recombinant Peptides in Transgenic Plants

Transfer and expression of transgenes in plant cells is now routine practice to those skilled in the art. It has become a major tool to carry out gene expression studies and to attempt to obtain improved plant varieties of agricultural or commercial interest. The present invention is not limited to the expression of a first peptide capable of catalyzing the conversion of UDP-Glc and a sulfur donor to UDP-SQ in a single host organism, or a second peptide capable of transferring sulfoquinovose from UDP-SQ onto diacylglycerol, in bacterial cells. The invention contemplates the expression of *Arabidopsis thaliana* recombinant peptides in transgenic plants as described by S. Clough and A. Bent, "Floral dip: a simplified method for *Agrobacterium*-mediated transformation of *Arabidopsis thaliana*," Plant J, 16: 735-43 (1998). (See Example 3).

In one embodiment, the general process for manipulating genes to be transferred into the genome of plant cells to result in the expression of a recombinant peptide is carried out in two phases. First, all the cloning and DNA modification steps are done in *E. coli*, and the plasmid containing the gene construct of interest is transferred by conjugation into *Agrobacterium*. Second, the resulting *Agrobacterium* strain is used to transform plant cells. Thus, for the generalized plant expression vector, the plasmid contains an origin of replication that allows it to replicate in *Agrobacterium* and a high copy number origin of replication functional in *E. coli*. This permits facile production and testing of transgenes in *E. coli* prior to transfer to *Agrobacterium* for subsequent introduction into plants. Resistance genes can be carried on the vector, one for selection in bacteria (e.g., streptomycin), and the other that will express in plants (e.g., a gene encoding for kanamycin resistance or a gene encoding for resistance to an herbicide such as hygromycin). Also present are restriction endonuclease sites for the addition of one or more transgenes operably linked to appropriate regulatory sequences and directional T-DNA border sequences which, when recognized by the transfer functions of *Agrobacterium*, delimit the region that will be transferred to the plant.

In another embodiment, plant cells may be transformed by shooting into the cell, tungsten microprojectiles on which cloned DNA is precipitated. (See, e.g., Gordon-Kamm et al., *Plant Cell*, 2: 603 (1990)). In one embodiment, the Biolistic Apparatus (Bio-Rad, Hercules, Calif.) is used for the shooting with a gunpowder charge (22 caliber Power Piston Tool Charge) or an air-driven blast driving a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to go through. As a result, the plastic macroprojectile smashes against the stopping plate and the tungsten microprojectiles continue toward their target through the hole in the plate. For the present invention the target can be any plant cell, tissue, seed, or embryo. The DNA introduced into the cell on the microprojectiles becomes integrated into either the nucleus or the chloroplast.

It is not intended that the present invention be limited to the particular manner by which the expression of any specific recombinant *A. thaliana* peptide in plants is achieved. In one embodiment, a peptide encoded by the nucleic acid sequences as set forth in SEQ ID NO: 6 is expressed in plants. In another embodiment, a peptide encoded by the nucleic acid sequence as set forth in SEQ ID NO: 1, SEQ ID NO: 3, SEQ ID NO: 4, or SEQ ID NO: 5 is expressed in plants. In a further embodiment, two recombinant *A. thaliana* peptides encoded by the group of nucleic acid sequences comprising SEQ ID NO: 1, SEQ ID NO: 3, SEQ ID NO: 4, SEQ ID NO: 5, and SEQ ID NO: 6 are co-expressed in plants.

It is not intended that the present invention be limited by any particular plant. cell type in which to generate the expression of *Arabidopsis thaliana* recombinant peptides. In one embodiment, the plant cell is derived from a monocotyledonous plant. In an alternative embodiment, the plant cell is derived from a dicotyledonous plant. In another embodiment, the plant cell is derived from a group comprising the genera *Anacardium, Arachis*, Asparagus, Atropa, *Avena, Brassica*, Citrus, *Citrullus, Capsicum, Carthamus*, Cocos, *Coffea, Cucumis, Cucurbita, Daucus*, Elaeis, *Fragaria*, Glycine, *Gossypium, Helianthus*, Heterocallis, *Hordeum*, Hyoscyamus, *Lactuca, Linum, Lolium*, Lupinus, *Lycopersicon, Malus, Manihot*, Majorana, *Medicago, Nicotiana, Olea, Oryza*, Panieum, Pannesetum, *Persea, Phaseolus*, Pistachia, *Pisum, Pyrus, Prunus, Raphanus, Ricinus, Secale*, Senecio, Sinapis, *Solanum, Sorghum*, Theobromus, Trigonella, *Triticum, Vicia, Vitis, Vigna*, and *Zea*. In a preferred embodiment, the plant cell is derived from *Arabidopsis thaliana*.

3. Subsequent Modification of UDP-SQ to Produce Alkyl Sulfoquinovosides

Figure 7:
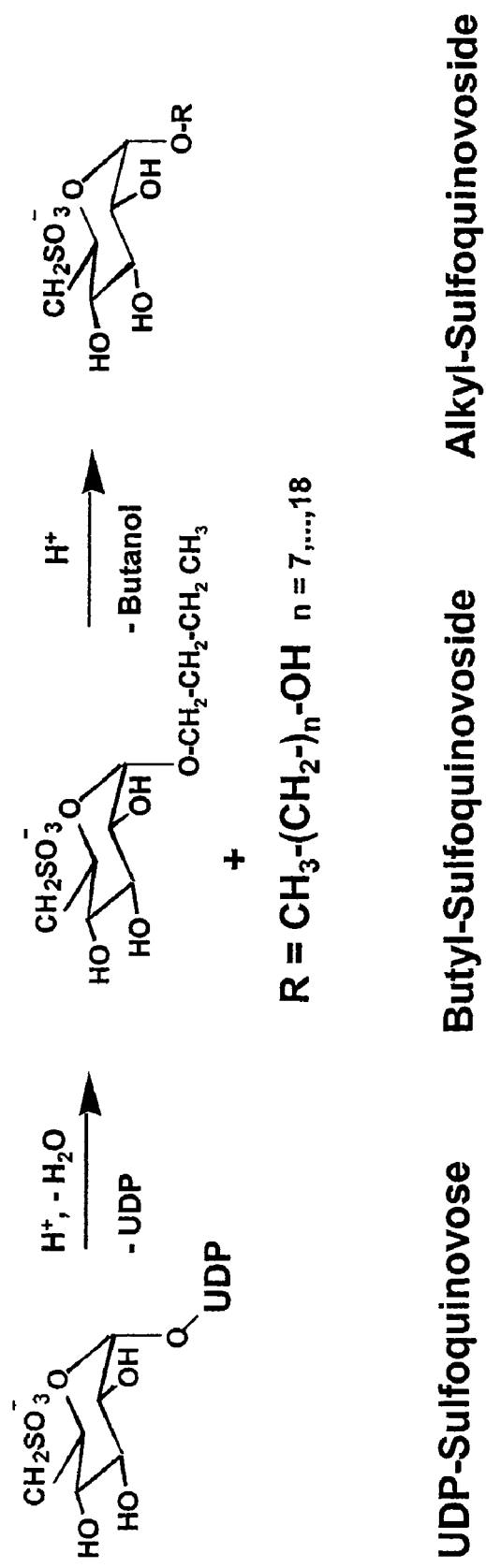
FIG. 7 schematically shows one embodiment for the chemical modification of UDP-SQ with short and long-chain alcohols and an acid catalyst to produce alkyl sulfoquinovoside.

The methods of the present invention further comprise the subsequent modification of UDP-SQ to form compounds including, but not limited to, alkyl sulfoquinovoside. (See FIG. 7). The method of the invention is not limited to the production of alkyl sulfoquinovosides. Furthermore, the present invention is not limited by any specific reaction mechanism. In one embodiment, the present invention relates to a process for the production of alkyl sulfoquinovosides by reacting of a short-chain alcohol with sulfoquinovose resulting from the hydrolytic cleavage of UDP-sulfoquinovose in the presence of a suitable acid catalyst with elimination of water. The short-chain alkyl sulfoquinovoside is then transacetalized with a long-chain alcohol to form long-chain sulfoquinovosides.

Although the method of the invention is not limited with respect to the structure of the alkyl sulfoquinovoside produced, in one embodiment, alkyl sulfoquinovosides are a group of substances consisting of a glycosidic unit sulfonated at the C-6 position and acetalized at the C-1 position with an alcohol. In another embodiment, alkyl sulfoquinovosides are understood to be the reaction products of UDP-sulfoquinovose and fatty alcohols. In a preferred embodiment, the term "alkyl" in alkyl sulfoquinovosides is intended to encompass the residue of an aliphatic C8-C18 alcohol, preferably a fatty alcohol, obtainable from natural fats (i.e. saturated and unsaturated residues and also mixtures thereof, including those having different chain lengths).

The terms alkyl oligosulfoquinovosides and alkyl polysulfoquinovosides apply to alkylated sulfoquinovosides in which one alkyl residue in the form of the acetal is attached to more than one sulfoquinovoside residue (i.e. to a polysulfoquinovoside or oligosulfoquinovoside residue). Accordingly, alkyl monosulfoquinovoside is the acetal of a monosulfoquinovoside. Since the reaction products of the sugars and the fatty alcohols are generally mixtures, the term alkyl sulfoquinovoside is intended to encompass both alkyl monosulfoquinovosides and also alkyl poly(oligo) sulfoquinovosides.

In one embodiment, the synthesis of alkyl sulfoquinovose is carried out by the transacetalization method with a short-chain alcohol. Although it is not intended that the methods recited by the present invention be limited to any particular short-chain alcohol, in one embodiment, the short-chain alcohol is selected from a group comprising methanol, ethanol, propanol, pentanol, hexanol, heptanol, octanol, nonanol, including isomers thereof. In a preferred embodiment, the short-chain alcohol is butanol.

In one embodiment, the synthesis of alkyl sulfoquinovosides starts from the hydrolytic cleavage of the UDP-Sulfoquinovose. Sulfoquinovose is then refluxed with an acidic catalyst in butanol, the water of the reaction is removed by distillation under vacuum. The purpose of the acid catalyst is to favor the reactions which involve the glucosidic bond.

Although it is not intended that the method of the invention be limited to any particular acid catalyst, in one embodiment, any acidic compound (including the so-called Lewis acids which catalyze the acetalization reaction between fatty alcohol and the sugar molecule) may be used as catalysts. In one embodiment, the acid catalyst is a mineral acids comprising $H_2SO_4$, HCl, $H_3PO_4$ or $BF_3$. In another embodiment, the acid catalyst is a sulfonic acid or its salt, comprising ortho-toluenesulfonic acid, meta-toluenesulfonic acid, alkylbenzenesulfonic acid, secondary alkyl-sulfonic acid, sulfonic resin, alkylsulfate, alkylbenzenesulfonate, alkyl-sulfonate and sulfosuccinic acid. In a more preferred embodiment, the acid catalyst is para-toluenesulfonic acid.

Although it is not intended that the method of the invention be limited to a particular set of reaction conditions, in one embodiment, the reflux temperature is 118° C.; a vapor temperature of 95 to 110° C. is established with the formation of the lower boiling butanol/water mixture; the acetalization with the butanol is carried out under light vacuum (i.e. under a pressure of 800 to 950 mbar); and an azeotropic amount of butanol is removed with the water.

In one embodiment, the butyl sulfoquinovoside is subsequently treated under vacuum with the long-chain alcohol, in the presence of the acidic catalyst. In one embodiment, it is preferable to reduce the content of butyl sulfoquinovoside by removing butanol by distillation under reduced pressure of 10 mbar. In one embodiment, neutralization of the catalyst following the removal of butanol is preferably separated by an interim period of up to about 1 hour, under which the reaction mixture is stirred under normal pressure at temperatures of from 100 to 115° C. In this manner, the reaction of the butyl sulfoquinovoside with the fatty alcohol can be continued under control.

Although it is not intended that the method of the invention be limited to a particular long-chain alcohol, in one embodiment, the long-chain alcohol is a fatty alcohol; more preferably, a higher aliphatic, primary alcohol containing from 8 to 18 carbon atoms; and even more preferably, a saturated and preferably straight-chain alcohol of the type obtainable by the industrial hydrogenation of native fatty acids. In one embodiment, the higher aliphatic alcohol is selected from a group comprising n-dodecyl alcohol, n-tetradecyl alcohol, n-octadecyl alcohol, n-octyl alcohol, n-decyl alcohol, undecyl alcohol, tridecyl alcohol. In another embodiment, the long-chain alcohol is a technical mixture of about 3 parts by weight lauryl alcohol and 1 part by weight myristyl alcohol. In another embodiment, the long-chain alcohol is a branched-chain primary alcohol including, but not limited to, oxoalcohol. In a preferred embodiment, the long-chain alcohol is n-hexadecyl alcohol.

Although it is not intended that the method of the invention be limited to a particular set of reaction conditions, in one embodiment, the reaction mixture comprising short and long chain alkyl sulfoquinovosides, a long chain alcohol, and an acid catalyst, is subsequently cooled to a temperature below 95° C. In one embodiment, the acidic catalyst is subsequently neutralized by the addition of a base and the adjustment of the pH of the neutralized reaction mixture to a pH of at least 8. In a preferred embodiment, the pH of the neutralized reaction mixture is 8.5.

Although it is not intended that the method of the invention be limited to a particular base, in one embodiment, the base is selected from a group of organic or inorganic basic materials comprising the alkali metal bases such as alkali metal hydroxide, carbonates, and bicarbonates. In another embodiment, the base is selected from a group comprising the alkaline earth bases such as calcium oxide and magnesium oxide. In another embodiment, aluminum bases such as aluminum hydroxide or its basic alkali aluminum components are contemplated. In a further embodiment, the base is selected from a group comprising ammonia-based compounds, such as ammonium hydroxide, and amines including, but not limited to, primary, secondary tertiary and heterocyclic amines.

Although it is not intended that the method of the invention be limited to a particular temperature range for filtering the reaction mixture, in one embodiment, the reaction mixture is filtered at a temperature of from 80 to 90° C., and the excess fatty alcohol is removed by distillation at to a level below 5% by weight. In one embodiment, the sump temperature must be kept at levels at which the alkyl sulfoquinovoside is thermally stable. In a preferred embodiment, the sump temperature should not exceed a value of 160° C.

Although the method of the invention is not limited to producing a product of any particular content of short and long chain alkyl sulfoquinovosides, in one embodiment, the product obtained has a high content of the long-chain alkyl sulfoquinovoside and low content of the butyl sulfoquinovoside, alkyl monosulfoquinovosides, and also alkyl poly (oligo) sulfoquinovosides.

Alkyl sulfoquinovosides are anionic surface-active agents that are suitable for use as industrial surfactants for the manufacture of detergents and cleaning preparations. Biermann et al., U.S. Pat. No. 5,374,716, teaches a process for the production of surface-active alkyl glycosides. Miyano, M. & Benson, A. A., "The Plant Sulfolipid VII. Synthesis of 6-sulfo-α-D-quinovopyranosyl-(1→1')-glycerol and Radiochemical Synthesis of Sulfolipids," *J. Am. Chem. Soc.,* 84: 59-62 (1962) teaches the preparation of 6-sulfo-D-quinovose from 1,2-isopropylidene-6-O-osyl-D-glucofuranose by sulfate replacement, its subsequent conversion to an allyl α-glycoside, and its oxidation by permanganate to form sulfoquinovosyl glycerol. Roy, A. B. & Hewlins, J. E., "Sulfoquinovose and its aldonic acid: their preparation and oxidation to 2-sulfoacetaldehyde by periodate," *Carbohydrate Res.,* 302: 113-17 (1997) teaches the preparation of 2-sulfoacetaldehyde by the oxidation of sulfoquinovose, or its aldonic acid, with periodate.

EXPERIMENTAL

Example 1

In this example, a means for the production of UDP-SQ from a reaction mixture comprising UDP-glucose, *Arabidopsis thaliana* recombinant SQD1 enzyme protein, and sulfite is described. In one embodiment, the UDP-SQ production reaction is carried out at 37° C. in a buffer containing 10 μg purified SQD1 protein, 100 μM $Na_2SO_3$, 2.2 mM UDP-glucose [$^{14}$C(U)-glucose](69 Bq/nmol) and 50 mM Tris (pH 7.5) in a total volume of 100 μl for 40 minutes. The reaction mixture is then heat denatured 5 minutes at 95° C. to inactivate the recombinant enzyme, centrifuged at 10,000× g for 5 minutes, and analyzed by high performance liquid chromatography (HPLC) (Waters Corp., Milford, Mass.) employing a Beckman (Fullerton, Calif.) Ultrasphere ODS column (4.6 mm×25 cm, particle size 5 μM) kept constantly at 42° C. Substrates and products were separated by applying a linear gradient of 30 mM $KH_2PO_4$, 2 mM tetrabutylammonium hydroxide (Fisher Scientific, Fair Lawn, N.J.), adjusted to pH 6.0 with KOH, to HPLC grade acetonitrile (EM Science, Gibbstown, N.J.) with a flow rate of 1 ml per minute over 45 minutes.

Figure 2:
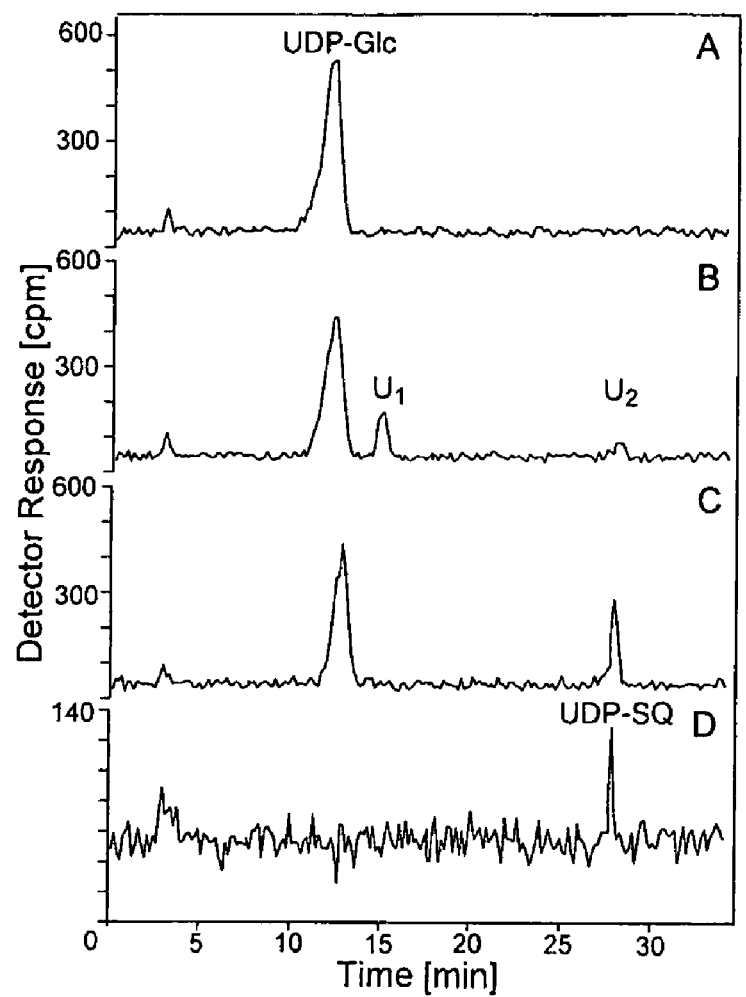
FIG. 2 is a chromatograph showing the results of an assay to detect the conversion of UDP-Glc by SQD1. The chromatographic analysis of $^{14}$C-labeled substrate and reaction products by HPLC is shown (A-C). (A) UDP-Glc without SQD1 protein, (B) UDP-Glc and SQD1 protein, (C) UDP-Glc, SQD1 protein, and sulfite, (D) authentic $^{35}$S-labeled UDP-SQ isolated from the sqdD mutant of the cyanobacterium, R. sphaeroides. U1 and U2, products as described in the text.

Incubation of the SQD1 protein with labeled UDP-glucose as described above resulted in the formation of two compounds ($U_1$ and $U_2$) with unique retention times as compared to UDP-glucose (See FIGS. 2A & B) as analyzed by HPLC. Filtration of the reaction mixture using Amicon filters (MW cutoff 10,000; Millipore Co., Bedford, Mass.) without denaturation revealed that 77% of the compound $U_2$ (See FIG. 2B) was free in solution as compared to 35% of compound U. Adding sulfite to the reaction mixture eliminated compound U. completely and further stimulated the formation of compound $U_2$ (See FIG. 2C). Compound $U_2$ co-chromatographed in the HPLC system described above with [$^{35}$S] UDP-SQ indicating that the compound produced in the reaction mixture was UDP-SQ. (See FIG. 2D). Labeled compounds were detected using a β-Ram Model 2 Flow Through Monitor (INUS Systems, Tampa, Fla.).

Example 2 a. In this example, a means for the production of *Arabidopsis thaliana* recombinant SQD1 enzyme protein, as used in the method described in Example 1, and encoded by the nucleic acid sequence set forth in SEQ ID NO:5, is described. In order to isolate *A. thaliana* genes encoding enzymes involved in the head group biosynthesis of thylakoid membranes, the dbEST database of expressed sequence tags was searched with the predicted amino acid sequence of the bacterial sqdB genes using TBLASTN. Through said search, a partial rice cDNA (EST D46477) was found that encodes a putative protein with high sequence similarity to the bacterial sqdB gene products. A 400 base pair Xho I-EcoRV fragment of the partial rice cDNA was used as a probe to screen 2.4 million plaque-forming units (pfu) of an *A. thaliana* PRL2 cDNA library (a lambda ZipLox-based library available from the *Arabidopsis* Biological Resource Center at Ohio State University, Columbus, Ohio) by heterologous DNA hybridization. Hybond N+ (Amersham) membranes were used, and hybridization was performed at 53° C. in 0.25 M sodium phosphate buffer (pH 7.2) containing 7% (wt/vol) SDS, 1 mM EDTA, and 1% (wt/vol) BSA. After hybridization, the membrane was washed twice for 20 minutes in a 2× SSPE, 0.1% (wt/vol) SDS solution at 53° C.

Several cDNA clones were isolated, including one with an insert of 1,799 base-pairs, which was sequenced (GenBank accession No. AF022082). The open reading frame (ORF) beginning at nucleotide 170 encodes a putative protein with a calculated molecular mass of 53.1 kDa. An amino acid comparison analysis of the sqdB gene of *Synechococcus* sp. PCC7942 and the deduced amino acid sequence of the *A. thaliana* cDNA revealed a sequence identity of 42%. The corresponding locus of *A. thaliana* was designated SQD1 and the plasmid containing the cDNA with the 1,799 bp insert was designated pSQI1. At the amino acid level, the partial rice cDNA sequence was 86% identical to the SQD1 sequence of *A. thaliana*.

To produce recombinant SQD1 protein in *Escherichia coli*, a 1,199 base-pair fragment of pSQD1 (nucleotide numbers 425-1603 of GenBank accession no. AF022082) was cloned into the His-tag expression vector, pQE-30 (QIAGEN, Inc., Valencia, Calif.) using a PCR-based strategy. For this purpose, a forward primer having the nucleotide sequence 5'-AAA GGA TCC CGT GTT ATG GTC ATT GG-3' (SEQ ID NO:10), and a reverse primer having the nucleotide sequence 5'-GTC GGA TCC TTA TGT GGT CAT GGA CT-3' (SEQ ID NO:11) were used such that a BamHIH site was provided for cloning into pQE-30, and that the N-terminal 85 amino acids containing the presumed signal peptide were removed. The resulting plasmid construct, pSQD1-TP, allowed the expression of the recombinant SQD1 protein in *E. coli* and the purification of the protein due to the selective binding of the six N-terminal histidine residues of the plasmid construct to Ni-NTA agarose following the manufacturer's instructions. (QIAGEN, Inc., Valencia, Calif.).

Figure 8:
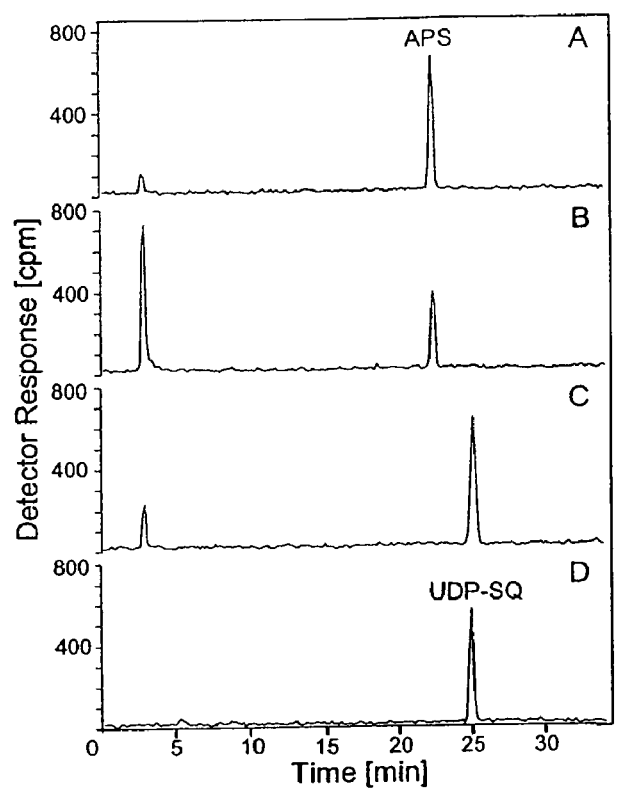
FIG. 8 is a chromatograph showing the results of a coupled APS reductase/SQD1 assay. HPLC chromatograms of reaction products and standards are shown. (A) $^{35}$S-labeled substrate APS without enzymes; (B) $^{35}$S-labeled reaction products following the incubation with APS reductase alone, or (C) in the presence of APS reductase and SQD1; (D) $^{14}$C-labeled UDP-SQ (U2) from the standard SQD1 assay.

The recombinant protein was eluted with 200 mM imidazole, which was subsequently removed by use of a Millipore Ultrafree 4 concentrator (Millipore, Inc., Bedford, Mass.). The protein was stored in 20% glycerol, 300 mM NaCl, and 25 mM $NaH_2PO_4$ (pH 7.5) at –20° C. The SQD1 protein was estimated to be approximately 95% pure by SDS-PAGE gel analysis (See FIG. 4).

b. An enzyme assay was developed to measure the conversion of UDP-glucose to UDP-SQ as predicted for SQD1 activity. Basic activity assays were carried out at 37° C. in a buffer containing 10 μg purified SQD1 protein, 100 μM $Na_2SO_3$, 500 μM UDP-glucose [$^{14}$C(U)-glucose](89 Bq/nmol) and 50 mM Tris (pH 7.5) in a total volume of 100 μl for 40 minutes. An further alternative assay, the coupled adenosine 5'-phosphosulfate (APS)(Sigma, St. Louis, Mo.)/SQD1 assay, contained 50 mM Tris (pH 8.5), 10 mM dithiothreitol (DTT), 25 μM [$^{35}$S]APS (500 Bq/nmol), 250 mM $Na_2SO_4$, 1 mM EDTA, 500 μM UDP-glucose, 66 μg purified SQD1 protein, and 12 μg APR1 from *A. thaliana*. (See FIG. 8). In both assays, the reaction was incubated at 30° C. for 10 minutes. The samples were heat denatured for 5 minutes at 95° C., centrifuged at 10,000×g for 5 minutes, and analyzed by HPLC (Waters Corp., Milford, Mass.) employing a Beckman (Fullerton, Calif.) Ultrasphere ODS column (4.6 mm×25 cm, particle size 5 μM) kept constantly at 42° C. Substrates and products were separated and analyzed by HPLC as described above in Example 1.

Example 3

In this example, a means for the simplified transformation of *Arabidopsis* is described herein and follows the methods of S. Clough and A. Bent, "Floral dip: a simplified method for *Agrobacterium*-mediated transformation of *Arabidopsis thaliana*," *Plant J*, 16:735-43 (1998).

a. In this example, a *Agrobacterium tumefaciens* strain carrying the gene of interest, SQD1, on a binary vector is prepared as follows. The entire SQD1 coding sequence (See SEQ ID NO: 6), including transit peptide, but excluding DNA 5 prime of gene, is cloned into pBluescript II (Stratagene, La Jolla, Calif.) using a PCR-based strategy. For this purpose, said SQD1 sequence was amplified by PCR using a forward primer having the nucleotide sequence 5'-CTA GGT ACC AAA TGG CGC ATC TAC TT-3' (SEQ ID NO: 20), and a reverse primer having the nucleotide sequence 5'-GTC GGA TCC TTA TGT GGT CAT GGA CT-3' (SEQ ID NO: 11). The primers were constructed such that Kpn I and BamHI sites were provided for cloning the SQD1 cDNA fragment into pBluescript II.

The SQD1 cDNA fragment is then excised from pBluescript II using the above restriction endonucleases, and subcloned into the corresponding restriction sites on the binary vector, pBINAR-Hyg. This vector is derived from pBIB-Hyg (Becker, D., *Nucleic Acids Res.* 18: 203 (1990)) by insertion of the Hind III-Eco RI fragment from the central portion of pA7 (von Schaeven, A., Ph.D. thesis, Freie Universität Berlin (1989)). This construct is introduced into Agrobactierium tumefaciens strain C58C1 and used to transform *Arabidopsis thaliana* Col-2 plants as described below.

b. *Arabidopsis* plants are grown under long days in pots in soil covered with bridal veil, window screen or cheesecloth, until they are flowering. First bolts are clipped to encourage proliferation of many secondary bolts, causing the plants to be ready roughly 4-6 days after clipping. Optimal plants have many immature flower clusters and not many fertilized siliques, although a range of plant stages can be successfully transformed.

The *Agrobacterium tumefaciens* strain carrying the gene of interest on a binary vector is grown in a large liquid culture at 28° C. in LB (10 g tryptone, 5 g yeast extract, and 5 g NaCl per liter of water) with 25 µg/ml hygromycin B (Calbiochem) to select for the binary plasmid. The *Agrobacterium* culture is pelleted by centrifugation at 5500×g for 20 minutes, and resuspended to $OD_{600}=0.8$ in a sterile 5% Sucrose solution.

Before the above-ground parts of an *Arabidopsis* plant are dipped in the resuspended *Agrobacterium*/Sucrose solution, Silwet L-77 (OSi Specialties, Inc., Danbury, Conn.) is added to a concentration of 0.05% (500 µl/L) and mixed well. The above-ground parts of an *Arabidopsis* plant are dipped in the *Agrobacterium* solution for 2 to 3 seconds, with gentle agitation. The dipped plants are placed under a dome or cover for 16 to 24 hours to maintain high humidity. The dipped plants are not exposed to excessive sunlight as the air under dome can get hot.

The plants are grown for a further 3-5 weeks and watered normally, tying up loose bolts with wax paper, tape, stakes, twist-ties, or other means. Watering is halted as the seeds of the plant become mature. Once mature, the dry seeds are harvested by the gentle pulling of grouped inflorescences (i.e. flower clusters) through fingers over a clean piece of paper. The majority of the stem and pod material is removed from the paper and the seeds are stored under dessication at 4° C.

Successful transformants capable of expressing a recombinant *A. thaliana* peptide are selected by using an antibiotic or herbicide selectable marker. In this example, 2000 harvested seeds (resuspended in 4 ml 0.1% agarose) are vapor-phase sterilized and plated on selection plates with 50 µg/ml hygromycin B, cold treated for 2 days, and then grown under continuous light (50-100 µEinsteins) for 7-10 days. The selection plates of the example are further comprised of 0.5×Murashige-Skoog medium (Sigma Chem. Cat.# M-5519) and 0.8% tissue culture Agar (Sigma Chem. Cat.# A-1296). Successful transformants are identified as hygromycin-resistant seedlings that produce green leaves and with well-established roots within the selective medium.

A sample of successful transformants are grown to maturity by transplantation into heavily moistened potting soil. Leaves from the transformants are removed and subjected to DNA extraction to isolate the genomic DNA of the plant. The extracted genomic DNA is subsequently subjected to restriction endonuclease digestion and Southern Blotting to confirm the incorporation of the gene of interest into the plant's genome.

Example 4

In this example, a means for the expression of a peptide, SQDX (SEQ ID NO: 1), as contemplated in the example above, is described. The entire insert of the plasmid pSYB carrying the sqdB gene of *Synechococcus* was sequenced (GenBank Accession No. AF155063) leading to the identification of a new ORF (open reading frame) directly 3' of sqdB. The plasmid pSYB is derived from the plasmid pBlueScript II-SK+ (Stratagene, LaJolla, Calif. Cat.# 212205) and contains the entire sequence of the sqdB gene cDNA (SEQ ID NO: 8) cloned into the plasmid's KpnI and BamHI sites. This ORF encodes a putative protein of 377 amino acids with no sequence similarity to any of the described sqd gene products of *R. sphaeroides*. Unlike the preceeding sqdB ORF which starts with GTG, the second ORF begins with ATG 15 bp from the 3' end of the sqdB gene. This ORF was designated sqdX. Analysis of the deduced amino acid sequence of sqdX (FIG. 17: SEQ ID NO: 2) employing Pfam (Protein families database of alignments) revealed a glycosyltransferase group I domain between the residues 228 and 347.

To confirm that the sqdX gene in the cyanobacteria *Synechococcus* encodes functionally homologous proteins, the sqdX open reading frame of *Synechococcus* was inserted behind the tac promoter in the mobilizable broad host range plasmid pRL59EH (Black et al., "Analysis of a Het-mutation in *Anabaena* sp. PCC7120 implicates a secondary metabolite in the regulation of heterocyst spacing," *J. Bacteriol.*, 174: 2282-2292 (1994)), and transferred the constructs by conjugation into *Synechococcus* mutant 7942ΔsqdX as described in Wolk et al., "Construction of shuttle vectors capable of conjugative transfer from *Escherichia coli* to nitrogen-fixing filamentous cyanobacteria," *Proc. Natl. Acad. Sci. USA*, 81: 1561-565 (1984). Sequences 5' of the presumed ATG up to the first in-frame stop codon (position 2385912-2387168 of the genome sequence) were included. The sqdX gene of *Synechococcus* was PCR-cloned from the plasmid pSYB using the primers 5'-AAG GAT CCT GCG CTA AAG TCG CAC TC-3' (SEQ ID NO: 21) and 5'-ATA AGC TTC GAG CTC AGG CCG CT-3' (SEQ ID NO: 13) into the Hind III/BamH I sites of pRL59EH. An Ω cassette from the plasmid pHP45Ω (as described in Prentki, P. and Krisch, H. M., "In vitro insertional mutagenesis with a selectable DNA fragment," *Gene*, 29: 303-313 (1984)) conferring spectinomycin and streptomycin resistance was inserted into the Hind III sites of these plasmids to provide a suitable selectable marker. The resulting plasmid containing sqdX of *Synechococcus* was designated pSQDX7942. Exconjugants were selected on BG11 medium containing 25 µg/ml kanamycin, 10 µg/ml spectinomycin, and 1 µg/ml streptomycin and were analyzed by DNA/DNA hybridization to confirm the presence of the proper plasmid construct. The insertion of the sqdx construct restored the sulfolipid biosynthetic activity in the *Synechococcus* mutant 7942ΔsqdX as shown by TLC lipid analysis. Based on the observed genetic complementation, it is concluded that the cyanobacterial sqdx gene encodes a protein involved in sulfolipid biosynthesis.

Example 5

In this example, a means for the production of sqdX gene homologs of *Arabidopsis thaliana* comprising the group consisting of the gene product ATSQDX-1 encoded by the nucleic acid sequence set forth in SEQ ID NO: 3, the gene product ATSQDX-2 encoded by the nucleic acid sequence set forth in SEQ ID NO: 4, or the gene product ATSQDX-3 encoded by the nucleic acid sequence set forth in SEQ ID NO: 5, is described. A BLAST comparison of the cyanobacterial sqdX gene to genomic sequence of *Arabidopsis thaliana* revealed several potential homologs. In one example, AtSQDX-1, a homolog having 37% amino acid identity with the cyanobacterial sqdX gene is contemplated. In another example, AtSQDX-2, a homolog having 29% amino acid identity with the cyanobacterial sqdX gene is contemplated. In a further example, AtSQDX-3, a homolog having 32% amino acid identity with the cyanobacterial sqdX gene is contemplated.

Example 6

In this example, a means for the subsequent modification of UDP-SQ to produce an alkyl sulfoquinovoside is described. The synthesis of alkyl sulfoquinovosides starts from the hydrolytic cleavage of the UDP-SQ. Sulfoquinovose is then refluxed with the acidic catalyst, para toluenesulfonic acid, in the presence of the short chain alcohol, butanol, to form a short chain butyl sulfoquinovoside. The reflux temperature is 118° C. With the formation of the lower boiling butanol/water mixture, a vapor temperature of 95 to 110° C. is established. The acetalization with the butanol is carried out under light vacuum, i.e. under a pressure of 800 to 950 mbar. An azeotropic amount of butanol is removed with the water in the distillation process.

The butyl sulfoquinovoside is subsequently treated under vacuum with the long-chain alcohol, n-hexadecyl alcohol, in the presence of the acidic catalyst to form a long-chain sulfoquinovoside. In order to obtain a low content of butyl sulfoquinovoside, removal of the butanol by distillation under reduced pressure of down to 10 mbar and neutralization of the catalyst are preferably separated by an interim period of up to about 1 hour, under which the reaction mixture is stirred under normal pressure at temperatures of from 100 C to 115° C.

In the next step the reaction mixture is cooled to a temperature below 95° C. The acidic catalyst is neutralized by the addition of the base, NaOH, and then adjusting the pH of the neutralized reaction mixture to a pH of 8.5. After filtering the reaction mixture at a temperature of from 80 to 90° C., the excess fatty alcohol is removed by distillation at to a level below 5% by weight. In using such techniques the so-called sump temperature must be kept at levels at which the alkyl sulfoquinovoside is thermally stable (i.e., the sump temperature should not exceed a value of 160° C.). The product obtained has a high content of the long-chain alkyl sulfoquinovoside and low content of the butyl sulfoquinovoside, alkyl monosulfoquinovosides, and also alkyl poly (oligo) sulfoquinovosides.

Example 7

AtSQDX Homolog Cloning and Sequencing

Although an understanding of the mechanism is not necessary to use the present invention, this example describes experiments designed to isolate the AtSQDX homologs and determine the amino acid and nucleotide sequences. The known genomic sequence containing the AtSQDX gene is used to generate oligonucleotide probes for the cloning of the gene encoding AtSQDX (Sambrook, et al., *Molecular Cloning: A Laboratory Manual*, 2nd ed., Cold Spring Harbor Laboratory Press, New York, pp. 16.7-16.8 (1989)). The sequence is isolated and amplified by PCR (see, e.g., Dieffenbach and Dveksler, *PCR Primer, a Laboratory Manual*, Cold Spring Harbor Press, Plainview, N.Y. (1995) and, U.S. Pat. Nos. 4,683,195, 4,683,202, and 4,965,188, which are herein incorporated by reference). After purification, the isolated sequence is cloned into an expression vector for transfection into a cell free, prokaryotic or eukaryotic expression system (See, Ausubel, et al., ed., *Short Protocols in Molecular Biology*, John Wiley & Sons, NY (1992)). After expression, the protein is isolated and purified. The protein may then be used for the generation of antibodies (see, generally, Howard and Bethell, e.g., *Basic Methods in Antibody Production and Characterization*, CRC Press, (2000)).

Alternatively, preparative reagents are generated to isolate the specific target by conjugating antibodies generated from expression of fragments of the genomic sequences known to contain the desired sequence. The antibodies are generated by methods known to those in the art (See, generally, Howard and Bethell, e.g., *Basic Methods in Antibody Production and Characterization*, CRC Press, (2000)) to generate anti-AtSQDX antibodies. The antibodies are conjugated to agarose beads. Furthermore, a parallel conjugate of agarose beads to a control immune globulin is accomplished. Ultracentrifuged cell lysates from the desired cell line are exposed to the control non-immune I conjugated beads to remove non-specifically binding proteins. The unbound lysate is recovered and is then exposed to the anti-AtSQDX antibody conjugated agarose beads for a direct affinity purification. The anti-AtSQDX antibody/AtSQDX complex is washed with 2.5 M KCL to remove non-specifically bound materials and the AtSQDX is then eluted from the agarose beads with 0.1 M glycine HCL in the presence of 0.5 M NaCl. The eluted material from the column is neutralized with 1 M Tris pH 8.0, dialyzed extensively to reduce the salt concentration to 150 mM and then reconcentrated. The reconcentrated material is placed on SDS-PAGE under non-reducing conditions for a final purification based on molecular size. This material is transferred to a membrane for electrospray tandem mass spectroscopic analysis of the amino acid sequence. This later sequence is used to generate oligonucleotide probes for the cloning of the gene encoding AtSQDX.

All publications and patents mentioned in the above specification are herein incorporated by reference. Various modifications and variations of the described method and system of invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

We claim:

1. A method, comprising:
   a) providing:
      i) uridine-5'-diphosphoglucose;
      ii) sulfite;
      iii) an isolated first polypeptide encoded by the nucleic acid sequence of SEQ ID NO: 6; and
      iv) an isolated second polypeptide encoded by a nucleic acid sequence selected from the group consisting of SEQ ID NO:1 and the cDNA of SEQ ID NO:3;
   b) reacting said uridine-5'-diphosphoglucose with said first polypeptide and said sulfite under such conditions that uridine-5'-diphosphosulfoquinovose is generated; and
   c) treating said uridine-5'-diphosphosulfoquinovose with said second polypeptide under conditions such that sulfoquinovose diacylglycerol is generated.

2. A method, comprising:
   a) providing:
      i) uridine-5'-diphosphosulfoquinovose;
      ii) diacylglycerol;
      iii) a nucleic acid sequence selected from the group consisting of SEQ ID NO: 1 and the cDNA of the sequence SEQ ID NO:3; and
      iv) a host cell
   b) transfecting said host cell with said nucleic acid sequence under conditions such that a polypeptide encoded by said nucleic acid sequence is expressed;
   c) isolating said expressed polypeptide; and
   d) reacting uridine-5'-diphosphosulfoquinovose with said polypeptide of step (c) and said diacylglycerol under conditions such that sulfoquinovosyl diacylglycerol produced.

3. A method, comprising:
a) providing:
i) a first vector comprising the nucleic acid sequence of SEQ ID NO: 6;
ii) a second vector comprising the nucleic acid sequence of SEQ ID NO: 1; and
iii) a host cell;
b) transfecting said host cell with first and second vectors, thereby creating a transformed host cell and culturing said host cell, under conditions such that sulfoquinovosyl diacylglycerol is produced by said transformed host cell.

4. The method of claim 3, wherein said host cell, prior to said transfecting of step (b) does not produce sulfoquinovosyl diacylglycerol.

5. The method of claim 4, wherein said host cell is a bacterial host cell.

6. The method of claim 5, wherein said bacterial host cell is *E. coli*.

7. The method of claim 3, wherein said first and second vectors are plasmids conferring different antibiotic resistance to said transformed host cell.

8. The method of claim 3, wherein said host cell, prior to said transfecting of step (b) produces less sulfoquinovosyl diacylglycerol than said transformed host cell.

9. The method of claim 8, wherein said host cell is a plant host cell.

10. The method of claim 9, wherein said plant host cell is derived from a monocotyledonous plant.

11. The method of claim 9, wherein said plant host cell is derived from a dicotyledonous plant.

12. A method, comprising:
a) providing:
i) a first vector comprising the nucleic acid sequence of SEQ ID NO: 6;
ii) a second vector comprising the nucleic acid sequence corresponding to the cDNA of the sequence of SEQ ID NO: 3; and
iii) a host cell;
b) transfecting said host cell with first and second vectors, thereby creating a transformed host cell and culturing said host cell, under conditions such that sulfoquinovosyl diacylglycerol is produced by said transformed host cell.

13. The method of claim 12, wherein said host cell, prior to said transfecting of step (b) does not produce sulfoquinovosyl diacylglycerol.

14. The method of claim 13, wherein said host cell is a bacterial host cell.

15. The method of claim 14, wherein said bacterial host cell is *E. coli*.

16. The method of claim 12, wherein said first and second vectors are plasmids conferring different antibiotic resistance to said transformed host cell.

17. The method of claim 12, wherein said host cell, prior to said transfecting of step (b) produces less sulfoquinovosyl diacylglycerol than said transformed host cell.

18. The method of claim 17, wherein said host cell is a plant host cell.

19. The method of claim 18, wherein said plant host cell is derived from a monocotyledonous plant.

20. The method of claim 18, wherein said plant host cell is derived from a dicotyledonous plant.

21. The method of claim 1, further comprising the step of isolating said sulfoquinovose diacylglycerol generated in step (c).

22. The method of claim 2, further comprising the step of isolating said sulfoquinovosyl diacylglycerol produced in step (d).

23. The method of claim 3, further comprising the step of isolating said sulfoquinovosyl diacylglycerol produced in step (b).

24. The method of claim 12, further comprising the step of isolating said sulfoquinovosyl diacylglycerol produced in step (b).

* * * * *

SEQUENCE LISTING

<160> NUMBER OF SEQ ID NOS: 24

<210> SEQ ID NO 1
<211> LENGTH: 1134
<212> TYPE: DNA
<213> ORGANISM: Cyanobacterium Synechococcus
<220> FEATURE:
<221> NAME/KEY: CDS
<222> LOCATION: (1)..(1134)

<400> SEQUENCE: 1

```
atg cgc atc gct ctc ttt acc gag acg ttc ctc ccc aaa gtg gat ggc      48
Met Arg Ile Ala Leu Phe Thr Glu Thr Phe Leu Pro Lys Val Asp Gly
 1               5                  10                  15 atc gtc acg cgg ctt cgg cac acg gtc gat cac ctg cag cgt ctt ggc      96
Ile Val Thr Arg Leu Arg His Thr Val Asp His Leu Gln Arg Leu Gly
             20                  25                  30 cac acc gtc atg gtt ttt tgc ccc gac ggc ggg ctc cgc gag cac aag     144
His Thr Val Met Val Phe Cys Pro Asp Gly Gly Leu Arg Glu His Lys
         35                  40                  45 ggg gct cga gtc tat ggg gtt aaa ggc ttt ccg cta ccg ctc tat ccc     192
Gly Ala Arg Val Tyr Gly Val Lys Gly Phe Pro Leu Pro Leu Tyr Pro
     50                  55                  60 gag ctg aag cta gct ttt ccg ttg ccg aaa gtg gga aaa gcc ttg gag     240
Glu Leu Lys Leu Ala Phe Pro Leu Pro Lys Val Gly Lys Ala Leu Glu
 65                  70                  75                  80 cgg ttc cgg ccc gac ctg atc cac gtg gtc aat ccg gct gtg ttg ggg     288
Arg Phe Arg Pro Asp Leu Ile His Val Val Asn Pro Ala Val Leu Gly
                 85                  90                  95 ttg ggc ggc atc tac tat gcc aag gcg cta aat gtg cca ctc gtg gcg     336
Leu Gly Gly Ile Tyr Tyr Ala Lys Ala Leu Asn Val Pro Leu Val Ala
            100                 105                 110 tcc tat cac acc cat ttg ccg aaa tac ctt gag cat tac ggg ctg ggg     384
Ser Tyr His Thr His Leu Pro Lys Tyr Leu Glu His Tyr Gly Leu Gly
        115                 120                 125 gtc ttg gag ggg gtg ctc tgg gaa ttg ctg aag ctg gcg cat aac caa     432
Val Leu Glu Gly Val Leu Trp Glu Leu Leu Lys Leu Ala His Asn Gln
    130                 135                 140 gca gcg atc aac ctc tgt act tca acc gcg atg gtg cag gag ctg aca     480
Ala Ala Ile Asn Leu Cys Thr Ser Thr Ala Met Val Gln Glu Leu Thr
145                 150                 155                 160 gat cac ggc att gag cac tgt tgc ctc tgg cag cga gga gtg gat acc     528
Asp His Gly Ile Glu His Cys Cys Leu Trp Gln Arg Gly Val Asp Thr
                165                 170                 175 gag acc ttt cgg cca gac ttg gct act gct gcg atg cgc gat cgc ctc     576
Glu Thr Phe Arg Pro Asp Leu Ala Thr Ala Ala Met Arg Asp Arg Leu
            180                 185                 190 agt ggc ggt aag ccc act gcg ccc ttg ttg ctc tac gtc gga cgc ctc     624
Ser Gly Gly Lys Pro Thr Ala Pro Leu Leu Leu Tyr Val Gly Arg Leu
        195                 200                 205 tca gcc gag aag caa atc gat cgc ctg cga ccc att ttg gat gcc aat     672
Ser Ala Glu Lys Gln Ile Asp Arg Leu Arg Pro Ile Leu Asp Ala Asn
    210                 215                 220 cct gag gct tgc ttg gcc ttg gtc ggc gat ggc ccg cat cgg gcc gaa     720
Pro Glu Ala Cys Leu Ala Leu Val Gly Asp Gly Pro His Arg Ala Glu
225                 230                 235                 240 cta gag caa ttg ttt gct ggc acc cag acg cag ttc att ggc tat ctg     768
Leu Glu Gln Leu Phe Ala Gly Thr Gln Thr Gln Phe Ile Gly Tyr Leu
                245                 250                 255
```

```
cat ggg gaa cag cta ggg gcg gcc tac gct tct gct gac gct ttt gtc    816
His Gly Glu Gln Leu Gly Ala Ala Tyr Ala Ser Ala Asp Ala Phe Val
        260                 265                 270 ttt ccc tcc cgg acc gaa acc ctc ggt cta gtc ttg ctg gaa gcc atg    864
Phe Pro Ser Arg Thr Glu Thr Leu Gly Leu Val Leu Leu Glu Ala Met
275                 280                 285 gca gcg ggt tgt ccg gtc gtg gcg gcc aat tcc ggt ggc att ccc gat    912
Ala Ala Gly Cys Pro Val Val Ala Ala Asn Ser Gly Gly Ile Pro Asp
        290                 295                 300 att gtc agc gac ggc att aat ggt ttc ctg ttc gat cct gag gat gaa    960
Ile Val Ser Asp Gly Ile Asn Gly Phe Leu Phe Asp Pro Glu Asp Glu
305                 310                 315                 320 caa ggg gcg atc gct gcg att cag cgc ttg ttg gct aac cct gca gag   1008
Gln Gly Ala Ile Ala Ala Ile Gln Arg Leu Leu Ala Asn Pro Ala Glu
                325                 330                 335 cgc gag att cta cgc caa gcg gct cgt caa gaa gcc gaa cgc tgg agc   1056
Arg Glu Ile Leu Arg Gln Ala Ala Arg Gln Glu Ala Glu Arg Trp Ser
            340                 345                 350 tgg aac gca gcc acg cgc caa ctc cag gac tac tac tgc gag gtg ttg   1104
Trp Asn Ala Ala Thr Arg Gln Leu Gln Asp Tyr Tyr Cys Glu Val Leu
        355                 360                 365 gca gat ggt tgc tta ccc tta gcg gcc tga                            1134
Ala Asp Gly Cys Leu Pro Leu Ala Ala
370                 375

<210> SEQ ID NO 2
<211> LENGTH: 377
<212> TYPE: PRT
<213> ORGANISM: Cyanobacterium Synechococcus

<400> SEQUENCE: 2

Met Arg Ile Ala Leu Phe Thr Glu Thr Phe Leu Pro Lys Val Asp Gly
1               5                   10                  15

Ile Val Thr Arg Leu Arg His Thr Val Asp His Leu Gln Arg Leu Gly
            20                  25                  30

His Thr Val Met Val Phe Cys Pro Asp Gly Gly Leu Arg Glu His Lys
        35                  40                  45

Gly Ala Arg Val Tyr Gly Val Lys Gly Phe Pro Leu Pro Leu Tyr Pro
    50                  55                  60

Glu Leu Lys Leu Ala Phe Pro Leu Pro Lys Val Gly Lys Ala Leu Glu
65                  70                  75                  80

Arg Phe Arg Pro Asp Leu Ile His Val Val Asn Pro Ala Val Leu Gly
                85                  90                  95

Leu Gly Gly Ile Tyr Tyr Ala Lys Ala Leu Asn Val Pro Leu Val Ala
            100                 105                 110

Ser Tyr His Thr His Leu Pro Lys Tyr Leu Glu His Tyr Gly Leu Gly
        115                 120                 125

Val Leu Glu Gly Val Leu Trp Glu Leu Leu Lys Leu Ala His Asn Gln
    130                 135                 140

Ala Ala Ile Asn Leu Cys Thr Ser Thr Ala Met Val Gln Glu Leu Thr
145                 150                 155                 160

Asp His Gly Ile Glu His Cys Cys Leu Trp Gln Arg Gly Val Asp Thr
                165                 170                 175

Glu Thr Phe Arg Pro Asp Leu Ala Thr Ala Ala Met Arg Asp Arg Leu
            180                 185                 190

Ser Gly Gly Lys Pro Thr Ala Pro Leu Leu Leu Tyr Val Gly Arg Leu
        195                 200                 205
```

-continued

| | | | | | | | | | | | | |
|---|---|---|---|---|---|---|---|---|---|---|---|---|
|Ser|Ala|Glu|Lys|Gln|Ile|Asp|Arg|Leu|Arg|Pro|Ile|Leu|Asp|Ala|Asn|
| |210| | | |215| | | |220| | | | | | |

Pro Glu Ala Cys Leu Ala Leu Val Gly Asp Gly Pro His Arg Ala Glu
225              230                    235                    240

Leu Glu Gln Leu Phe Ala Gly Thr Gln Thr Gln Phe Ile Gly Tyr Leu
                245                    250                    255

His Gly Glu Gln Leu Gly Ala Ala Tyr Ala Ser Ala Asp Ala Phe Val
            260                    265                    270

Phe Pro Ser Arg Thr Glu Thr Leu Gly Leu Val Leu Leu Glu Ala Met
        275                    280                    285

Ala Ala Gly Cys Pro Val Val Ala Ala Asn Ser Gly Gly Ile Pro Asp
    290                    295                    300

Ile Val Ser Asp Gly Ile Asn Gly Phe Leu Phe Asp Pro Glu Asp Glu
305                    310                    315                    320

Gln Gly Ala Ile Ala Ala Ile Gln Arg Leu Leu Ala Asn Pro Ala Glu
                325                    330                    335

Arg Glu Ile Leu Arg Gln Ala Ala Arg Gln Glu Ala Glu Arg Trp Ser
            340                    345                    350

Trp Asn Ala Ala Thr Arg Gln Leu Gln Asp Tyr Tyr Cys Glu Val Leu
        355                    360                    365

Ala Asp Gly Cys Leu Pro Leu Ala Ala
370                    375

<210> SEQ ID NO 3
<211> LENGTH: 2979
<212> TYPE: DNA
<213> ORGANISM: Cyanobacterium Synechococcus

<400> SEQUENCE: 3

```
ctacacgtta ccttccggta ctggaaacag tcgtttaatc aaccaattga ttggtcccaa    60
aacatgaact ttctttttcc tccagaacca atcgctgca ctgtactgtt cattgcgtat    120
ctttgtcgtt gctgctctcc aatcatattt ctcggtctct tctcttgccg cttttccaat   180
gatctctctt gtttcacggt cgtgcagtaa agttctcagt tttgtcacgc aatcttcaac   240
atctccaggg ttgaacaaaa atccggtttt tccctcctga tgaaaacatc agaatcagaa   300
aaccacaagc tcaatatagg ttgacccata agaacaatca atgcaagatc attttgtgta   360
ccagtctatg attgaataaa gtttcagttc ggttacagct cgcttataag aaaattggca   420
gaaattgttt tttcaaccat ttcggttcgg ttgatatgct catcaatatg gtttggcagt   480
taattgtaat tcagataatt cactgacctg atcttcaggg attatatcag ggattccacc   540
ggcacgggcc gcgacgacag gaagtcctga agacattgct tcaagaacca caaggccaag   600
tgtctccgac tctgatggca tcacaaacac atctccactt gcgtaagctt gtgagagttc   660
atcgccttgt aacgttccag tgaaaaccgc tggcattccg gtaaacaact tctcaagatc   720
ctctctttaa gaaaacgaaa cagataaaca aaattacaat gttgttgact agaaatcttc   780
agataacaat atggccaatc tttaacaaaa ctagtacttg tatggtccat ctccaatgaa   840
agcaatccga gcttcaggta atttgtccat tacactgcac acaaatttct caatatcaaa   900
attcgataca ccacttaaaa gaagtgagtc cagtttatac aaaattctaa cctctttaaa   960
agctccaaac tctttttctac gccaatgcga cctacatgaa tcactagtgg cttttctggt  1020
tcgccattac tgttaattac aaaatattaa acatcaagat tagcgtggaa agtatcattg  1080
tttttaatgc atataaaaga aacgtatatt ctattcttgc ctcagtctta tacgcatttc  1140
```

```
ttgagaacgg aaacggggat tgaagctttc tgaatcgaca cccttattcc aaagtcgaag   1200
ttgattagct tcaatatatg aaaaaaagaa gaagaaaatg taagttttga acaatcatag   1260
agcttgtaca aaaatgtaat gtatgatctt tcttcacctg cagttgcacc agctgctata   1320
agatcttttc caatggcagc agaaggaact aatgtaagat cagccgctct gtgaaggaac   1380
cctgataaaa gcatattcaa gtttagtttc atattataca tcacaataaa ccagaaaaag   1440
aagaaggaaa ttttgacatt tgaaaagcgg gttttacata cttattatag accacattgg   1500
ttttaccaac caactaaaag tgtatcttgg gatgtatctg cacatcaaca caagcttaat   1560
cttagacaaa aattttttta taacaacatt gtgaaatgag gcagaaaaag gtacttacac   1620
agggacgtgt gtgtggtaag acattactat tggtacagat agcattttg ctattgccag    1680 agcaccaaag acctaaaaat tttagtcagg gaaaaaagag agtcaagttc tggattctct   1740
ccagttcact ggtcttgcta atgttttagt aatgtgaatt cttgagggat ttaccataac   1800
tccgggagat gaagcgtgta taatgtcagg cttaaaccgt gcaatttcag agatgattct   1860
tggactaagc gcaagcgaga gtggaacctt ttggtaataa ggacaaggga agctacagaa   1920
gagaagaaga aattagcgat attaccaaat agagaacatc cagtgagtaa actaaatggt   1980
gctaccttct tgatccaatg actctggctc cataaaactc ttcaggaaca ccttcatgtg   2040
tcgtcacgac tataacctat gaagcaaaaa agttattaaa aaaaaaaaaa aaggaacagt   2100
taacacttgt caagtaattc taattctgga aacagttact tatgagctga ctgaaaagat   2160
acttaagttg aagaatgaga tagtaaaaga agaaacctcg tctcccattt cacggaggta   2220
tctaatgaaa ttctggaatc tgttttttgta gccggataca tagctgcaac aaaatcaaag   2280
agagaatcac ttccaataat aacatgacat ataataaaag cttttggtca atggatcggt   2340
gattccgaga atcttgggat attcacaact aaaatctgac aactttgact caaacaaatc   2400
ctgaatgtaa ttggttttaa cgatctacta tataatttgc taaattggtg gtgtagcaaa   2460
ttcatacatt agcgagtatc tcttcataaa ataaatgtaa cgatcaaatc gaaagaaaaa   2520
aacattacag gaaaaagtca accaaggaaa aaatgagta gaatctgttt tcacagagac    2580
atttcgtcga acacaaaaca agcaaaaaaa gaacactgtg aagaagactt acgcaaaggg   2640
agaaggctca acaaagagag caattctcct aggcttagag agcgactcag gatcgagaag   2700
cggcgcatca atctccgatt cgtcatcttc tctgacttga gtaatagtca tatcgttgga   2760
cccagaaaca gcttcctttg taatcactcc acagaagcgg agcttgcttt tcttgctaat   2820
gggtaatctc cggtgaccaa acgaaagagg ggaatgaaga acaaaagaag aagacctggg   2880
aggagaacaa gaggttgcag aggaagaaga acaagtgtta gtcgtgctag gaagcaaatg   2940
aggaggtata gagagattta tagaagaaag agtcgtcat                          2979
```

<210> SEQ ID NO 4
<211> LENGTH: 2537
<212> TYPE: DNA
<213> ORGANISM: Arabidopsis thaliana

<400> SEQUENCE: 4

```
tcatattttg aaaaagcact tcttcttctt cttcttcttc ttcttcttct tcttcttccc     60
atcaaaaagt gctagtggca agaccgcgca tattccagta acaaagttta aattcaaaac   120
tatggaacac aatttgtccc atgttttgtt gcctgaatta aacgaccata tcacttggtt   180
cggccacttc atctcggata cgcacaagcg gttgtcaagg ttgtaaaaga cgattttgta   240
aggatctaca ttggcaaagg gagctttaca gacgacttga aaagtttcgg tgtgaagatt   300
```

```
gaaaggtaaa actttggttt ctttgcactc ggtgaaccaa taaagcgacc catctagata      360
cacaggtgcg gggtaagcag caatccgata aggagcagcg agagtgacat acctccaagc      420
attggtacta aagtcgaaaa cttcgcatgt agtagcgttt tttaggccta tttctgcaga      480
gttgtataac caaacgggct tgtatgtgcc cctgaatttg tctttaccga atccaagcat      540
aaagaatttg cgtttaagct tgtagtaacc atctcgtaag tcgatcatga gtttttgata      600
atcgcaaaga ggaagaggcc gataccatct agtggtcggg ttgaccacat aaccggattt      660
gtcgtgattg taaagacaaa cgagaccgtc acaactacta tgtgaaacta agtacagtac      720
gttatccttc tcccaaggag tagggatctt gaacgttgat gatgaaccca actgcaatgt      780
tcttaaagat tctatggtcg ggtttataac atggtgagga aatacagaca ccatcagaac      840
atctggatct cctgattgct gacgatgttt caactaaaat tgtatacatt tttattttat      900 taaaagata aatatcattt tgttggaatt ggaaaacaaa atctaaaaga taactttaga      960
tatgtaaggg tcgcatatgt atttgattac attgctatga gtatatgact cacttttcca     1020
ataatgaaaa aaataaagat gttgagtctt actaattaag ggtaaataca aaatttctga     1080
tcattaatac aaagaaaaag cctctcataa gccaaagcca tttactcgc cgtaaacatc      1140 tccgcagcat actctttaca cttccttcct ctctccgcca atctctccgc tccttcagcc     1200
acagcaacct ccataaccgc cgtcaaagct tccacatttg gcgcaaacat aaacccaaac     1260
tcatcattca ccactatagt cctctttatg cttgcgtacc tagatgccat cactggttta     1320
ccactcaaca tcgcttccat taacgttaaa tcaagacctt gtggtctaag cgttggattc     1380
acgaacaaat cgatcccgtt gtagaaaccc ttgagctcat ttgggtttag agatcccaaa     1440
atggaaactt tttcccctaa ttccttgtaa cgttgctccc atggccctga tccagctact     1500
acgaggtaaa catttgaata cgtttggatt attttcgcga aagcttcgaa gagcaatgga     1560
tgtcctttgt ctttgactaa tctcccagca gctcctaaaa caatcgctga tgagttttct     1620 ggtaaccta attttgacct aaacagagta cgtagcttct tgtctgatgt gaatccgttc      1680
tcgtcgactc cattgaggat cacatgaacc cttttctcag ggatttggta aacgtctctt     1740
agcatttctc cgcagctatc gctgatagcg atgtggtgag cgtagttgtg aagaatctg      1800 atttcgtcca gtatcttggg aagcacggca ccgtatagac ttgcattgaa gccttgtgat     1860
cttggttcgt ctggtttacg gatcaggtct tggtaaatac ttgattgtaa gctctctaac     1920
gcaatgccgt gccaggatac agcgaggttt ggaacctccc gggcgatcca gtgaggtaaa     1980 gcaacactt cagagtgaac cgcatcgaaa ggttctttct tgttttcttc ttggtaaagc      2040
tcccatgcct tgttgtaccg ccatttccg ggctccgcgt cgccgtgaga atggattata      2100
gggtaaatga tttggtcgga aacaggggg attttgttgg tttcagggga ttggtctaag     2160
ggagaggtga aaacgtggac acggtgtcca cggcgagcta aggcggtgta tagagtgaag     2220
gcgtggcgtt ccatgccgcc aggattggga cccgtgggcc atttccggga gaaaacagcg     2280
agttttagtg ttttgggagg agggttggtt aaggagaaat caaggcggtt ccaggcaaat     2340
tgggcggttt ggaggtcgcc agaccacggt ggctggtttg tgtcagagga ggaggaggag     2400
actgcagcgg tggaggagga gcaagtggag gtgcggagga gaaagagagc cggtatggta     2460
aagaggacgg tgaagaagag gaaagtacaa aggctaaaat gagaattagg tttcttgagt     2520
ttggtttgtg aagccat                                                   2537
```

-continued

<210> SEQ ID NO 5
<211> LENGTH: 2369
<212> TYPE: DNA
<213> ORGANISM: Arabidopsis thaliana

<400> SEQUENCE: 5

| | | | | | | |
|---|---|---|---|---|---|---|
| ttaaggtctc | atgcatttga | ccagaacatc | gacgaatcgc | ttgtacatat | gttgcttcat | 60 |
| gtacattttc | tcaaccattt | tgcgtccttc | actccccaat | cgtagcctct | cgtctggatt | 120 |
| cctaagtaga | tacaagagat | tatgagctaa | ttctttgtta | ccggatctcc | ccattgagtg | 180 |
| aagtagacca | gtcatgttgt | gttgaaccat | ctctttggtt | cctcctgcat | ctgttcccac | 240 |
| cactgcaagt | ccataagcca | ttgcttcgat | tgtcactcta | ccaaatgttt | caccaactcc | 300 |
| ctgtaaaaaa | tcaaggttca | aaataaataa | accgaacaaa | atcgaaatgg | tcaaaccgaa | 360 |
| atcaaaacct | acattttgaa | caaaaacaaa | actgaaatgt | tttatccaaa | accaaactga | 420 |
| aatcaatcac | aaattggttt | atttgattca | gtaattcaag | ttcctataaa | actgataaaa | 480 |
| ctaaaccaaa | acctaactgt | aaactacttt | ctagtggaaa | actgcatatg | catcaaataa | 540 |
| tgttttttgag | gtgtgaggag | gattacctgg | gagtttgtaa | cgtagacatc | tgctgcagag | 600 |
| tataatgaag | caacacgggt | tgttgcagga | gtccacatta | ccgacttaga | taagtttccg | 660 |
| ctgtttgaca | agaagcttaa | catctcttta | acgtatccaa | ctttgttgct | ctttgaaccc | 720 |
| acggatccta | aaagaacttt | aagttcttgc | ttctctcttc | ttaagccatt | gtcaagtgtg | 780 |
| agagaaacac | ttttcatctg | tcgtgatgaa | cctcttaaac | gatgtttgct | ggagagacta | 840 |
| acctttctt | tcctaatgat | ccccttgtga | ttcctttgag | attcttgtcc | tctctcagaa | 900 |
| agagccaagg | caatagattc | aaggagaaga | agttgtccct | tgttgggtt | tatgctgcta | 960 |
| agagacatca | caagcatatc | tgaatctgtt | attcctaact | ctgttctcac | tgattcgcgt | 1020 |
| aatatttgtc | tcttcaccct | cattttctct | ggtgaaagtg | ttggtgtgtt | gagtgaagaa | 1080 |
| ggaatccccg | ctacaaaagc | taactcatca | ttaacagata | gtggaacaat | cactggttgt | 1140 |
| gatctaagct | ttatatgctc | ctcctcgcac | catgttaacc | attgtctgct | ctgtgattca | 1200 |
| gataagaaaa | tcagcatttt | cactcggtca | gaactggtt | tcgctcgatc | aaagtattct | 1260 |
| cgtcgattct | ccattatcca | ccaagctatt | tgacttccac | cagctggatg | atgattcatg | 1320 |
| tattgatctg | cgagaaaagg | aaaaaaaaaa | agtaattaag | atatgctttc | ctctgattgt | 1380 |
| aaattagtag | tctaaaaact | gcataatgaa | ttcttaccta | tccatgaggt | acacactgct | 1440 |
| gatcctgcga | tgatcaaatc | tgctttcatg | gcagtcttga | agctgagttc | tcctttgtct | 1500 |
| tcaacaactt | tgatccttct | cctactgagc | tcttgcatca | atccacctct | cctgctaaga | 1560 |
| actactgcag | agactgttgc | accacagctc | aaaagctctg | aagccagctc | catcatagaa | 1620 |
| attggagcac | cagtcattga | tagctcgtgg | aaaagcagga | cgaatctcct | tgaccaaaca | 1680 |
| aggcgtttaa | aatctgattt | cctgtcgcaa | gtcccagatc | ttctatgcgg | gctccattca | 1740 |
| agaactttat | cctctagtga | tccaaaggga | ccaagaagct | taccataagt | agcatttgtc | 1800 |
| aatggaagtt | gtggatcttg | ctcatcatcc | aaatccttag | tctcaagtac | ctcttttaatc | 1860 |
| accttctgct | taacacggat | cttactacga | gaagtccgga | cagttttct | cgtcttctgc | 1920 |
| ttggaactca | agctccgtcg | agaaacccca | tcatctttct | tgatcagact | aacatccgtc | 1980 |
| ctcttattcg | aaccagcatc | atctttacca | gtaatattaa | ccaaagcctc | agaattctca | 2040 |
| ttagcaacaa | catccagtcc | tttaatcttc | tccatatata | actcatcctt | tctcggtctg | 2100 |
| cctccaaacc | gtaaaaactc | aactttgctt | tcattatcat | gtgcccacct | agactgaaca | 2160 |

-continued

| | |
|---|---|
| taaaatccaa gatacgtcca aagcgtaatc aaaagcagcc aataaaccaa ccggctacta | 2220 |
| cgaaaccact gaaacgctcc tcctccacca tgacctctac gcggagtcct accagaatac | 2280 |
| actctaggtg taccccttgg agtagacctc cctgacagtg aagacttaac acttgtctgt | 2340 |
| ctcagcggcg ataaccgaat ctcctccat | 2369 |

<210> SEQ ID NO 6
<211> LENGTH: 1799
<212> TYPE: DNA
<213> ORGANISM: Arabidopsis thaliana
<220> FEATURE:
<221> NAME/KEY: CDS
<222> LOCATION: (170)..(1603)

<400> SEQUENCE: 6

| | |
|---|---|
| gtcgacccac gcgtccgctc atctctcatc gttccgggag aagagaagag agacccatcc | 60 |
| ctcacttcaa agttcaaagt ctcgaaggat cttctccaac tctctctaaa caagattcca | 120 |
| aattttcaaa ggtgaatttg tttgatagaa tcaagaacaa accttaaa atg gcg cat | 178 |
| Met Ala His | |
| 1 | |

| | |
|---|---|
| cta ctt tca gct tca tgc cct tca gtt atc tca ctt agc agc agc agc | 226 |
| Leu Leu Ser Ala Ser Cys Pro Ser Val Ile Ser Leu Ser Ser Ser Ser | |
| 5             10              15 | |

| | |
|---|---|
| agc aag aat tca gtt aag ccg ttt gtt tca ggg cag acc ttc ttc aat | 274 |
| Ser Lys Asn Ser Val Lys Pro Phe Val Ser Gly Gln Thr Phe Phe Asn | |
| 20           25            30            35 | |

| | |
|---|---|
| gct cag ctt ctt tca aga tct tct ctc aaa gga ctt ctc ttc caa gag | 322 |
| Ala Gln Leu Leu Ser Arg Ser Ser Leu Lys Gly Leu Leu Phe Gln Glu | |
| 40            45            50 | |

| | |
|---|---|
| aag aaa ccg aga aaa agc tgc gtt ttc aga gca act gct gta cct ata | 370 |
| Lys Lys Pro Arg Lys Ser Cys Val Phe Arg Ala Thr Ala Val Pro Ile | |
| 55           60            65 | |

| | |
|---|---|
| acc caa caa gca cca ccc gaa aca tct acc aat aac tca tcc tct aaa | 418 |
| Thr Gln Gln Ala Pro Pro Glu Thr Ser Thr Asn Asn Ser Ser Ser Lys | |
| 70            75            80 | |

| | |
|---|---|
| cca aag cgt gtt atg gtc att ggt gga gat ggt tat tgc ggt tgg gct | 466 |
| Pro Lys Arg Val Met Val Ile Gly Gly Asp Gly Tyr Cys Gly Trp Ala | |
| 85           90            95 | |

| | |
|---|---|
| act gct ctc cac ttg tcc aag aag aat tac gaa gtt tgc att gtt gac | 514 |
| Thr Ala Leu His Leu Ser Lys Lys Asn Tyr Glu Val Cys Ile Val Asp | |
| 100         105          110         115 | |

| | |
|---|---|
| aac ctt gta aga cgt ctt ttc gac cac cag ctt gga ctt gag tca ttg | 562 |
| Asn Leu Val Arg Arg Leu Phe Asp His Gln Leu Gly Leu Glu Ser Leu | |
| 120         125          130 | |

| | |
|---|---|
| act cct att gcc tcc att cat gac cga atc agc cga tgg aag gct ttg | 610 |
| Thr Pro Ile Ala Ser Ile His Asp Arg Ile Ser Arg Trp Lys Ala Leu | |
| 135         140          145 | |

| | |
|---|---|
| aca ggg aaa tca att gag ttg tac gtt ggt gat atc tgt gat ttc gaa | 658 |
| Thr Gly Lys Ser Ile Glu Leu Tyr Val Gly Asp Ile Cys Asp Phe Glu | |
| 150         155          160 | |

| | |
|---|---|
| ttc tta gct gag tct ttc aag tct ttt gag ccg gat tca gtt gtc cac | 706 |
| Phe Leu Ala Glu Ser Phe Lys Ser Phe Glu Pro Asp Ser Val Val His | |
| 165         170          175 | |

| | |
|---|---|
| ttt ggg gaa cag aga tcc gct cct tac tcg atg att gac cgg tcc aga | 754 |
| Phe Gly Glu Gln Arg Ser Ala Pro Tyr Ser Met Ile Asp Arg Ser Arg | |
| 180         185          190         195 | |

| | |
|---|---|
| gca gtt tat aca cag cac aac aat gtg att ggg act ctc aac gtt ctc | 802 |
| Ala Val Tyr Thr Gln His Asn Asn Val Ile Gly Thr Leu Asn Val Leu | |
| 200         205          210 | |

-continued

| | |
|---|---|
| ttt gct ata aaa gag ttt gga gag gag tgt cat ctt gta aaa ctt ggg<br>Phe Ala Ile Lys Glu Phe Gly Glu Glu Cys His Leu Val Lys Leu Gly<br>          215                    220                    225 | 850 |
| acg atg ggt gag tat gga act cca aat att gac atc gag gaa ggt tat<br>Thr Met Gly Glu Tyr Gly Thr Pro Asn Ile Asp Ile Glu Glu Gly Tyr<br>        230                   235                    240 | 898 |
| ata acc ata acc cac aac ggt aga act gac act ttg cca tac ccc aag<br>Ile Thr Ile Thr His Asn Gly Arg Thr Asp Thr Leu Pro Tyr Pro Lys<br>245                    250                    255 | 946 |
| caa gct agc tcc ttt tat cat ctt agc aaa gtt cat gat tcg cac aac<br>Gln Ala Ser Ser Phe Tyr His Leu Ser Lys Val His Asp Ser His Asn<br>260                    265                   270              275 | 994 |
| att gct ttt act tgc aag gct tgg ggt att aga gcc act gat ctc aac<br>Ile Ala Phe Thr Cys Lys Ala Trp Gly Ile Arg Ala Thr Asp Leu Asn<br>                280                   285                    290 | 1042 |
| caa gga gtt gtt tat gga gtg aag act gat gag aca gag atg cat gag<br>Gln Gly Val Val Tyr Gly Val Lys Thr Asp Glu Thr Glu Met His Glu<br>                  295                   300                  305 | 1090 |
| gaa ctc cgt aac cga ctg gat tac gat gct gtg ttt ggt aca gca ctt<br>Glu Leu Arg Asn Arg Leu Asp Tyr Asp Ala Val Phe Gly Thr Ala Leu<br>310                    315                    320 | 1138 |
| aac cgg ttc tgt gtg caa gct gct gtt ggt cac cca ctt aca gtt tat<br>Asn Arg Phe Cys Val Gln Ala Ala Val Gly His Pro Leu Thr Val Tyr<br>        325                   330                    335 | 1186 |
| ggt aaa ggt ggt cag acg aga ggc tac ctc gat ata aga gac acg gtt<br>Gly Lys Gly Gly Gln Thr Arg Gly Tyr Leu Asp Ile Arg Asp Thr Val<br>340                    345                   350              355 | 1234 |
| caa tgt gtt gag atc gct ata gca aac ccg gca aaa gct ggt gag ttc<br>Gln Cys Val Glu Ile Ala Ile Ala Asn Pro Ala Lys Ala Gly Glu Phe<br>                360                   365                  370 | 1282 |
| cgg gtc ttc aac caa ttt aca gaa cag ttt tca gtc aat gaa ctg gct<br>Arg Val Phe Asn Gln Phe Thr Glu Gln Phe Ser Val Asn Glu Leu Ala<br>                  375                   380                  385 | 1330 |
| tca ctc gtc act aaa gcg ggt tca aag ctt ggg cta gac gtg aaa aag<br>Ser Leu Val Thr Lys Ala Gly Ser Lys Leu Gly Leu Asp Val Lys Lys<br>                390                   395                  400 | 1378 |
| atg acg gtg cct aac ccg aga gtg gag gca gaa gaa cat tac tac aac<br>Met Thr Val Pro Asn Pro Arg Val Glu Ala Glu Glu His Tyr Tyr Asn<br>405                    410                    415 | 1426 |
| gca aag cac act aag ctg atg gaa ctt gga ctt gag cct cac tat cta<br>Ala Lys His Thr Lys Leu Met Glu Leu Gly Leu Glu Pro His Tyr Leu<br>420                    425                   430              435 | 1474 |
| tct gac tca ctt ctt gat tcg ttg ctc aac ttt gct gtt cag ttt aaa<br>Ser Asp Ser Leu Leu Asp Ser Leu Leu Asn Phe Ala Val Gln Phe Lys<br>                440                   445                  450 | 1522 |
| gat cgt gtg gac acg aaa caa atc atg cct agt gtt tcc tgg aag aag<br>Asp Arg Val Asp Thr Lys Gln Ile Met Pro Ser Val Ser Trp Lys Lys<br>                  455                   460                  465 | 1570 |
| att ggc gtc aag act aag tcc atg acc aca taa agtgcagacc aatattacac<br>Ile Gly Val Lys Thr Lys Ser Met Thr Thr<br>                470                   475 | 1623 |
| ataaggagag attatgaaag agatgatgtg ttgtttggta tcttcaaact tcatttctgc | 1683 |
| aaaagacttg ctaggcttaa gaggttttgt ccatattaca ttgtgcaggt tctttaatgt | 1743 |
| tagatcttaa tttcgatgaa aaaaaaaaaa aaaaaaaaa aaaaagggc ggccgc | 1799 |

<210> SEQ ID NO 7
<211> LENGTH: 477
<212> TYPE: PRT
<213> ORGANISM: Arabidopsis thaliana

<400> SEQUENCE: 7

| | | | | | | | | | | | | | | | |
|---|---|---|---|---|---|---|---|---|---|---|---|---|---|---|---|
|Met|Ala|His|Leu|Leu|Ser|Ala|Ser|Cys|Pro|Ser|Val|Ile|Ser|Leu|Ser|
|1| | | |5| | | | |10| | | | |15| |
|Ser|Ser|Ser|Ser|Lys|Asn|Ser|Val|Lys|Pro|Phe|Val|Ser|Gly|Gln|Thr|
| | | |20| | | | |25| | | | |30| | |
|Phe|Phe|Asn|Ala|Gln|Leu|Leu|Ser|Arg|Ser|Ser|Leu|Lys|Gly|Leu|Leu|
| | |35| | | | |40| | | | |45| | | |
|Phe|Gln|Glu|Lys|Lys|Pro|Arg|Lys|Ser|Cys|Val|Phe|Arg|Ala|Thr|Ala|
| |50| | | | |55| | | | |60| | | | |
|Val|Pro|Ile|Thr|Gln|Gln|Ala|Pro|Pro|Glu|Thr|Ser|Thr|Asn|Asn|Ser|
|65| | | | |70| | | | |75| | | | |80|
|Ser|Ser|Lys|Pro|Lys|Arg|Val|Met|Val|Ile|Gly|Gly|Asp|Gly|Tyr|Cys|
| | | | |85| | | | |90| | | | |95| |
|Gly|Trp|Ala|Thr|Ala|Leu|His|Leu|Ser|Lys|Lys|Asn|Tyr|Glu|Val|Cys|
| | | |100| | | | |105| | | | |110| | |
|Ile|Val|Asp|Asn|Leu|Val|Arg|Arg|Leu|Phe|Asp|His|Gln|Leu|Gly|Leu|
| | |115| | | | |120| | | | |125| | | |
|Glu|Ser|Leu|Thr|Pro|Ile|Ala|Ser|Ile|His|Asp|Arg|Ile|Ser|Arg|Trp|
| |130| | | | |135| | | | |140| | | | |
|Lys|Ala|Leu|Thr|Gly|Lys|Ser|Ile|Glu|Leu|Tyr|Val|Gly|Asp|Ile|Cys|
|145| | | | |150| | | | |155| | | | |160|
|Asp|Phe|Glu|Phe|Leu|Ala|Glu|Ser|Phe|Lys|Ser|Phe|Glu|Pro|Asp|Ser|
| | | | |165| | | | |170| | | | |175| |
|Val|Val|His|Phe|Gly|Glu|Gln|Arg|Ser|Ala|Pro|Tyr|Ser|Met|Ile|Asp|
| | | |180| | | | |185| | | | |190| | |
|Arg|Ser|Arg|Ala|Val|Tyr|Thr|Gln|His|Asn|Asn|Val|Ile|Gly|Thr|Leu|
| | |195| | | | |200| | | | |205| | | |
|Asn|Val|Leu|Phe|Ala|Ile|Lys|Glu|Phe|Gly|Glu|Glu|Cys|His|Leu|Val|
| |210| | | | |215| | | | |220| | | | |
|Lys|Leu|Gly|Thr|Met|Gly|Glu|Tyr|Gly|Thr|Pro|Asn|Ile|Asp|Ile|Glu|
|225| | | | |230| | | | |235| | | | |240|
|Glu|Gly|Tyr|Ile|Thr|Ile|Thr|His|Asn|Gly|Arg|Thr|Asp|Thr|Leu|Pro|
| | | | |245| | | | |250| | | | |255| |
|Tyr|Pro|Lys|Gln|Ala|Ser|Ser|Phe|Tyr|His|Leu|Ser|Lys|Val|His|Asp|
| | | |260| | | | |265| | | | |270| | |
|Ser|His|Asn|Ile|Ala|Phe|Thr|Cys|Lys|Ala|Trp|Gly|Ile|Arg|Ala|Thr|
| | |275| | | | |280| | | | |285| | | |
|Asp|Leu|Asn|Gln|Gly|Val|Val|Tyr|Gly|Val|Lys|Thr|Asp|Glu|Thr|Glu|
| |290| | | | |295| | | | |300| | | | |
|Met|His|Glu|Glu|Leu|Arg|Asn|Arg|Leu|Asp|Tyr|Asp|Ala|Val|Phe|Gly|
|305| | | | |310| | | | |315| | | | |320|
|Thr|Ala|Leu|Asn|Arg|Phe|Cys|Val|Gln|Ala|Ala|Val|Gly|His|Pro|Leu|
| | | | |325| | | | |330| | | | |335| |
|Thr|Val|Tyr|Gly|Lys|Gly|Gly|Gln|Thr|Arg|Gly|Tyr|Leu|Asp|Ile|Arg|
| | | |340| | | | |345| | | | |350| | |
|Asp|Thr|Val|Gln|Cys|Val|Glu|Ile|Ala|Ile|Ala|Asn|Pro|Ala|Lys|Ala|
| | |355| | | | |360| | | | |365| | | |
|Gly|Glu|Phe|Arg|Val|Phe|Asn|Gln|Phe|Thr|Glu|Gln|Phe|Ser|Val|Asn|
| |370| | | | |375| | | | |380| | | | |
|Glu|Leu|Ala|Ser|Leu|Val|Thr|Lys|Ala|Gly|Ser|Lys|Leu|Gly|Leu|Asp|
|385| | | | |390| | | | |395| | | | |400|
|Val|Lys|Lys|Met|Thr|Val|Pro|Asn|Pro|Arg|Val|Glu|Ala|Glu|Glu|His|

```
                    405                 410                 415
Tyr Tyr Asn Ala Lys His Thr Lys Leu Met Glu Leu Gly Leu Glu Pro
            420                 425                 430

His Tyr Leu Ser Asp Ser Leu Leu Asp Ser Leu Leu Asn Phe Ala Val
            435                 440                 445

Gln Phe Lys Asp Arg Val Asp Thr Lys Gln Ile Met Pro Ser Val Ser
    450                 455                 460

Trp Lys Lys Ile Gly Val Lys Thr Lys Ser Met Thr Thr
465                 470                 475

<210> SEQ ID NO 8
<211> LENGTH: 1209
<212> TYPE: DNA
<213> ORGANISM: Cyanobacterium Synechococcus

<400> SEQUENCE: 8
gtgaagattc ttgtattggg tggcgatggt ttctgcgggt ggccctgcgc tctcaatttg      60
gctgctgcag gtcacgccgt caccattgtt gacaacctcg ttcgccgcaa gacagacgtg     120
gaattggggg ttcagtccct cactccgatc gcgacgattg aacgccggtt gaaggcatgg     180
caagaaacgg gcgggcagcc gattagcttt gtcaatctcg acttagcggc tgattacgat     240
cgcctctgtg cactactgct agaaacgcag ccggatgcga tcgtgcattt tgccgaacag     300
cgcgccgccc cctattcaat gaagagtgca tggcataagc gcttcacggt caataacaac     360
gtcaacgcca cccacaatct gctctgcgcc tgtgtggatg tcggcctcaa gtcccacatt     420
gtccacttgg caccatgggg cgtctatgga tacggtagcc atcgcggggc tacgattcct     480
gaaggctact agaagtggaa gtcgtccag cgggatggcc aacgctttga agagaagatt      540
cttcaccccg ttgatccggg tagcgtctat cacatgacca agacgctgga tcaattgttg     600
ttctactact acaacaagaa cgacaacatc aagtcaccg accttcacca gggtattgtc      660
tggggcacga acaccgatca ctgtaatctc cacccggatc tgaccaatcg gttcgactac     720
gacggtgatt acggcacagt cttgaaccgc ttcttgatgc aggcggcgat cggctatccc     780
ttgactgtgc atggcgttgg tggccaaacc cgagccttca tccacattcg cgactcagtg     840
cgctgcgtcc aactggcgat cgaaaatccg ccagcagcca atgaaaaagt ccgcatcttt     900
aaccagatga cggaaaccta ccaagtcaag gatttggcag agaaagtggc ggcattgacc     960
ggtgctgaaa tcgcctacct gcccaatcca cgcaaggaag cccttgagaa cgacttgatt    1020
gtcgacaacc gctgcttgat tgatttaggc ctcaatccga ccaccttgga caatggcctg    1080
atgagcgaag tggtagaaat tgcgcagaag tttgccgatc gctgcgatcg cgccaaaatt    1140
ccctgcgttt ctgcctggac ccgtaatcaa gctgaagctc tcagcgctcc tgaaaccgct    1200
ctgcgctaa                                                            1209

<210> SEQ ID NO 9
<211> LENGTH: 402
<212> TYPE: PRT
<213> ORGANISM: Cyanobacterium Synechococcus

<400> SEQUENCE: 9

Met Lys Ile Leu Val Leu Gly Gly Asp Gly Phe Cys Gly Trp Pro Cys
1               5                   10                  15

Ala Leu Asn Leu Ala Ala Ala Gly His Ala Val Thr Ile Val Asp Asn
            20                  25                  30

Leu Val Arg Arg Lys Thr Asp Val Glu Leu Gly Val Gln Ser Leu Thr
```

```
                35                  40                  45
Pro Ile Ala Thr Ile Glu Arg Arg Leu Lys Ala Trp Gln Glu Thr Gly
 50                  55                  60

Gly Gln Pro Ile Ser Phe Val Asn Leu Asp Leu Ala Ala Asp Tyr Asp
 65                  70                  75                  80

Arg Leu Cys Ala Leu Leu Glu Thr Gln Pro Asp Ala Ile Val His
                 85                  90                  95

Phe Ala Glu Gln Arg Ala Ala Pro Tyr Ser Met Lys Ser Ala Trp His
                100                 105                 110

Lys Arg Phe Thr Val Asn Asn Val Asn Ala Thr His Asn Leu Leu
                115                 120                 125

Cys Ala Cys Val Asp Val Gly Leu Lys Ser His Ile Val His Leu Gly
                130                 135                 140

Thr Met Gly Val Tyr Gly Tyr Gly Ser His Arg Gly Ala Thr Ile Pro
145                 150                 155                 160

Glu Gly Tyr Leu Glu Val Glu Val Val Gln Arg Asp Gly Gln Arg Phe
                165                 170                 175

Glu Glu Lys Ile Leu His Pro Val Asp Pro Gly Ser Val Tyr His Met
                180                 185                 190

Thr Lys Thr Leu Asp Gln Leu Leu Phe Tyr Tyr Asn Lys Asn Asp
                195                 200                 205

Asn Ile Gln Val Thr Asp Leu His Gln Gly Ile Val Trp Gly Thr Asn
210                 215                 220

Thr Asp His Cys Asn Leu His Pro Asp Leu Thr Asn Arg Phe Asp Tyr
225                 230                 235                 240

Asp Gly Asp Tyr Gly Thr Val Leu Asn Arg Phe Leu Met Gln Ala Ala
                245                 250                 255

Ile Gly Tyr Pro Leu Thr Val His Gly Val Gly Gly Gln Thr Arg Ala
                260                 265                 270

Phe Ile His Ile Arg Asp Ser Val Arg Cys Val Gln Leu Ala Ile Glu
                275                 280                 285

Asn Pro Pro Ala Ala Asn Glu Lys Val Arg Ile Phe Asn Gln Met Thr
290                 295                 300

Glu Thr Tyr Gln Val Lys Asp Leu Ala Glu Lys Val Ala Ala Leu Thr
305                 310                 315                 320

Gly Ala Glu Ile Ala Tyr Leu Pro Asn Pro Arg Lys Glu Ala Leu Glu
                325                 330                 335

Asn Asp Leu Ile Val Asp Asn Arg Cys Leu Ile Asp Leu Gly Leu Asn
                340                 345                 350

Pro Thr Thr Leu Asp Asn Gly Leu Met Ser Glu Val Val Glu Ile Ala
                355                 360                 365

Gln Lys Phe Ala Asp Arg Cys Asp Arg Ala Lys Ile Pro Cys Val Ser
                370                 375                 380

Ala Trp Thr Arg Asn Gln Ala Glu Ala Leu Ser Ala Pro Glu Thr Ala
385                 390                 395                 400

Leu Arg

<210> SEQ ID NO 10
<211> LENGTH: 26
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Synthetic
```

```
<400> SEQUENCE: 10
aaaggatccc gtgttatggt cattgg                                              26

<210> SEQ ID NO 11
<211> LENGTH: 26
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Synthetic

<400> SEQUENCE: 11
gtcggatcct tatgtggtca tggact                                              26

<210> SEQ ID NO 12
<211> LENGTH: 24
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Synthetic

<400> SEQUENCE: 12
tttggatccc gcatcgctct cttt                                                24

<210> SEQ ID NO 13
<211> LENGTH: 23
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Synthetic

<400> SEQUENCE: 13
ataagcttcg agctcaggcc gct                                                 23

<210> SEQ ID NO 14
<211> LENGTH: 29
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Synthetic

<400> SEQUENCE: 14
cgggatccat gacgactctt tcttctata                                           29

<210> SEQ ID NO 15
<211> LENGTH: 28
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Synthetic

<400> SEQUENCE: 15
aaggatccct acacgttacc ttccggta                                            28

<210> SEQ ID NO 16
<211> LENGTH: 28
<212> TYPE: DNA
```

```
<213> ORGANISM: Artificial Sequence
<220> FEATURE:
<223> OTHER INFORMATION: Synthetic
<221> NAME/KEY: misc_feature
<223> OTHER INFORMATION: Synthetic

<400> SEQUENCE: 16
aaggatccat ggcttcacaa accaaact                                           28

<210> SEQ ID NO 17
<211> LENGTH: 28
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Synthetic

<400> SEQUENCE: 17
gcggatcctc atattttgaa aaagcact                                           28

<210> SEQ ID NO 18
<211> LENGTH: 27
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Synthetic

<400> SEQUENCE: 18
agggtaccat ggagggattc ggttatc                                            27

<210> SEQ ID NO 19
<211> LENGTH: 28
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Synthetic

<400> SEQUENCE: 19
gcggtacctt aaggtctatg catttgac                                           28

<210> SEQ ID NO 20
<211> LENGTH: 26
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Synthetic

<400> SEQUENCE: 20
ctaggtacca aatggcgcat ctactt                                             26

<210> SEQ ID NO 21
<211> LENGTH: 26
<212> TYPE: DNA
<213> ORGANISM: Artificial Sequence
<220> FEATURE:
<223> OTHER INFORMATION: Synthetic
<221> NAME/KEY: misc_feature
<223> OTHER INFORMATION: Synthetic

<400> SEQUENCE: 21
aaggatcctg cgctaaagtc gcactc                                             26
```

```
<210> SEQ ID NO 22
<211> LENGTH: 71
<212> TYPE: DNA
<213> ORGANISM: Artificial Sequence
<220> FEATURE:
<223> OTHER INFORMATION: Synthetic
<221> NAME/KEY: misc_feature
<222> LOCATION: (12)..(12)
<223> OTHER INFORMATION: The residue at this position is linked to six
      contiguous histidine residues

<400> SEQUENCE: 22
atgagaggat cgggatccgc atgcgagctc ggtaccccgg gtcgacctgc agccaagctt    60
aattagctga g                                                         71

<210> SEQ ID NO 23
<211> LENGTH: 73
<212> TYPE: DNA
<213> ORGANISM: Artificial Sequence
<220> FEATURE:
<223> OTHER INFORMATION: Synthetic
<221> NAME/KEY: misc_feature
<222> LOCATION: (12)..(12)
<223> OTHER INFORMATION: The residue at this position is linked to six
      contiguous histidine residues

<400> SEQUENCE: 23
atgagaggat ctacggatcc gcatgcgagc tcggtacccc gggtcgacct gcagccaagc    60
ttaattagct gag                                                       73

<210> SEQ ID NO 24
<211> LENGTH: 72
<212> TYPE: DNA
<213> ORGANISM: Artificial Sequence
<220> FEATURE:
<223> OTHER INFORMATION: Synthetic
<221> NAME/KEY: misc_feature
<222> LOCATION: (12)..(12)
<223> OTHER INFORMATION: The residue at this position is linked to six
      contiguous histidine residues

<400> SEQUENCE: 24
atgagaggat ctgggatccg catgcgagct cggtaccccg ggtcgacctg cagccaagct    60
taattagctg ag                                                        72
```